US012780950B2

(12) United States Patent
Tian et al.

(10) Patent No.: US 12,780,950 B2
(45) Date of Patent: Nov. 3, 2026

(54) BISPECIFIC ANTIBODIES TARGETING CD3 AND B7H6 AND USES OF THE SAME THEREOF

(71) Applicant: Hefei TG ImmunoPharma Co., Ltd., Hefei (CN)

(72) Inventors: Zhigang Tian, Hefei (CN); Ying Cheng, Hefei (CN); Weihua Xiao, Hefei (CN); Guoshuai Cao, Hefei (CN); Haoyu Sun, Hefei (CN); Rui Sun, Hefei (CN)

(73) Assignee: HEFEI TG IMMUNOPHARMA CO., LTD., Hefei (CN)

( * ) Notice: Subject to any disclaimer, the term of this patent is extended or adjusted under 35 U.S.C. 154(b) by 495 days.

(21) Appl. No.: 18/389,819

(22) Filed: Dec. 20, 2023

(65) Prior Publication Data

US 2024/0124615 A1 Apr. 18, 2024

Related U.S. Application Data

(63) Continuation of application No. PCT/CN2022/100475, filed on Jun. 22, 2022.

(30) Foreign Application Priority Data

Dec. 7, 2021 (CN) ......................... 202111485404.0

(51) Int. Cl.

| | |
|---|---|
| ***C07K 16/46*** | (2006.01) |
| ***A61P 35/00*** | (2006.01) |
| ***C12N 15/63*** | (2006.01) |
| ***G01N 33/575*** | (2026.01) |

(52) U.S. Cl.

CPC ............ *C07K 16/468* (2013.01); *A61P 35/00* (2018.01); *C12N 15/63* (2013.01); *G01N 33/575* (2026.01); *C07K 2317/52* (2013.01); *C07K 2317/565* (2013.01)

(58) Field of Classification Search

None

See application file for complete search history.

(56) References Cited

U.S. PATENT DOCUMENTS

| | | | |
|---|---|---|---|
| 10,087,250 | B2 | 10/2018 | Bruenker et al. |
| 2013/0004432 | A1 | 1/2013 | Pierres et al. |
| 2013/0060011 | A1 | 3/2013 | Bruenker et al. |
| 2018/0267055 | A1 | 9/2018 | Carey |
| 2019/0127470 | A1 | 5/2019 | Ackerman et al. |
| 2019/0248916 | A1 | 8/2019 | Benz et al. |
| 2021/0107983 | A1 | 4/2021 | Susanne et al. |

FOREIGN PATENT DOCUMENTS

| | | | |
|---|---|---|---|
| CN | 105934253 | A | 9/2016 |
| CN | 107614013 | A | 1/2018 |
| CN | 110511278 | A | 11/2019 |
| CN | 113286821 | A | 8/2021 |
| CN | 114395044 | A | 4/2022 |
| CN | 114395047 | A | 4/2022 |
| JP | 2015519337 | A | 7/2015 |
| WO | 2013169691 | A1 | 11/2013 |
| WO | 2017132279 | A1 | 8/2017 |
| WO | 2017181001 | A1 | 10/2017 |
| WO | 2021064137 | A2 | 4/2021 |

OTHER PUBLICATIONS

First Office Action dated Dec. 13, 2024 received in corresponding patent family application No. CA3211762.

Tamura et al., "Structural Correlates of an Anticarcinoma Antibody: Identification of Specificity-Determining Residues (SDRs) and Development of a Minimally Immunogenic Antibody Variant by Retention of SDRs Only", J. Immunol., vol. 164, No. 3, pp. 1432-1441, Feb. 2000 (Feb. 2000).

First Office Action dated Dec. 13, 2023 received in corresponding patent family application No. TW111146967. English translation attached.

Wu et al., "B7H6-Specific Bispecific T Cell Engagers Lead to Tumor Elimination and Host Antitumor Immunity", J Immunol, vol. 194, Issue 11, Jun. 1, 2015, pp. 5305-5311.

The Decision of Rejection dated Apr. 3, 2024 received in corresponding patent family application No. TW111146967. English translation attached.

Extended European Search Report dated Jan. 29, 2025 received in corresponding European Application No. EP22902772.7.

First Office Action dated Jan. 31, 2024 received in corresponding patent family application No. RU2023128925. English translation attached.

Grant Notice dated Jun. 4, 2024 received in corresponding patent family application No. RU2023128925. English translation attached.

Shapoval A.I. et al., "New points of immune response control for immunotherapy of oncological diseases" Russian Journal of Oncology, 2017, 22(4), pp. 175-179, abstract, p. 178, left col., second paragraph. English translation attached.

Mariuzza R.A., "The structural basis of antigen-antibody recognition" Ann. Rev. Biophys. Biophys. Chem., 1987, vol. 16, pp. 139-159.

Rudikoff S. et al., "Single amino acid substitution altering antigen-binding specificity" Immunology, 1982, vol. 78, pp. 1979-1983.

Kussie P.H. et al., "A single engineered amino acid substitution changes antibody fine specificity" J Immunol, Jan. 1994, 152(1), pp. 146-152.

Baylot V. et al., "TCTP has a crucial role in the different stages of prostate cancer malignant progression" Results Probl Cell Differ, 2017, vol. 64, pp. 255-261.

(Continued)

*Primary Examiner* — Sharon X Wen

(57) ABSTRACT

Provided are a bispecific antibody and use thereof. The recombinant antibody includes: a CDR Sequence selected from at least one of CD3 antibody variable region CDR sequences: SEQ ID NO: 1 to SEQ ID NO: 6, and B7H6 antibody variable region CDR sequences: SEQ ID NO: 7 to SEQ ID NO: 12; or an amino acid sequence having at least 95% identity thereto. The recombinant antibodies prepared according to the present application can simultaneously target CD3 and B7H6 antigens, and they have a significantly prolonged half-life, exhibiting a stronger tumor-inhibiting ability than single-target antibodies.

20 Claims, 10 Drawing Sheets

Specification includes a Sequence Listing.

(56) References Cited

OTHER PUBLICATIONS

Muller S. et al., "Spliceosomal peptide P140 for immunotherapy of systemic lupus erythematosus: results of an early phase II clinical trial" Arthritis & Rheumatism, Dec. 2008, vol. 58, No. 12, pp. 3873-3883.

International Search Report dated Sep. 20, 2022 in International Application No. PCT/CN2022/100475. English translation attached.

The First Office from corresponding Chinese Application No. 202111485404.0, dated May 7, 2023. English translation attached.

The Grant Notice from corresponding Chinese Application No. 202111485404.0, dated Aug. 11, 2023. English translation attached.

Sun, Xin et al. "B7-H6 as an efficient target for T cell-induced cytotoxicity in haematologic malignant cells" Investigational New Drugs, vol. 39, Aug. 7, 2020 (Aug. 7, 2020), pp. 24-33.

First Office Action dated Jun. 19, 2025 received in corresponding patent family application No. AU2022404170.

Notice of Reasons for Refusal dated May 27, 2025 received in corresponding patent family application No. JP2023555735. English translation attached.

Intention to grant dated Oct. 28, 2025 received in corresponding patent family application No. EP22902772.7.

Decision of Refusal dated Sep. 2, 2025 received in corresponding patent family application No. JP2023555735. English translation attached.

SEQUENCE LISTING

```
Sequence total quantity: 88
SEQ ID NO: 1            moltype = AA  length = 11
FEATURE                 Location/Qualifiers
REGION                  1..11
                        note = 1
source                  1..11
                        mol_type = protein
                        organism = synthetic construct
SEQUENCE: 1
RASQDIRNYL N                                                 11

SEQ ID NO: 2            moltype = AA  length = 7
FEATURE                 Location/Qualifiers
REGION                  1..7
                        note = 2
source                  1..7
                        mol_type = protein
                        organism = synthetic construct
SEQUENCE: 2
YTSRLES                                                      7

SEQ ID NO: 3            moltype = AA  length = 9
FEATURE                 Location/Qualifiers
REGION                  1..9
                        note = 3
source                  1..9
                        mol_type = protein
                        organism = synthetic construct
SEQUENCE: 3
```

-continued

```
QQGNTLPWT                                                         9

SEQ ID NO: 4           moltype = AA  length = 5
FEATURE                Location/Qualifiers
REGION                 1..5
                       note = 4
source                 1..5
                       mol_type = protein
                       organism = synthetic construct
SEQUENCE: 4
GYTMN                                                             5

SEQ ID NO: 5           moltype = AA  length = 17
FEATURE                Location/Qualifiers
REGION                 1..17
                       note = 5
source                 1..17
                       mol_type = protein
                       organism = synthetic construct
SEQUENCE: 5
LINPYKGVST YNQKFKD                                                17

SEQ ID NO: 6           moltype = AA  length = 13
FEATURE                Location/Qualifiers
REGION                 1..13
                       note = 6
source                 1..13
                       mol_type = protein
                       organism = synthetic construct
SEQUENCE: 6
SGYYGDSDWY FDV                                                    13

SEQ ID NO: 7           moltype = AA  length = 15
FEATURE                Location/Qualifiers
REGION                 1..15
                       note = 7
source                 1..15
                       mol_type = protein
                       organism = synthetic construct
SEQUENCE: 7
KASQSVDYDG DSYMN                                                  15

SEQ ID NO: 8           moltype = AA  length = 7
FEATURE                Location/Qualifiers
REGION                 1..7
                       note = 8
source                 1..7
                       mol_type = protein
                       organism = synthetic construct
SEQUENCE: 8
AASTLHS                                                           7

SEQ ID NO: 9           moltype = AA  length = 9
FEATURE                Location/Qualifiers
REGION                 1..9
                       note = 9
source                 1..9
                       mol_type = protein
                       organism = synthetic construct
SEQUENCE: 9
QQSKEDPRT                                                         9

SEQ ID NO: 10          moltype = AA  length = 5
FEATURE                Location/Qualifiers
REGION                 1..5
                       note = 10
source                 1..5
                       mol_type = protein
                       organism = synthetic construct
SEQUENCE: 10
DYNMD                                                             5

SEQ ID NO: 11          moltype = AA  length = 17
FEATURE                Location/Qualifiers
REGION                 1..17
                       note = 11
source                 1..17
                       mol_type = protein
                       organism = synthetic construct
```

```
SEQUENCE: 11
DINPNNGGTL YNQKFRG                                                17

SEQ ID NO: 12          moltype = AA  length = 11
FEATURE                Location/Qualifiers
REGION                 1..11
                       note = 12
source                 1..11
                       mol_type = protein
                       organism = synthetic construct
SEQUENCE: 12
SEVFYGNYAD Y                                                      11

SEQ ID NO: 13          moltype = AA  length = 108
FEATURE                Location/Qualifiers
REGION                 1..108
                       note = 13
source                 1..108
                       mol_type = protein
                       organism = synthetic construct
SEQUENCE: 13
MDIQMTQSPS SLSASVGDRV TITCRASQDI RNYLNWYQQK PGKAPKLLIY YTSRLESGVP  60
SRFSGSGSGT DYTLTISSLQ PEDFATYYCQ QGNTLPWTFG QGTKVEIK              108

SEQ ID NO: 14          moltype = AA  length = 122
FEATURE                Location/Qualifiers
REGION                 1..122
                       note = 14
source                 1..122
                       mol_type = protein
                       organism = synthetic construct
SEQUENCE: 14
EVQLVESGGG LVQPGGSLRL SCAASGYSFT GYTMNWVRQA PGKGLEWVAL INPYKGVSTY  60
NQKFKDRFTI SVDKSKNTAY LQMNSLRAED TAVYYCARSG YYGDSDWYFD VWGQGTLVTV  120
SS                                                                122

SEQ ID NO: 15          moltype = AA  length = 111
FEATURE                Location/Qualifiers
REGION                 1..111
                       note = 15
source                 1..111
                       mol_type = protein
                       organism = synthetic construct
SEQUENCE: 15
DIVLTQSPVS LAVPLGQRAT ISCKASQSVD YDGDSYMNWY QQKPGQPPKL LIYAASTLHS  60
GIPVRFSGSG SGTDFTLNIH PVEEEDAASY YCQQSKEDPR TFGGGTKLEI K         111

SEQ ID NO: 16          moltype = AA  length = 111
FEATURE                Location/Qualifiers
REGION                 1..111
                       note = 16
source                 1..111
                       mol_type = protein
                       organism = synthetic construct
SEQUENCE: 16
DIVLTQSPDS LAVSLGERAT INCKASQSVD YDGDSYMNWY QQKPGQPPKL LIYAASTLHS  60
GVPDRFSGSG SGTDFTLTIS SLQAEDVAVY YCQQSKEDPR TFGQGTKLEI K         111

SEQ ID NO: 17          moltype = AA  length = 111
FEATURE                Location/Qualifiers
REGION                 1..111
                       note = 17
source                 1..111
                       mol_type = protein
                       organism = synthetic construct
SEQUENCE: 17
DIVLTQSPDS LAVSLGERAT INCKASQSVD YDGDSYMNWY QQKPGQPPKL LIYAASTLHS  60
GIPDRFSGSG SGTDFTLTIS SLQAEDVAVY YCQQSKEDPR TFGQGTKLEI K         111

SEQ ID NO: 18          moltype = AA  length = 111
FEATURE                Location/Qualifiers
REGION                 1..111
                       note = 18
source                 1..111
                       mol_type = protein
                       organism = synthetic construct
SEQUENCE: 18
DIVLTQSPVS LAVPLGQRAT ISCKASQSVD YDADSYMNWY QQKPGQPPKL LIYAASTLHS  60
GIPVRFSGSG SGTDFTLNIH PVEEEDAASY YCQQSKEDPR TFGGGTKLEI K         111
```

```
SEQ ID NO: 19          moltype = AA  length = 111
FEATURE                Location/Qualifiers
REGION                 1..111
                       note = 19
source                 1..111
                       mol_type = protein
                       organism = synthetic construct
SEQUENCE: 19
DIVLTQTPLS LSVTPGQPAS ISCKASQSVD YDGDSYMNWY LQKPGQPPQL LIYAASTLHS  60
GVPDRFSGSG SGTDFTLKIS RVEAEDVGVY YCQQSKEDPR TFGQGTKLEI K          111

SEQ ID NO: 20          moltype = AA  length = 111
FEATURE                Location/Qualifiers
REGION                 1..111
                       note = 20
source                 1..111
                       mol_type = protein
                       organism = synthetic construct
SEQUENCE: 20
DIVLTQTPLS LSVTPGQPAS ISCKASQSVD YDGDSYMNWY LQKPGQPPQL LIYAASTLHS  60
GIPDRFSGSG SGTDFTLKIS RVEAEDVGVY YCQQSKEDPR TFGQGTKLEI K          111

SEQ ID NO: 21          moltype = AA  length = 120
FEATURE                Location/Qualifiers
REGION                 1..120
                       note = 21
source                 1..120
                       mol_type = protein
                       organism = synthetic construct
SEQUENCE: 21
EVLLQQSGPE VVKPGASVKI TCKASGYTFT DYNMDWVKQS HGKSLEWIGD INPNNGGTLY  60
NQKFRGRVTL IVDKSSSTAY MELRSLTSDD TAVYYCARSE VFYGNYADYW GQGTTLTVSS  120

SEQ ID NO: 22          moltype = AA  length = 120
FEATURE                Location/Qualifiers
REGION                 1..120
                       note = 22
source                 1..120
                       mol_type = protein
                       organism = synthetic construct
SEQUENCE: 22
EVQLVQSGAE VKKPGASVKV SCKASGYTFT DYNMDWVRQA PGQGLEWMGD INPNNGGTLY  60
NQKFRGRVTM TVDTSISTAY MELSRLRSDD TAVYYCARSE VFYGNYADYW GQGTTVTVSS  120

SEQ ID NO: 23          moltype = AA  length = 120
FEATURE                Location/Qualifiers
REGION                 1..120
                       note = 23
source                 1..120
                       mol_type = protein
                       organism = synthetic construct
SEQUENCE: 23
EVQLVQSGAE VKKPGASVKV SCKASGYTFT DYNMDWVRQA PGQGLEWIGD INPNNGGTLY  60
NQKFRGRVTL TVDTSISTAY MELSRLRSDD TAVYYCARSE VFYGNYADYW GQGTTVTVSS  120

SEQ ID NO: 24          moltype = AA  length = 120
FEATURE                Location/Qualifiers
REGION                 1..120
                       note = 24
source                 1..120
                       mol_type = protein
                       organism = synthetic construct
SEQUENCE: 24
EVQLVQSGAE VKKPGASVKV SCKASGYTFT DYNMDWVRQA PGQGLEWIGD INPNNGGTLY  60
NQKFRGRVTL TVDKSISTAY MELSRLRSDD TAVYYCARSE VFYGNYADYW GQGTTVTVSS  120

SEQ ID NO: 25          moltype = AA  length = 120
FEATURE                Location/Qualifiers
REGION                 1..120
                       note = 25
source                 1..120
                       mol_type = protein
                       organism = synthetic construct
SEQUENCE: 25
EVQLVQSGAE VKKPGASVKV SCKASGYTFT DYNMDWVRQA PGKGLEWIGD INPNNGGTLY  60
NQKFRGRVTL TVDKSISTAY MELSRLRSDD TAVYYCARSE VFYGNYADYW GQGTTVTVSS  120

SEQ ID NO: 26          moltype = AA  length = 120
```

```
FEATURE                 Location/Qualifiers
REGION                  1..120
                        note = 26
source                  1..120
                        mol_type = protein
                        organism = synthetic construct
SEQUENCE: 26
EVLLQQSGPE VVKPGASVKI TCKASGYTFT DYNMDWVKQS HGKSLEWIGD INPNNAGTLY  60
NQKFRGRVTL IVDKSSSTAY MELRSLTSDD TAVYYCARSE VFYGNYADYW GQGTTLTVSS  120

SEQ ID NO: 27           moltype = AA  length = 245
FEATURE                 Location/Qualifiers
REGION                  1..245
                        note = 27
source                  1..245
                        mol_type = protein
                        organism = synthetic construct
SEQUENCE: 27
MDIQMTQSPS SLSASVGDRV TITCRASQDI RNYLNWYQQK PGKAPKLLIY YTSRLESGVP  60
SRFSGSGSGT DYTLTISSLQ PEDFATYYCQ QGNTLPWTFG QGTKVEIKGG GGSGGGGSGG  120
GGSEVQLVES GGGLVQPGGS LRLSCAASGY SFTGYTMNWV RQAPGKGLEW VALINPYKGV  180
STYNQKFKDR FTISVDKSKN TAYLQMNSLR AEDTAVYYCA RSGYYGDSDW YFDVWGQGTL  240
VTVSS                                                              245

SEQ ID NO: 28           moltype = AA  length = 246
FEATURE                 Location/Qualifiers
REGION                  1..246
                        note = 28
source                  1..246
                        mol_type = protein
                        organism = synthetic construct
SEQUENCE: 28
DIVLTQSPDS LAVSLGERAT INCKASQSVD YDGDSYMNWY QQKPGQPPKL LIYAASTLHS  60
GVPDRFSGSG SGTDFTLTIS SLQAEDVAVY YCQQSKEDPR TFGQGTKLEI KGGGGSGGGG  120
SGGGGSEVQL VQSGAEVKKP GASVKVSCKA SGYTFTDYNM DWVRQAPGQG LEWMGDINPN  180
NGGTLYNQKF RGRVTMTVDT SISTAYMELS RLRSDDTAVY YCARSEVFYG NYADYWGQGT  240
TVTVSS                                                             246

SEQ ID NO: 29           moltype = AA  length = 246
FEATURE                 Location/Qualifiers
REGION                  1..246
                        note = 29
source                  1..246
                        mol_type = protein
                        organism = synthetic construct
SEQUENCE: 29
DIVLTQSPDS LAVSLGERAT INCKASQSVD YDGDSYMNWY QQKPGQPPKL LIYAASTLHS  60
GVPDRFSGSG SGTDFTLTIS SLQAEDVAVY YCQQSKEDPR TFGQGTKLEI KGGGGSGGGG  120
SGGGGSEVQL VQSGAEVKKP GASVKVSCKA SGYTFTDYNM DWVRQAPGQG LEWIGDINPN  180
NGGTLYNQKF RGRVTLTVDT SISTAYMELS RLRSDDTAVY YCARSEVFYG NYADYWGQGT  240
TVTVSS                                                             246

SEQ ID NO: 30           moltype = AA  length = 246
FEATURE                 Location/Qualifiers
REGION                  1..246
                        note = 30
source                  1..246
                        mol_type = protein
                        organism = synthetic construct
SEQUENCE: 30
DIVLTQSPDS LAVSLGERAT INCKASQSVD YDGDSYMNWY QQKPGQPPKL LIYAASTLHS  60
GVPDRFSGSG SGTDFTLTIS SLQAEDVAVY YCQQSKEDPR TFGQGTKLEI KGGGGSGGGG  120
SGGGGSEVQL VQSGAEVKKP GASVKVSCKA SGYTFTDYNM DWVRQAPGQG LEWIGDINPN  180
NGGTLYNQKF RGRVTLTVDK SISTAYMELS RLRSDDTAVY YCARSEVFYG NYADYWGQGT  240
TVTVSS                                                             246

SEQ ID NO: 31           moltype = AA  length = 246
FEATURE                 Location/Qualifiers
REGION                  1..246
                        note = 31
source                  1..246
                        mol_type = protein
                        organism = synthetic construct
SEQUENCE: 31
DIVLTQSPDS LAVSLGERAT INCKASQSVD YDGDSYMNWY QQKPGQPPKL LIYAASTLHS  60
GVPDRFSGSG SGTDFTLTIS SLQAEDVAVY YCQQSKEDPR TFGQGTKLEI KGGGGSGGGG  120
SGGGGSEVQL VQSGAEVKKP GASVKVSCKA SGYTFTDYNM DWVRQAPGKG LEWIGDINPN  180
NGGTLYNQKF RGRVTLTVDK SISTAYMELS RLRSDDTAVY YCARSEVFYG NYADYWGQGT  240
TVTVSS                                                             246
```

```
SEQ ID NO: 32          moltype = AA  length = 246
FEATURE                Location/Qualifiers
REGION                 1..246
                       note = 32
source                 1..246
                       mol_type = protein
                       organism = synthetic construct
SEQUENCE: 32
DIVLTQSPDS LAVSLGERAT INCKASQSVD YDGDSYMNWY QQKPGQPPKL LIYAASTLHS  60
GIPDRFSGSG SGTDFTLTIS SLQAEDVAVY YCQQSKEDPR TFGQGTKLEI KGGGGSGGGG  120
SGGGGSEVQL VQSGAEVKKP GASVKVSCKA SGYTFTDYNM DWVRQAPGQG LEWMGDINPN  180
NGGTLYNQKF RGRVTMTVDT SISTAYMELS RLRSDDTAVY YCARSEVFYG NYADYWGQGT  240
TVTVSS                                                            246

SEQ ID NO: 33          moltype = AA  length = 246
FEATURE                Location/Qualifiers
REGION                 1..246
                       note = 33
source                 1..246
                       mol_type = protein
                       organism = synthetic construct
SEQUENCE: 33
DIVLTQSPDS LAVSLGERAT INCKASQSVD YDGDSYMNWY QQKPGQPPKL LIYAASTLHS  60
GIPDRFSGSG SGTDFTLTIS SLQAEDVAVY YCQQSKEDPR TFGQGTKLEI KGGGGSGGGG  120
SGGGGSEVQL VQSGAEVKKP GASVKVSCKA SGYTFTDYNM DWVRQAPGQG LEWIGDINPN  180
NGGTLYNQKF RGRVTLTVDT SISTAYMELS RLRSDDTAVY YCARSEVFYG NYADYWGQGT  240
TVTVSS                                                            246

SEQ ID NO: 34          moltype = AA  length = 246
FEATURE                Location/Qualifiers
REGION                 1..246
                       note = 34
source                 1..246
                       mol_type = protein
                       organism = synthetic construct
SEQUENCE: 34
DIVLTQSPDS LAVSLGERAT INCKASQSVD YDGDSYMNWY QQKPGQPPKL LIYAASTLHS  60
GIPDRFSGSG SGTDFTLTIS SLQAEDVAVY YCQQSKEDPR TFGQGTKLEI KGGGGSGGGG  120
SGGGGSEVQL VQSGAEVKKP GASVKVSCKA SGYTFTDYNM DWVRQAPGQG LEWIGDINPN  180
NGGTLYNQKF RGRVTLTVDK SISTAYMELS RLRSDDTAVY YCARSEVFYG NYADYWGQGT  240
TVTVSS                                                            246

SEQ ID NO: 35          moltype = AA  length = 246
FEATURE                Location/Qualifiers
REGION                 1..246
                       note = 35
source                 1..246
                       mol_type = protein
                       organism = synthetic construct
SEQUENCE: 35
DIVLTQSPDS LAVSLGERAT INCKASQSVD YDGDSYMNWY QQKPGQPPKL LIYAASTLHS  60
GIPDRFSGSG SGTDFTLTIS SLQAEDVAVY YCQQSKEDPR TFGQGTKLEI KGGGGSGGGG  120
SGGGGSEVQL VQSGAEVKKP GASVKVSCKA SGYTFTDYNM DWVRQAPGKG LEWIGDINPN  180
NGGTLYNQKF RGRVTLTVDK SISTAYMELS RLRSDDTAVY YCARSEVFYG NYADYWGQGT  240
TVTVSS                                                            246

SEQ ID NO: 36          moltype = AA  length = 246
FEATURE                Location/Qualifiers
REGION                 1..246
                       note = 36
source                 1..246
                       mol_type = protein
                       organism = synthetic construct
SEQUENCE: 36
DIVLTQTPLS LSVTPGQPAS ISCKASQSVD YDGDSYMNWY LQKPGQPPQL LIYAASTLHS  60
GVPDRFSGSG SGTDFTLKIS RVEAEDVGVY YCQQSKEDPR TFGQGTKLEI KGGGGSGGGG  120
SGGGGSEVQL VQSGAEVKKP GASVKVSCKA SGYTFTDYNM DWVRQAPGQG LEWMGDINPN  180
NGGTLYNQKF RGRVTMTVDT SISTAYMELS RLRSDDTAVY YCARSEVFYG NYADYWGQGT  240
TVTVSS                                                            246

SEQ ID NO: 37          moltype = AA  length = 246
FEATURE                Location/Qualifiers
REGION                 1..246
                       note = 37
source                 1..246
                       mol_type = protein
                       organism = synthetic construct
SEQUENCE: 37
```

```
DIVLTQTPLS LSVTPGQPAS ISCKASQSVD YDGDSYMNWY LQKPGQPPQL LIYAASTLHS  60
GVPDRFSGSG SGTDFTLKIS RVEAEDVGVY YCQQSKEDPR TFGQGTKLEI KGGGGSGGGG  120
SGGGGSEVQL VQSGAEVKKP GASVKVSCKA SGYTFTDYNM DWVRQAPGQG LEWIGDINPN  180
NGGTLYNQKF RGRVTLTVDT SISTAYMELS RLRSDDTAVY YCARSEVFYG NYADYWGQGT  240
TVTVSS                                                            246

SEQ ID NO: 38          moltype = AA  length = 246
FEATURE                Location/Qualifiers
REGION                 1..246
                       note = 38
source                 1..246
                       mol_type = protein
                       organism = synthetic construct
SEQUENCE: 38
DIVLTQTPLS LSVTPGQPAS ISCKASQSVD YDGDSYMNWY LQKPGQPPQL LIYAASTLHS  60
GVPDRFSGSG SGTDFTLKIS RVEAEDVGVY YCQQSKEDPR TFGQGTKLEI KGGGGSGGGG  120
SGGGGSEVQL VQSGAEVKKP GASVKVSCKA SGYTFTDYNM DWVRQAPGQG LEWIGDINPN  180
NGGTLYNQKF RGRVTLTVDK SISTAYMELS RLRSDDTAVY YCARSEVFYG NYADYWGQGT  240
TVTVSS                                                            246

SEQ ID NO: 39          moltype = AA  length = 246
FEATURE                Location/Qualifiers
REGION                 1..246
                       note = 39
source                 1..246
                       mol_type = protein
                       organism = synthetic construct
SEQUENCE: 39
DIVLTQTPLS LSVTPGQPAS ISCKASQSVD YDGDSYMNWY LQKPGQPPQL LIYAASTLHS  60
GVPDRFSGSG SGTDFTLKIS RVEAEDVGVY YCQQSKEDPR TFGQGTKLEI KGGGGSGGGG  120
SGGGGSEVQL VQSGAEVKKP GASVKVSCKA SGYTFTDYNM DWVRQAPGKG LEWIGDINPN  180
NGGTLYNQKF RGRVTLTVDK SISTAYMELS RLRSDDTAVY YCARSEVFYG NYADYWGQGT  240
TVTVSS                                                            246

SEQ ID NO: 40          moltype = AA  length = 246
FEATURE                Location/Qualifiers
REGION                 1..246
                       note = 40
source                 1..246
                       mol_type = protein
                       organism = synthetic construct
SEQUENCE: 40
DIVLTQTPLS LSVTPGQPAS ISCKASQSVD YDGDSYMNWY LQKPGQPPQL LIYAASTLHS  60
GIPDRFSGSG SGTDFTLKIS RVEAEDVGVY YCQQSKEDPR TFGQGTKLEI KGGGGSGGGG  120
SGGGGSEVQL VQSGAEVKKP GASVKVSCKA SGYTFTDYNM DWVRQAPGQG LEWMGDINPN  180
NGGTLYNQKF RGRVTMTVDT SISTAYMELS RLRSDDTAVY YCARSEVFYG NYADYWGQGT  240
TVTVSS                                                            246

SEQ ID NO: 41          moltype = AA  length = 246
FEATURE                Location/Qualifiers
REGION                 1..246
                       note = 41
source                 1..246
                       mol_type = protein
                       organism = synthetic construct
SEQUENCE: 41
DIVLTQTPLS LSVTPGQPAS ISCKASQSVD YDGDSYMNWY LQKPGQPPQL LIYAASTLHS  60
GIPDRFSGSG SGTDFTLKIS RVEAEDVGVY YCQQSKEDPR TFGQGTKLEI KGGGGSGGGG  120
SGGGGSEVQL VQSGAEVKKP GASVKVSCKA SGYTFTDYNM DWVRQAPGQG LEWIGDINPN  180
NGGTLYNQKF RGRVTLTVDT SISTAYMELS RLRSDDTAVY YCARSEVFYG NYADYWGQGT  240
TVTVSS                                                            246

SEQ ID NO: 42          moltype = AA  length = 246
FEATURE                Location/Qualifiers
REGION                 1..246
                       note = 42
source                 1..246
                       mol_type = protein
                       organism = synthetic construct
SEQUENCE: 42
DIVLTQTPLS LSVTPGQPAS ISCKASQSVD YDGDSYMNWY LQKPGQPPQL LIYAASTLHS  60
GIPDRFSGSG SGTDFTLKIS RVEAEDVGVY YCQQSKEDPR TFGQGTKLEI KGGGGSGGGG  120
SGGGGSEVQL VQSGAEVKKP GASVKVSCKA SGYTFTDYNM DWVRQAPGQG LEWIGDINPN  180
NGGTLYNQKF RGRVTLTVDK SISTAYMELS RLRSDDTAVY YCARSEVFYG NYADYWGQGT  240
TVTVSS                                                            246

SEQ ID NO: 43          moltype = AA  length = 246
FEATURE                Location/Qualifiers
REGION                 1..246
```

```
                         note = 43
source                   1..246
                         mol_type = protein
                         organism = synthetic construct
SEQUENCE: 43
DIVLTQTPLS LSVTPGQPAS ISCKASQSVD YDGDSYMNWY LQKPGQPPQL LIYAASTLHS  60
GIPDRFSGSG SGTDFTLKIS RVEAEDVGVY YCQQSKEDPR TFGQGTKLEI KGGGGSGGGG  120
SGGGGSEVQL VQSGAEVKKP GASVKVSCKA SGYTFTDYNM DWVRQAPGKG LEWIGDINPN  180
NGGTLYNQKF RGRVTLTVDK SISTAYMELS RLRSDDTAVY YCARSEVFYG NYADYWGQGT  240
TVTVSS                                                             246

SEQ ID NO: 44            moltype = AA  length = 246
FEATURE                  Location/Qualifiers
REGION                   1..246
                         note = 44
source                   1..246
                         mol_type = protein
                         organism = synthetic construct
SEQUENCE: 44
DIVLTQSPVS LAVPLGQRAT ISCKASQSVD YDGDSYMNWY QQKPGQPPKL LIYAASTLHS  60
GIPVRFSGSG SGTDFTLNIH PVEEEDAASY YCQQSKEDPR TFGGGTKLEI KGGGGSGGGG  120
SGGGGSEVLL QQSGPEVVKP GASVKITCKA SGYTFTDYNM DWVKQSHGKS LEWIGDINPN  180
NAGTLYNQKF RGRVTLIVDK SSSTAYMELR SLTSDDTAVY YCARSEVFYG NYADYWGQGT  240
TLTVSS                                                             246

SEQ ID NO: 45            moltype = AA  length = 246
FEATURE                  Location/Qualifiers
REGION                   1..246
                         note = 45
source                   1..246
                         mol_type = protein
                         organism = synthetic construct
SEQUENCE: 45
DIVLTQSPVS LAVPLGQRAT ISCKASQSVD YDADSYMNWY QQKPGQPPKL LIYAASTLHS  60
GIPVRFSGSG SGTDFTLNIH PVEEEDAASY YCQQSKEDPR TFGGGTKLEI KGGGGSGGGG  120
SGGGGSEVLL QQSGPEVVKP GASVKITCKA SGYTFTDYNM DWVKQSHGKS LEWIGDINPN  180
NGGTLYNQKF RGRVTLIVDK SSSTAYMELR SLTSDDTAVY YCARSEVFYG NYADYWGQGT  240
TLTVSS                                                             246

SEQ ID NO: 46            moltype = AA  length = 15
FEATURE                  Location/Qualifiers
REGION                   1..15
                         note = 46
source                   1..15
                         mol_type = protein
                         organism = synthetic construct
SEQUENCE: 46
GGGGSGGGGS GGGGS                                                   15

SEQ ID NO: 47            moltype = AA  length = 232
FEATURE                  Location/Qualifiers
REGION                   1..232
                         note = 47
source                   1..232
                         mol_type = protein
                         organism = synthetic construct
SEQUENCE: 47
EPKSCDKTHT CPPCPAPEAA GGPSVFLFPP KPKDTLMISR TPEVTCVVVD VSHEDPEVKF  60
NWYVDGVEVH NAKTKPREEQ YNSTYRVVSV LTVLHQDWLN GKEYKCKVSN KALPAPIEKT  120
ISKAKGQPRE PQVYTLPPCR DELTKNQVSL WCLVKGFYPS DIAVEWESNG QPENNYKTTP  180
PVLDSDGSFF LYSKLTVDKS RWQQGNVFSC SVMHEALHNH YTQKSLSLSP GK          232

SEQ ID NO: 48            moltype = AA  length = 232
FEATURE                  Location/Qualifiers
REGION                   1..232
                         note = 48
source                   1..232
                         mol_type = protein
                         organism = synthetic construct
SEQUENCE: 48
EPKSCDKTHT CPPCPAPEAA GGPSVFLFPP KPKDTLMISR TPEVTCVVVD VSHEDPEVKF  60
NWYVDGVEVH NAKTKPREEQ YNSTYRVVSV LTVLHQDWLN GKEYKCKVSN KALPAPIEKT  120
ISKAKGQPRE PQVCTLPPSR DELTKNQVSL SCAVKGFYPS DIAVEWESNG QPENNYKTTP  180
PVLDSDGSFF LVSKLTVDKS RWQQGNVFSC SVMHEALHNH YTQKSLSLSP GK          232

SEQ ID NO: 49            moltype = AA  length = 477
FEATURE                  Location/Qualifiers
REGION                   1..477
                         note = 49
```

```
source                  1..477
                        mol_type = protein
                        organism = synthetic construct
SEQUENCE: 49
MDIQMTQSPS SLSASVGDRV TITCRASQDI RNYLNWYQQK PGKAPKLLIY YTSRLESGVP  60
SRFSGSGSGT DYTLTISSLQ PEDFATYYCQ QGNTLPWTFG QGTKVEIKGG GGSGGGGSGG  120
GGSEVQLVES GGGLVQPGGS LRLSCAASGY SFTGYTMNWV RQAPGKGLEW VALINPYKGV  180
STYNQKFKDR FTISVDKSKN TAYLQMNSLR AEDTAVYYCA RSGYYGDSDW YFDVWGQGTL  240
VTVSSEPKSC DKTHTCPPCP APEAAGGPSV FLFPPKPKDT LMISRTPEVT CVVVDVSHED  300
PEVKFNWYVD GVEVHNAKTK PREEQYNSTY RVVSVLTVLH QDWLNGKEYK CKVSNKALPA  360
PIEKTISKAK GQPREPQVYT LPPCRDELTK NQVSLWCLVK GFYPSDIAVE WESNGQPENN  420
YKTTPPVLDS DGSFFLYSKL TVDKSRWQQG NVFSCSVMHE ALHNHYTQKS LSLSPGK     477

SEQ ID NO: 50           moltype = AA  length = 478
FEATURE                 Location/Qualifiers
REGION                  1..478
                        note = 50
source                  1..478
                        mol_type = protein
                        organism = synthetic construct
SEQUENCE: 50
DIVLTQSPDS LAVSLGERAT INCKASQSVD YDGDSYMNWY QQKPGQPPKL LIYAASTLHS  60
GVPDRFSGSG SGTDFTLTIS SLQAEDVAVY YCQQSKEDPR TFGQGTKLEI KGGGGSGGGG  120
SGGGGSEVQL VQSGAEVKKP GASVKVSCKA SGYTFTDYNM DWVRQAPGQG LEWMGDINPN  180
NGGTLYNQKF RGRVTMTVDT SISTAYMELS RLRSDDTAVY YCARSEVFYG NYADYWGQGT  240
TVTVSSEPKS CDKTHTCPPC PAPEAAGGPS VFLFPPKPKD TLMISRTPEV TCVVVDVSHE  300
DPEVKFNWYV DGVEVHNAKT KPREEQYNST YRVVSVLTVL HQDWLNGKEY KCKVSNKALP  360
APIEKTISKA KGQPREPQVC TLPPSRDELT KNQVSLSCAV KGFYPSDIAV EWESNGQPEN  420
NYKTTPPVLD SDGSFFLVSK LTVDKSRWQQ GNVFSCSVMH EALHNHYTQK SLSLSPGK    478

SEQ ID NO: 51           moltype = AA  length = 478
FEATURE                 Location/Qualifiers
REGION                  1..478
                        note = 51
source                  1..478
                        mol_type = protein
                        organism = synthetic construct
SEQUENCE: 51
DIVLTQSPDS LAVSLGERAT INCKASQSVD YDGDSYMNWY QQKPGQPPKL LIYAASTLHS  60
GVPDRFSGSG SGTDFTLTIS SLQAEDVAVY YCQQSKEDPR TFGQGTKLEI KGGGGSGGGG  120
SGGGGSEVQL VQSGAEVKKP GASVKVSCKA SGYTFTDYNM DWVRQAPGQG LEWIGDINPN  180
NGGTLYNQKF RGRVTLTVDT SISTAYMELS RLRSDDTAVY YCARSEVFYG NYADYWGQGT  240
TVTVSSEPKS CDKTHTCPPC PAPEAAGGPS VFLFPPKPKD TLMISRTPEV TCVVVDVSHE  300
DPEVKFNWYV DGVEVHNAKT KPREEQYNST YRVVSVLTVL HQDWLNGKEY KCKVSNKALP  360
APIEKTISKA KGQPREPQVC TLPPSRDELT KNQVSLSCAV KGFYPSDIAV EWESNGQPEN  420
NYKTTPPVLD SDGSFFLVSK LTVDKSRWQQ GNVFSCSVMH EALHNHYTQK SLSLSPGK    478

SEQ ID NO: 52           moltype = AA  length = 478
FEATURE                 Location/Qualifiers
REGION                  1..478
                        note = 52
source                  1..478
                        mol_type = protein
                        organism = synthetic construct
SEQUENCE: 52
DIVLTQSPDS LAVSLGERAT INCKASQSVD YDGDSYMNWY QQKPGQPPKL LIYAASTLHS  60
GVPDRFSGSG SGTDFTLTIS SLQAEDVAVY YCQQSKEDPR TFGQGTKLEI KGGGGSGGGG  120
SGGGGSEVQL VQSGAEVKKP GASVKVSCKA SGYTFTDYNM DWVRQAPGQG LEWIGDINPN  180
NGGTLYNQKF RGRVTLTVDK SISTAYMELS RLRSDDTAVY YCARSEVFYG NYADYWGQGT  240
TVTVSSEPKS CDKTHTCPPC PAPEAAGGPS VFLFPPKPKD TLMISRTPEV TCVVVDVSHE  300
DPEVKFNWYV DGVEVHNAKT KPREEQYNST YRVVSVLTVL HQDWLNGKEY KCKVSNKALP  360
APIEKTISKA KGQPREPQVC TLPPSRDELT KNQVSLSCAV KGFYPSDIAV EWESNGQPEN  420
NYKTTPPVLD SDGSFFLVSK LTVDKSRWQQ GNVFSCSVMH EALHNHYTQK SLSLSPGK    478

SEQ ID NO: 53           moltype = AA  length = 478
FEATURE                 Location/Qualifiers
REGION                  1..478
                        note = 53
source                  1..478
                        mol_type = protein
                        organism = synthetic construct
SEQUENCE: 53
DIVLTQSPDS LAVSLGERAT INCKASQSVD YDGDSYMNWY QQKPGQPPKL LIYAASTLHS  60
GVPDRFSGSG SGTDFTLTIS SLQAEDVAVY YCQQSKEDPR TFGQGTKLEI KGGGGSGGGG  120
SGGGGSEVQL VQSGAEVKKP GASVKVSCKA SGYTFTDYNM DWVRQAPGKG LEWIGDINPN  180
NGGTLYNQKF RGRVTLTVDK SISTAYMELS RLRSDDTAVY YCARSEVFYG NYADYWGQGT  240
TVTVSSEPKS CDKTHTCPPC PAPEAAGGPS VFLFPPKPKD TLMISRTPEV TCVVVDVSHE  300
DPEVKFNWYV DGVEVHNAKT KPREEQYNST YRVVSVLTVL HQDWLNGKEY KCKVSNKALP  360
APIEKTISKA KGQPREPQVC TLPPSRDELT KNQVSLSCAV KGFYPSDIAV EWESNGQPEN  420
```

```
NYKTTPPVLD SDGSFFLVSK LTVDKSRWQQ GNVFSCSVMH EALHNHYTQK SLSLSPGK    478

SEQ ID NO: 54          moltype = AA  length = 478
FEATURE                Location/Qualifiers
REGION                 1..478
                       note = 54
source                 1..478
                       mol_type = protein
                       organism = synthetic construct
SEQUENCE: 54
DIVLTQSPDS LAVSLGERAT INCKASQSVD YDGDSYMNWY QQKPGQPPKL LIYAASTLHS  60
GIPDRFSGSG SGTDFTLTIS SLQAEDVAVY YCQQSKEDPR TFGQGTKLEI KGGGGSGGGG  120
SGGGGSEVQL VQSGAEVKKP GASVKVSCKA SGYTFTDYNM DWVRQAPGQG LEWMGDINPN  180
NGGTLYNQKF RGRVTMTVDT SISTAYMELS RLRSDDTAVY YCARSEVFYG NYADYWGQGT  240
TVTVSSEPKS CDKTHTCPPC PAPEAAGGPS VFLFPPKPKD TLMISRTPEV TCVVVDVSHE  300
DPEVKFNWYV DGVEVHNAKT KPREEQYNST YRVVSVLTVL HQDWLNGKEY KCKVSNKALP  360
APIEKTISKA KGQPREPQVC TLPPSRDELT KNQVSLSCAV KGFYPSDIAV EWESNGQPEN  420
NYKTTPPVLD SDGSFFLVSK LTVDKSRWQQ GNVFSCSVMH EALHNHYTQK SLSLSPGK    478

SEQ ID NO: 55          moltype = AA  length = 478
FEATURE                Location/Qualifiers
REGION                 1..478
                       note = 55
source                 1..478
                       mol_type = protein
                       organism = synthetic construct
SEQUENCE: 55
DIVLTQSPDS LAVSLGERAT INCKASQSVD YDGDSYMNWY QQKPGQPPKL LIYAASTLHS  60
GIPDRFSGSG SGTDFTLTIS SLQAEDVAVY YCQQSKEDPR TFGQGTKLEI KGGGGSGGGG  120
SGGGGSEVQL VQSGAEVKKP GASVKVSCKA SGYTFTDYNM DWVRQAPGQG LEWIGDINPN  180
NGGTLYNQKF RGRVTLTVDT SISTAYMELS RLRSDDTAVY YCARSEVFYG NYADYWGQGT  240
TVTVSSEPKS CDKTHTCPPC PAPEAAGGPS VFLFPPKPKD TLMISRTPEV TCVVVDVSHE  300
DPEVKFNWYV DGVEVHNAKT KPREEQYNST YRVVSVLTVL HQDWLNGKEY KCKVSNKALP  360
APIEKTISKA KGQPREPQVC TLPPSRDELT KNQVSLSCAV KGFYPSDIAV EWESNGQPEN  420
NYKTTPPVLD SDGSFFLVSK LTVDKSRWQQ GNVFSCSVMH EALHNHYTQK SLSLSPGK    478

SEQ ID NO: 56          moltype = AA  length = 478
FEATURE                Location/Qualifiers
REGION                 1..478
                       note = 56
source                 1..478
                       mol_type = protein
                       organism = synthetic construct
SEQUENCE: 56
DIVLTQSPDS LAVSLGERAT INCKASQSVD YDGDSYMNWY QQKPGQPPKL LIYAASTLHS  60
GIPDRFSGSG SGTDFTLTIS SLQAEDVAVY YCQQSKEDPR TFGQGTKLEI KGGGGSGGGG  120
SGGGGSEVQL VQSGAEVKKP GASVKVSCKA SGYTFTDYNM DWVRQAPGQG LEWIGDINPN  180
NGGTLYNQKF RGRVTLTVDK SISTAYMELS RLRSDDTAVY YCARSEVFYG NYADYWGQGT  240
TVTVSSEPKS CDKTHTCPPC PAPEAAGGPS VFLFPPKPKD TLMISRTPEV TCVVVDVSHE  300
DPEVKFNWYV DGVEVHNAKT KPREEQYNST YRVVSVLTVL HQDWLNGKEY KCKVSNKALP  360
APIEKTISKA KGQPREPQVC TLPPSRDELT KNQVSLSCAV KGFYPSDIAV EWESNGQPEN  420
NYKTTPPVLD SDGSFFLVSK LTVDKSRWQQ GNVFSCSVMH EALHNHYTQK SLSLSPGK    478

SEQ ID NO: 57          moltype = AA  length = 478
FEATURE                Location/Qualifiers
REGION                 1..478
                       note = 57
source                 1..478
                       mol_type = protein
                       organism = synthetic construct
SEQUENCE: 57
DIVLTQSPDS LAVSLGERAT INCKASQSVD YDGDSYMNWY QQKPGQPPKL LIYAASTLHS  60
GIPDRFSGSG SGTDFTLTIS SLQAEDVAVY YCQQSKEDPR TFGQGTKLEI KGGGGSGGGG  120
SGGGGSEVQL VQSGAEVKKP GASVKVSCKA SGYTFTDYNM DWVRQAPGKG LEWIGDINPN  180
NGGTLYNQKF RGRVTLTVDK SISTAYMELS RLRSDDTAVY YCARSEVFYG NYADYWGQGT  240
TVTVSSEPKS CDKTHTCPPC PAPEAAGGPS VFLFPPKPKD TLMISRTPEV TCVVVDVSHE  300
DPEVKFNWYV DGVEVHNAKT KPREEQYNST YRVVSVLTVL HQDWLNGKEY KCKVSNKALP  360
APIEKTISKA KGQPREPQVC TLPPSRDELT KNQVSLSCAV KGFYPSDIAV EWESNGQPEN  420
NYKTTPPVLD SDGSFFLVSK LTVDKSRWQQ GNVFSCSVMH EALHNHYTQK SLSLSPGK    478

SEQ ID NO: 58          moltype = AA  length = 478
FEATURE                Location/Qualifiers
REGION                 1..478
                       note = 58
source                 1..478
                       mol_type = protein
                       organism = synthetic construct
SEQUENCE: 58
DIVLTQTPLS LSVTPGQPAS ISCKASQSVD YDGDSYMNWY LQKPGQPPQL LIYAASTLHS  60
```

```
GVPDRFSGSG SGTDFTLKIS RVEAEDVGVY YCQQSKEDPR TFGQGTKLEI KGGGGSGGGG  120
SGGGGSEVQL VQSGAEVKKP GASVKVSCKA SGYTFTDYNM DWVRQAPGQG LEWMGDINPN  180
NGGTLYNQKF RGRVTMTVDT SISTAYMELS RLRSDDTAVY YCARSEVFYG NYADYWGQGT  240
TVTVSSEPKS CDKTHTCPPC PAPEAAGGPS VFLFPPKPKD TLMISRTPEV TCVVVDVSHE  300
DPEVKFNWYV DGVEVHNAKT KPREEQYNST YRVVSVLTVL HQDWLNGKEY KCKVSNKALP  360
APIEKTISKA KGQPREPQVC TLPPSRDELT KNQVSLSCAV KGFYPSDIAV EWESNGQPEN  420
NYKTTPPVLD SDGSFFLVSK LTVDKSRWQQ GNVFSCSVMH EALHNHYTQK SLSLSPGK    478

SEQ ID NO: 59          moltype = AA  length = 478
FEATURE                Location/Qualifiers
REGION                 1..478
                       note = 59
source                 1..478
                       mol_type = protein
                       organism = synthetic construct
SEQUENCE: 59
DIVLTQTPLS LSVTPGQPAS ISCKASQSVD YDGDSYMNWY LQKPGQPPQL LIYAASTLHS  60
GVPDRFSGSG SGTDFTLKIS RVEAEDVGVY YCQQSKEDPR TFGQGTKLEI KGGGGSGGGG  120
SGGGGSEVQL VQSGAEVKKP GASVKVSCKA SGYTFTDYNM DWVRQAPGQG LEWIGDINPN  180
NGGTLYNQKF RGRVTLTVDT SISTAYMELS RLRSDDTAVY YCARSEVFYG NYADYWGQGT  240
TVTVSSEPKS CDKTHTCPPC PAPEAAGGPS VFLFPPKPKD TLMISRTPEV TCVVVDVSHE  300
DPEVKFNWYV DGVEVHNAKT KPREEQYNST YRVVSVLTVL HQDWLNGKEY KCKVSNKALP  360
APIEKTISKA KGQPREPQVC TLPPSRDELT KNQVSLSCAV KGFYPSDIAV EWESNGQPEN  420
NYKTTPPVLD SDGSFFLVSK LTVDKSRWQQ GNVFSCSVMH EALHNHYTQK SLSLSPGK    478

SEQ ID NO: 60          moltype = AA  length = 478
FEATURE                Location/Qualifiers
REGION                 1..478
                       note = 60
source                 1..478
                       mol_type = protein
                       organism = synthetic construct
SEQUENCE: 60
DIVLTQTPLS LSVTPGQPAS ISCKASQSVD YDGDSYMNWY LQKPGQPPQL LIYAASTLHS  60
GVPDRFSGSG SGTDFTLKIS RVEAEDVGVY YCQQSKEDPR TFGQGTKLEI KGGGGSGGGG  120
SGGGGSEVQL VQSGAEVKKP GASVKVSCKA SGYTFTDYNM DWVRQAPGQG LEWIGDINPN  180
NGGTLYNQKF RGRVTLTVDK SISTAYMELS RLRSDDTAVY YCARSEVFYG NYADYWGQGT  240
TVTVSSEPKS CDKTHTCPPC PAPEAAGGPS VFLFPPKPKD TLMISRTPEV TCVVVDVSHE  300
DPEVKFNWYV DGVEVHNAKT KPREEQYNST YRVVSVLTVL HQDWLNGKEY KCKVSNKALP  360
APIEKTISKA KGQPREPQVC TLPPSRDELT KNQVSLSCAV KGFYPSDIAV EWESNGQPEN  420
NYKTTPPVLD SDGSFFLVSK LTVDKSRWQQ GNVFSCSVMH EALHNHYTQK SLSLSPGK    478

SEQ ID NO: 61          moltype = AA  length = 478
FEATURE                Location/Qualifiers
REGION                 1..478
                       note = 61
source                 1..478
                       mol_type = protein
                       organism = synthetic construct
SEQUENCE: 61
DIVLTQTPLS LSVTPGQPAS ISCKASQSVD YDGDSYMNWY LQKPGQPPQL LIYAASTLHS  60
GVPDRFSGSG SGTDFTLKIS RVEAEDVGVY YCQQSKEDPR TFGQGTKLEI KGGGGSGGGG  120
SGGGGSEVQL VQSGAEVKKP GASVKVSCKA SGYTFTDYNM DWVRQAPGKG LEWIGDINPN  180
NGGTLYNQKF RGRVTLTVDK SISTAYMELS RLRSDDTAVY YCARSEVFYG NYADYWGQGT  240
TVTVSSEPKS CDKTHTCPPC PAPEAAGGPS VFLFPPKPKD TLMISRTPEV TCVVVDVSHE  300
DPEVKFNWYV DGVEVHNAKT KPREEQYNST YRVVSVLTVL HQDWLNGKEY KCKVSNKALP  360
APIEKTISKA KGQPREPQVC TLPPSRDELT KNQVSLSCAV KGFYPSDIAV EWESNGQPEN  420
NYKTTPPVLD SDGSFFLVSK LTVDKSRWQQ GNVFSCSVMH EALHNHYTQK SLSLSPGK    478

SEQ ID NO: 62          moltype = AA  length = 478
FEATURE                Location/Qualifiers
REGION                 1..478
                       note = 62
source                 1..478
                       mol_type = protein
                       organism = synthetic construct
SEQUENCE: 62
DIVLTQTPLS LSVTPGQPAS ISCKASQSVD YDGDSYMNWY LQKPGQPPQL LIYAASTLHS  60
GIPDRFSGSG SGTDFTLKIS RVEAEDVGVY YCQQSKEDPR TFGQGTKLEI KGGGGSGGGG  120
SGGGGSEVQL VQSGAEVKKP GASVKVSCKA SGYTFTDYNM DWVRQAPGQG LEWMGDINPN  180
NGGTLYNQKF RGRVTMTVDT SISTAYMELS RLRSDDTAVY YCARSEVFYG NYADYWGQGT  240
TVTVSSEPKS CDKTHTCPPC PAPEAAGGPS VFLFPPKPKD TLMISRTPEV TCVVVDVSHE  300
DPEVKFNWYV DGVEVHNAKT KPREEQYNST YRVVSVLTVL HQDWLNGKEY KCKVSNKALP  360
APIEKTISKA KGQPREPQVC TLPPSRDELT KNQVSLSCAV KGFYPSDIAV EWESNGQPEN  420
NYKTTPPVLD SDGSFFLVSK LTVDKSRWQQ GNVFSCSVMH EALHNHYTQK SLSLSPGK    478

SEQ ID NO: 63          moltype = AA  length = 478
FEATURE                Location/Qualifiers
REGION                 1..478
```

```
                          note = 63
source                    1..478
                          mol_type = protein
                          organism = synthetic construct
SEQUENCE: 63
DIVLTQTPLS LSVTPGQPAS ISCKASQSVD YDGDSYMNWY LQKPGQPPQL LIYAASTLHS  60
GIPDRFSGSG SGTDFTLKIS RVEAEDVGVY YCQQSKEDPR TFGQGTKLEI KGGGGSGGGG  120
SGGGGSEVQL VQSGAEVKKP GASVKVSCKA SGYTFTDYNM DWVRQAPGQG LEWIGDINPN  180
NGGTLYNQKF RGRVTLTVDT SISTAYMELS RLRSDDTAVY YCARSEVFYG NYADYWGQGT  240
TVTVSSEPKS CDKTHTCPPC PAPEAAGGPS VFLFPPKPKD TLMISRTPEV TCVVVDVSHE  300
DPEVKFNWYV DGVEVHNAKT KPREEQYNST YRVVSVLTVL HQDWLNGKEY KCKVSNKALP  360
APIEKTISKA KGQPREPQVC TLPPSRDELT KNQVSLSCAV KGFYPSDIAV EWESNGQPEN  420
NYKTTPPVLD SDGSFFLVSK LTVDKSRWQQ GNVFSCSVMH EALHNHYTQK SLSLSPGK    478

SEQ ID NO: 64             moltype = AA  length = 478
FEATURE                   Location/Qualifiers
REGION                    1..478
                          note = 64
source                    1..478
                          mol_type = protein
                          organism = synthetic construct
SEQUENCE: 64
DIVLTQTPLS LSVTPGQPAS ISCKASQSVD YDGDSYMNWY LQKPGQPPQL LIYAASTLHS  60
GIPDRFSGSG SGTDFTLKIS RVEAEDVGVY YCQQSKEDPR TFGQGTKLEI KGGGGSGGGG  120
SGGGGSEVQL VQSGAEVKKP GASVKVSCKA SGYTFTDYNM DWVRQAPGQG LEWIGDINPN  180
NGGTLYNQKF RGRVTLTVDK SISTAYMELS RLRSDDTAVY YCARSEVFYG NYADYWGQGT  240
TVTVSSEPKS CDKTHTCPPC PAPEAAGGPS VFLFPPKPKD TLMISRTPEV TCVVVDVSHE  300
DPEVKFNWYV DGVEVHNAKT KPREEQYNST YRVVSVLTVL HQDWLNGKEY KCKVSNKALP  360
APIEKTISKA KGQPREPQVC TLPPSRDELT KNQVSLSCAV KGFYPSDIAV EWESNGQPEN  420
NYKTTPPVLD SDGSFFLVSK LTVDKSRWQQ GNVFSCSVMH EALHNHYTQK SLSLSPGK    478

SEQ ID NO: 65             moltype = AA  length = 478
FEATURE                   Location/Qualifiers
REGION                    1..478
                          note = 65
source                    1..478
                          mol_type = protein
                          organism = synthetic construct
SEQUENCE: 65
DIVLTQTPLS LSVTPGQPAS ISCKASQSVD YDGDSYMNWY LQKPGQPPQL LIYAASTLHS  60
GIPDRFSGSG SGTDFTLKIS RVEAEDVGVY YCQQSKEDPR TFGQGTKLEI KGGGGSGGGG  120
SGGGGSEVQL VQSGAEVKKP GASVKVSCKA SGYTFTDYNM DWVRQAPGKG LEWIGDINPN  180
NGGTLYNQKF RGRVTLTVDK SISTAYMELS RLRSDDTAVY YCARSEVFYG NYADYWGQGT  240
TVTVSSEPKS CDKTHTCPPC PAPEAAGGPS VFLFPPKPKD TLMISRTPEV TCVVVDVSHE  300
DPEVKFNWYV DGVEVHNAKT KPREEQYNST YRVVSVLTVL HQDWLNGKEY KCKVSNKALP  360
APIEKTISKA KGQPREPQVC TLPPSRDELT KNQVSLSCAV KGFYPSDIAV EWESNGQPEN  420
NYKTTPPVLD SDGSFFLVSK LTVDKSRWQQ GNVFSCSVMH EALHNHYTQK SLSLSPGK    478

SEQ ID NO: 66             moltype = AA  length = 478
FEATURE                   Location/Qualifiers
REGION                    1..478
                          note = 66
source                    1..478
                          mol_type = protein
                          organism = synthetic construct
SEQUENCE: 66
DIVLTQSPVS LAVPLGQRAT ISCKASQSVD YDGDSYMNWY QQKPGQPPKL LIYAASTLHS  60
GIPVRFSGSG SGTDFTLNIH PVEEEDAASY YCQQSKEDPR TFGGGTKLEI KGGGGSGGGG  120
SGGGGSEVLL QQSGPEVVKP GASVKITCKA SGYTFTDYNM DWVKQSHGKS LEWIGDINPN  180
NAGTLYNQKF RGRVTLIVDK SSSTAYMELR SLTSDDTAVY YCARSEVFYG NYADYWGQGT  240
TLTVSSEPKS CDKTHTCPPC PAPEAAGGPS VFLFPPKPKD TLMISRTPEV TCVVVDVSHE  300
DPEVKFNWYV DGVEVHNAKT KPREEQYNST YRVVSVLTVL HQDWLNGKEY KCKVSNKALP  360
APIEKTISKA KGQPREPQVC TLPPSRDELT KNQVSLSCAV KGFYPSDIAV EWESNGQPEN  420
NYKTTPPVLD SDGSFFLVSK LTVDKSRWQQ GNVFSCSVMH EALHNHYTQK SLSLSPGK    478

SEQ ID NO: 67             moltype = AA  length = 478
FEATURE                   Location/Qualifiers
REGION                    1..478
                          note = 67
source                    1..478
                          mol_type = protein
                          organism = synthetic construct
SEQUENCE: 67
DIVLTQSPVS LAVPLGQRAT ISCKASQSVD YDADSYMNWY QQKPGQPPKL LIYAASTLHS  60
GIPVRFSGSG SGTDFTLNIH PVEEEDAASY YCQQSKEDPR TFGGGTKLEI KGGGGSGGGG  120
SGGGGSEVLL QQSGPEVVKP GASVKITCKA SGYTFTDYNM DWVKQSHGKS LEWIGDINPN  180
NGGTLYNQKF RGRVTLIVDK SSSTAYMELR SLTSDDTAVY YCARSEVFYG NYADYWGQGT  240
TLTVSSEPKS CDKTHTCPPC PAPEAAGGPS VFLFPPKPKD TLMISRTPEV TCVVVDVSHE  300
DPEVKFNWYV DGVEVHNAKT KPREEQYNST YRVVSVLTVL HQDWLNGKEY KCKVSNKALP  360
```

```
APIEKTISKA KGQPREPQVC TLPPSRDELT KNQVSLSCAV KGFYPSDIAV EWESNGQPEN  420
NYKTTPPVLD SDGSFFLVSK LTVDKSRWQQ GNVFSCSVMH EALHNHYTQK SLSLSPGK    478

SEQ ID NO: 68          moltype = AA  length = 20
FEATURE                Location/Qualifiers
REGION                 1..20
                       note = 68
source                 1..20
                       mol_type = protein
                       organism = synthetic construct
SEQUENCE: 68
METDTLLLWV LLLWVPGSTG                                              20

SEQ ID NO: 69          moltype = DNA  length = 1449
FEATURE                Location/Qualifiers
misc_feature           1..1449
                       note = 69
source                 1..1449
                       mol_type = other DNA
                       organism = synthetic construct
SEQUENCE: 69
caggccgtgg tgacccagga gccctccctg accgtgtccc ccggcggcac cgtgaccctg  60
acctgcaggt cctccaccgg cgccgtgacc acctccaact acgccaactg ggtgcagcag  120
aagcccggcc aggcccccag gggcctgatc ggcggcacca acaagagggc cccctggacc  180
cccgccaggt tctccggctc cctgctgggc ggcaaggccg ccctgaccat caccggcgcc  240
caggccgagg acgaggccga ctactactgc gccctgtggt actccaacct gtgggtgttc  300
ggcggcggca ccaagctgac cgtgctgggc ggaggcggtg gatcaggcgg aggtggctca  360
ggtggaggcg gttctgaggt gcagctggtg gagtccggcg gcggcctggt gcagcccggc  420
ggctccctga ggctgtcctg cgccgcctcc ggcttcacct tcaacaccta cgccatgaac  480
tgggtgaggc aggcccccgg caagggcctg gagtgggtgg ccaggatcag gtccaagtac  540
aacaactacg ccacctacta cgccgactcc gtgaaggaca ggttcaccat ctccagggac  600
gactccaaga actccctgta cctgcagatg aactccctga agaccgagga caccgccgtg  660
tactactgcg tgaggcacgg caacttcggc aactcctacg tgtcctggtt cgcctactgg  720
ggccagggca ccctggtgac cgtgtcctcc gagcccaagt cctgcgacaa gacccacacc  780
tgccccccct gccccgcccc cgaggccgcc ggcggcccct ccgtgttcct gttccccccc  840
aagcccaagg acaccctgat gatctccagg acccccgagg tgacctgcgt ggtggtggac  900
gtgtcccacg aggaccccga ggtgaagttc aactggtacg tggacggcgt ggaggtgcac  960
aacgccaaga ccaagcccag ggaggagcag tacaactcca cctacagggt ggtgtccgtg  1020
ctgaccgtgc tgcaccagga ctggctgaac ggcaaggagt acaagtgcaa ggtgtccaac  1080
aaggccctgc ccgcccccat cgagaagacc atctccaagg ccaagggcca gcccagggag  1140
ccccaggtgt acaccctgcc cccctgcagg gacgagctga ccaagaacca ggtgtccctg  1200
tggtgcctgg tgaagggctt ctaccccctcc gacatcgccg tggagtggga gtccaacggc  1260
cagcccgaga acaactacaa gaccaccccc cccgtgctgg actccgacgg ctccttcttc  1320
ctgtactcca agctgaccgt ggacaagtcc aggtggcagc agggcaacgt gttctcctgc  1380
tccgtgatgc acgaggccct gcacaaccac tacacccaga agtccctgtc cctgtccccc  1440
ggcaagtaa                                                          1449

SEQ ID NO: 70          moltype = DNA  length = 1437
FEATURE                Location/Qualifiers
misc_feature           1..1437
                       note = 70
source                 1..1437
                       mol_type = other DNA
                       organism = synthetic construct
SEQUENCE: 70
gacatcgtgc tgacccagtc ccccgactcc ctggccgtgt ccctgggcga gagggccacc  60
atcaactgca aggcctccca gtccgtggac tacgacggcg actcctacat gaactggtac  120
cagcagaagc ccggccagcc ccccaagctg ctgatctacg ccgcctccac cctgcactcc  180
ggcgtgcccg acaggttctc cggctccggc tccggcaccg acttcaccct gaccatctcc  240
tccctgcagg ccgaggacgt ggccgtgtac tactgccagc agtccaagga ggaccccagg  300
accttcggcc agggcaccaa gctggagatc aagggaggcg gtggatcagg cggaggtggc  360
tcaggtggag gcggttctga ggtgcagctg gtgcagtccg gcgccgaggt gaagaagccc  420
ggcgcctccg tgaaggtgtc ctgcaaggcc tccggctaca ccttcaccga ctacaacatg  480
gactgggtga ggcaggcccc cggccagggc ctggagtgga tgggcgacat caaccccaac  540
aacggcggca ccctgtacaa ccagaagttc aggggcaggg tgaccatgac cgtggacacc  600
tccatctcca ccgcctacat ggagctgtcc aggctgaggt ccgacgacac cgccgtgtac  660
tactgcgcca ggtccgaggt gttctacggc aactacgccg actactgggg ccagggcacc  720
accgtgaccg tgtcctccga gcccaagtcc tgcgacaaga cccacacctg cccccccctgc  780
cccgcccccg aggccgccgg cggcccctcc gtgttcctgt tcccccccaa gcccaaggac  840
accctgatga tctccaggac ccccgaggtg acctgcgtgg tggtggacgt gtcccacgag  900
gaccccgagg tgaagttcaa ctggtacgtg gacggcgtgg aggtgcacaa cgccaagacc  960
aagcccaggg aggagcagta caactccacc tacagggtgg tgtccgtgct gaccgtgctg  1020
caccaggact ggctgaacgg caaggagtac aagtgcaagg tgtccaacaa ggccctgccc  1080
gcccccatcg agaagaccat ctccaaggcc aagggccagc ccagggagcc ccaggtgtgc  1140
accctgcccc cctccaggga cgagctgacc aagaaccagg tgtccctgtc ctgcgccgtg  1200
aagggcttct acccctccga catcgccgtg gagtgggagt ccaacggcca gcccgagaac  1260
aactacaaga ccaccccccc cgtgctggac tccgacggct ccttcttcct ggtgtccaag  1320
ctgaccgtgg acaagtccag gtggcagcag ggcaacgtgt tctcctgctc cgtgatgcac  1380
gaggccctgc acaaccacta cacccagaag tccctgtccc tgtcccccgg caagtaa     1437
```

```
SEQ ID NO: 71          moltype = DNA  length = 1437
FEATURE                Location/Qualifiers
misc_feature           1..1437
                       note = 71
source                 1..1437
                       mol_type = other DNA
                       organism = synthetic construct
SEQUENCE: 71
gacatcgtgc tgacccagtc ccccgactcc ctggccgtgt ccctgggcga gagggccacc  60
atcaactgca aggcctccca gtccgtggac tacgacggcg actcctacat gaactggtac  120
cagcagaagc ccggccagcc ccccaagctg ctgatctacg ccgcctccac cctgcactcc  180
ggcgtgcccg acaggttctc cggctccggc tccggcaccg acttcaccct gaccatctcc  240
tccctgcagg ccgaggacgt ggccgtgtac tactgccagc agtccaagga ggaccccagg  300
accttcggcc agggcaccaa gctggagatc aagggaggcg gtggatcagg cggaggtggc  360
tcaggtggag gcggttctga ggtgcagctg gtgcagtccg gcgccgaggt gaagaagccc  420
ggcgcctccg tgaaggtgtc ctgcaaggcc tccggctaca ccttcaccga ctacaacatg  480
gactgggtga ggcaggcccc cggccagggc ctggagtgga tcggcgacat caaccccaac  540
aacggcggca ccctgtacaa ccagaagttc aggggcaggg tgaccctgac cgtggacacc  600
tccatctcca ccgcctacat ggagctgtcc aggctgaggt ccgacgacac cgccgtgtac  660
tactgcgcca ggtccgaggt gttctacggc aactacgccg actactgggg ccagggcacc  720
accgtgaccg tgtcctccga gcccaagtcc tgcgacaaga cccacacctg ccccccctgc  780
cccgcccccg aggccgccgg cggcccctcc gtgttcctgt tccccccaa gcccaaggac  840
accctgatga tctccaggac ccccgaggtg acctgcgtgg tggtggacgt gtcccacgag  900
gaccccgagg tgaagttcaa ctggtacgtg gacggcgtgg aggtgcacaa cgccaagacc  960
aagcccaggg aggagcagta caactccacc tacagggtgg tgtccgtgct gaccgtgctg  1020
caccaggact ggctgaacgg caaggagtac aagtgcaagg tgtccaacaa ggccctgccc  1080
gcccccatcg agaagaccat ctccaaggcc aagggccagc ccagggagcc ccaggtgtgc  1140
accctgcccc cctccaggga cgagctgacc aagaaccagg tgtccctgtc ctgcgccgtg  1200
aagggcttct accccctccga catcgccgtg gagtgggagt ccaacggcca gcccgagaac  1260
aactacaaga ccaccccccc cgtgctggac tccgacggct ccttcttcct ggtgtccaag  1320
ctgaccgtgg acaagtccag gtggcagcag ggcaacgtgt tctcctgctc cgtgatgcac  1380
gaggccctgc acaaccacta cacccagaag tccctgtccc tgtcccccgg caagtaa     1437

SEQ ID NO: 72          moltype = DNA  length = 1437
FEATURE                Location/Qualifiers
misc_feature           1..1437
                       note = 72
source                 1..1437
                       mol_type = other DNA
                       organism = synthetic construct
SEQUENCE: 72
gacatcgtgc tgacccagtc ccccgactcc ctggccgtgt ccctgggcga gagggccacc  60
atcaactgca aggcctccca gtccgtggac tacgacggcg actcctacat gaactggtac  120
cagcagaagc ccggccagcc ccccaagctg ctgatctacg ccgcctccac cctgcactcc  180
ggcgtgcccg acaggttctc cggctccggc tccggcaccg acttcaccct gaccatctcc  240
tccctgcagg ccgaggacgt ggccgtgtac tactgccagc agtccaagga ggaccccagg  300
accttcggcc agggcaccaa gctggagatc aagggaggcg gtggatcagg cggaggtggc  360
tcaggtggag gcggttctga ggtgcagctg gtgcagtccg gcgccgaggt gaagaagccc  420
ggcgcctccg tgaaggtgtc ctgcaaggcc tccggctaca ccttcaccga ctacaacatg  480
gactgggtga ggcaggcccc cggccagggc ctggagtgga tcggcgacat caaccccaac  540
aacggcggca ccctgtacaa ccagaagttc aggggcaggg tgaccctgac cgtggacaag  600
tccatctcca ccgcctacat ggagctgtcc aggctgaggt ccgacgacac cgccgtgtac  660
tactgcgcca ggtccgaggt gttctacggc aactacgccg actactgggg ccagggcacc  720
accgtgaccg tgtcctccga gcccaagtcc tgcgacaaga cccacacctg ccccccctgc  780
cccgcccccg aggccgccgg cggcccctcc gtgttcctgt tccccccaa gcccaaggac  840
accctgatga tctccaggac ccccgaggtg acctgcgtgg tggtggacgt gtcccacgag  900
gaccccgagg tgaagttcaa ctggtacgtg gacggcgtgg aggtgcacaa cgccaagacc  960
aagcccaggg aggagcagta caactccacc tacagggtgg tgtccgtgct gaccgtgctg  1020
caccaggact ggctgaacgg caaggagtac aagtgcaagg tgtccaacaa ggccctgccc  1080
gcccccatcg agaagaccat ctccaaggcc aagggccagc ccagggagcc ccaggtgtgc  1140
accctgcccc cctccaggga cgagctgacc aagaaccagg tgtccctgtc ctgcgccgtg  1200
aagggcttct accccctccga catcgccgtg gagtgggagt ccaacggcca gcccgagaac  1260
aactacaaga ccaccccccc cgtgctggac tccgacggct ccttcttcct ggtgtccaag  1320
ctgaccgtgg acaagtccag gtggcagcag ggcaacgtgt tctcctgctc cgtgatgcac  1380
gaggccctgc acaaccacta cacccagaag tccctgtccc tgtcccccgg caagtaa     1437

SEQ ID NO: 73          moltype = DNA  length = 1437
FEATURE                Location/Qualifiers
misc_feature           1..1437
                       note = 73
source                 1..1437
                       mol_type = other DNA
                       organism = synthetic construct
SEQUENCE: 73
gacatcgtgc tgacccagtc ccccgactcc ctggccgtgt ccctgggcga gagggccacc  60
atcaactgca aggcctccca gtccgtggac tacgacggcg actcctacat gaactggtac  120
cagcagaagc ccggccagcc ccccaagctg ctgatctacg ccgcctccac cctgcactcc  180
ggcgtgcccg acaggttctc cggctccggc tccggcaccg acttcaccct gaccatctcc  240
```

```
tccctgcagg ccgaggacgt ggccgtgtac tactgccagc agtccaagga ggaccccagg  300
accttcggcc agggcaccaa gctggagatc aagggaggcg gtggatcagg cggaggtggc  360
tcaggtggag gcggttctga ggtgcagctg gtgcagtccg gcgccgaggt gaagaagccc  420
ggcgcctccg tgaaggtgtc ctgcaaggcc tccggctaca ccttcaccga ctacaacatg  480
gactgggtga ggcaggcccc cggcaagggc ctggagtgga tcggcgacat caaccccaac  540
aacggcggca ccctgtacaa ccagaagttc aggggcaggg tgaccctgac cgtggacaag  600
tccatctcca ccgcctacat ggagctgtcc aggctgaggt ccgacgacac cgccgtgtac  660
tactgcgcca ggtccgaggt gttctacggc aactacgccg actactgggg ccagggcacc  720
accgtgaccg tgtcctccga gcccaagtcc tgcgacaaga cccacacctg cccccctgc   780
cccgccccg  aggccgccgg cggcccctcc gtgttcctgt tcccccccaa gcccaaggac  840
accctgatga tctccaggac cccgaggtg  acctgcgtgg tggtggacgt gtcccacgag  900
gaccccgagg tgaagttcaa ctggtacgtg gacggcgtgg aggtgcacaa cgccaagacc  960
aagcccaggg aggagcagta caactccacc tacagggtgg tgtccgtgct gaccgtgctg  1020
caccaggact ggctgaacgg caaggagtac aagtgcaagg tgtccaacaa ggccctgccc  1080
gcccccatcg agaagaccat ctccaaggcc aagggccagc ccagggagcc ccaggtgtgc  1140
accctgcccc cctccaggga cgagctgacc aagaaccagg tgtccctgtc ctgcgccgtg  1200
aagggcttct accccctccga catcgccgtg gagtgggagt ccaacggcca gcccgagaac  1260
aactacaaga ccacccccc  cgtgctggac tccgacggct ccttcttcct ggtgtccaag  1320
ctgaccgtgg acaagtccag gtggcagcag ggcaacgtgt tctcctgctc cgtgatgcac  1380
gaggccctgc acaaccacta cacccagaag tccctgtccc tgtcccccgg caagtaa     1437

SEQ ID NO: 74           moltype = DNA  length = 1437
FEATURE                 Location/Qualifiers
misc_feature            1..1437
                        note = 74
source                  1..1437
                        mol_type = other DNA
                        organism = synthetic construct
SEQUENCE: 74
gacatcgtgc tgacccagtc ccccgactcc ctggccgtgt ccctgggcga gagggccacc  60
atcaactgca aggcctccca gtccgtggac tacgacggcg actcctacat gaactggtac  120
cagcagaagc ccggccagcc ccccaagctg ctgatctacg ccgcctccac cctgcactcc  180
ggcatccccg acaggttctc cggctccggc tccggcaccg acttcaccct gaccatctcc  240
tccctgcagg ccgaggacgt ggccgtgtac tactgccagc agtccaagga ggaccccagg  300
accttcggcc agggcaccaa gctggagatc aagggaggcg gtggatcagg cggaggtggc  360
tcaggtggag gcggttctga ggtgcagctg gtgcagtccg gcgccgaggt gaagaagccc  420
ggcgcctccg tgaaggtgtc ctgcaaggcc tccggctaca ccttcaccga ctacaacatg  480
gactgggtga ggcaggcccc cggccagggc ctggagtgga tgggcgacat caaccccaac  540
aacggcggca ccctgtacaa ccagaagttc aggggcaggg tgaccatgac cgtggacacc  600
tccatctcca ccgcctacat ggagctgtcc aggctgaggt ccgacgacac cgccgtgtac  660
tactgcgcca ggtccgaggt gttctacggc aactacgccg actactgggg ccagggcacc  720
accgtgaccg tgtcctccga gcccaagtcc tgcgacaaga cccacacctg cccccctgc   780
cccgccccg  aggccgccgg cggcccctcc gtgttcctgt tcccccccaa gcccaaggac  840
accctgatga tctccaggac cccgaggtg  acctgcgtgg tggtggacgt gtcccacgag  900
gaccccgagg tgaagttcaa ctggtacgtg gacggcgtgg aggtgcacaa cgccaagacc  960
aagcccaggg aggagcagta caactccacc tacagggtgg tgtccgtgct gaccgtgctg  1020
caccaggact ggctgaacgg caaggagtac aagtgcaagg tgtccaacaa ggccctgccc  1080
gcccccatcg agaagaccat ctccaaggcc aagggccagc ccagggagcc ccaggtgtgc  1140
accctgcccc cctccaggga cgagctgacc aagaaccagg tgtccctgtc ctgcgccgtg  1200
aagggcttct accccctccga catcgccgtg gagtgggagt ccaacggcca gcccgagaac  1260
aactacaaga ccacccccc  cgtgctggac tccgacggct ccttcttcct ggtgtccaag  1320
ctgaccgtgg acaagtccag gtggcagcag ggcaacgtgt tctcctgctc cgtgatgcac  1380
gaggccctgc acaaccacta cacccagaag tccctgtccc tgtcccccgg caagtaa     1437

SEQ ID NO: 75           moltype = DNA  length = 1437
FEATURE                 Location/Qualifiers
misc_feature            1..1437
                        note = 75
source                  1..1437
                        mol_type = other DNA
                        organism = synthetic construct
SEQUENCE: 75
gacatcgtgc tgacccagtc ccccgactcc ctggccgtgt ccctgggcga gagggccacc  60
atcaactgca aggcctccca gtccgtggac tacgacggcg actcctacat gaactggtac  120
cagcagaagc ccggccagcc ccccaagctg ctgatctacg ccgcctccac cctgcactcc  180
ggcatccccg acaggttctc cggctccggc tccggcaccg acttcaccct gaccatctcc  240
tccctgcagg ccgaggacgt ggccgtgtac tactgccagc agtccaagga ggaccccagg  300
accttcggcc agggcaccaa gctggagatc aagggaggcg gtggatcagg cggaggtggc  360
tcaggtggag gcggttctga ggtgcagctg gtgcagtccg gcgccgaggt gaagaagccc  420
ggcgcctccg tgaaggtgtc ctgcaaggcc tccggctaca ccttcaccga ctacaacatg  480
gactgggtga ggcaggcccc cggccagggc ctggagtgga tcggcgacat caaccccaac  540
aacggcggca ccctgtacaa ccagaagttc aggggcaggg tgaccctgac cgtggacacc  600
tccatctcca ccgcctacat ggagctgtcc aggctgaggt ccgacgacac cgccgtgtac  660
tactgcgcca ggtccgaggt gttctacggc aactacgccg actactgggg ccagggcacc  720
accgtgaccg tgtcctccga gcccaagtcc tgcgacaaga cccacacctg cccccctgc   780
cccgccccg  aggccgccgg cggcccctcc gtgttcctgt tcccccccaa gcccaaggac  840
accctgatga tctccaggac cccgaggtg  acctgcgtgg tggtggacgt gtcccacgag  900
gaccccgagg tgaagttcaa ctggtacgtg gacggcgtgg aggtgcacaa cgccaagacc  960
aagcccaggg aggagcagta caactccacc tacagggtgg tgtccgtgct gaccgtgctg  1020
```

```
caccaggact ggctgaacgg caaggagtac aagtgcaagg tgtccaacaa ggccctgccc  1080
gcccccatcg agaagaccat ctccaaggcc aagggccagc ccagggagcc ccaggtgtgc  1140
accctgcccc cctccaggga cgagctgacc aagaaccagg tgtccctgtc ctgcgccgtg  1200
aagggcttct accccctccga catcgccgtg gagtgggagt ccaacggcca gcccgagaac  1260
aactacaaga ccaccccccc cgtgctggac tccgacggct ccttcttcct ggtgtccaag  1320
ctgaccgtgg acaagtccag gtggcagcag ggcaacgtgt tctcctgctc cgtgatgcac  1380
gaggccctgc acaaccacta cacccagaag tccctgtccc tgtcccccgg caagtaa     1437

SEQ ID NO: 76           moltype = DNA  length = 1437
FEATURE                 Location/Qualifiers
misc_feature            1..1437
                        note = 76
source                  1..1437
                        mol_type = other DNA
                        organism = synthetic construct
SEQUENCE: 76
gacatcgtgc tgacccagtc ccccgactcc ctggccgtgt ccctgggcga gagggccacc  60
atcaactgca aggcctccca gtccgtggac tacgacggcg actcctacat gaactggtac  120
cagcagaagc ccggccagcc ccccaagctg ctgatctacg ccgcctccac cctgcactcc  180
ggcatccccg acaggttctc cggctccggc tccggcaccg acttcaccct gaccatctcc  240
tccctgcagg ccgaggacgt ggccgtgtac tactgccagc agtccaagga ggaccccagg  300
accttcggcc agggcaccaa gctggagatc aagggaggcg gtggatcagg cggaggtggc  360
tcaggtggag gcggttctga ggtgcagctg gtgcagtccg gcgccgaggt gaagaagccc  420
ggcgcctccg tgaaggtgtc ctgcaaggcc tccggctaca ccttcaccga ctacaacatg  480
gactgggtga ggcaggcccc cggccagggc ctggagtgga tcggcgacat caaccccaac  540
aacggcggca ccctgtacaa ccagaagttc aggggcaggg tgaccctgac cgtggacaag  600
tccatctcca ccgcctacat ggagctgtcc aggctgaggt ccgacgacac cgccgtgtac  660
tactgcgcca ggtccgaggt gttctacggc aactacgccg actactgggg ccagggcacc  720
accgtgaccg tgtcctccga gcccaagtcc tgcgacaaga cccacacctg cccccccctgc  780
cccgcccccg aggccgccgg cggcccctcc gtgttcctgt tccccccccaa gcccaaggac  840
accctgatga tctccaggac ccccgaggtg acctgcgtgg tggtggacgt gtcccacgag  900
gaccccgagg tgaagttcaa ctggtacgtg gacggcgtgg aggtgcacaa cgccaagacc  960
aagcccaggg aggagcagta caactccacc tacagggtgg tgtccgtgct gaccgtgctg  1020
caccaggact ggctgaacgg caaggagtac aagtgcaagg tgtccaacaa ggccctgccc  1080
gcccccatcg agaagaccat ctccaaggcc aagggccagc ccagggagcc ccaggtgtgc  1140
accctgcccc cctccaggga cgagctgacc aagaaccagg tgtccctgtc ctgcgccgtg  1200
aagggcttct accccctccga catcgccgtg gagtgggagt ccaacggcca gcccgagaac  1260
aactacaaga ccaccccccc cgtgctggac tccgacggct ccttcttcct ggtgtccaag  1320
ctgaccgtgg acaagtccag gtggcagcag ggcaacgtgt tctcctgctc cgtgatgcac  1380
gaggccctgc acaaccacta cacccagaag tccctgtccc tgtcccccgg caagtaa     1437

SEQ ID NO: 77           moltype = DNA  length = 1437
FEATURE                 Location/Qualifiers
misc_feature            1..1437
                        note = 77
source                  1..1437
                        mol_type = other DNA
                        organism = synthetic construct
SEQUENCE: 77
gacatcgtgc tgacccagtc ccccgactcc ctggccgtgt ccctgggcga gagggccacc  60
atcaactgca aggcctccca gtccgtggac tacgacggcg actcctacat gaactggtac  120
cagcagaagc ccggccagcc ccccaagctg ctgatctacg ccgcctccac cctgcactcc  180
ggcatccccg acaggttctc cggctccggc tccggcaccg acttcaccct gaccatctcc  240
tccctgcagg ccgaggacgt ggccgtgtac tactgccagc agtccaagga ggaccccagg  300
accttcggcc agggcaccaa gctggagatc aagggaggcg gtggatcagg cggaggtggc  360
tcaggtggag gcggttctga ggtgcagctg gtgcagtccg gcgccgaggt gaagaagccc  420
ggcgcctccg tgaaggtgtc ctgcaaggcc tccggctaca ccttcaccga ctacaacatg  480
gactgggtga ggcaggcccc cggcaagggc ctggagtgga tcggcgacat caaccccaac  540
aacggcggca ccctgtacaa ccagaagttc aggggcaggg tgaccctgac cgtggacaag  600
tccatctcca ccgcctacat ggagctgtcc aggctgaggt ccgacgacac cgccgtgtac  660
tactgcgcca ggtccgaggt gttctacggc aactacgccg actactgggg ccagggcacc  720
accgtgaccg tgtcctccga gcccaagtcc tgcgacaaga cccacacctg cccccccctgc  780
cccgcccccg aggccgccgg cggcccctcc gtgttcctgt tccccccccaa gcccaaggac  840
accctgatga tctccaggac ccccgaggtg acctgcgtgg tggtggacgt gtcccacgag  900
gaccccgagg tgaagttcaa ctggtacgtg gacggcgtgg aggtgcacaa cgccaagacc  960
aagcccaggg aggagcagta caactccacc tacagggtgg tgtccgtgct gaccgtgctg  1020
caccaggact ggctgaacgg caaggagtac aagtgcaagg tgtccaacaa ggccctgccc  1080
gcccccatcg agaagaccat ctccaaggcc aagggccagc ccagggagcc ccaggtgtgc  1140
accctgcccc cctccaggga cgagctgacc aagaaccagg tgtccctgtc ctgcgccgtg  1200
aagggcttct accccctccga catcgccgtg gagtgggagt ccaacggcca gcccgagaac  1260
aactacaaga ccaccccccc cgtgctggac tccgacggct ccttcttcct ggtgtccaag  1320
ctgaccgtgg acaagtccag gtggcagcag ggcaacgtgt tctcctgctc cgtgatgcac  1380
gaggccctgc acaaccacta cacccagaag tccctgtccc tgtcccccgg caagtaa     1437

SEQ ID NO: 78           moltype = DNA  length = 1437
FEATURE                 Location/Qualifiers
misc_feature            1..1437
                        note = 78
source                  1..1437
```

```
                         mol_type = other DNA
                         organism = synthetic construct
SEQUENCE: 78
gacatcgtgc tgacccagac cccccctgtcc ctgtccgtga cccccggcca gcccgcctcc  60
atctcctgca aggcctccca gtccgtggac tacgacggcg actcctacat gaactggtac  120
ctgcagaagc ccggccagcc cccccagctg ctgatctacg ccgcctccac cctgcactcc  180
ggcgtgcccg acaggttctc cggctccggc tccggcaccg acttcaccct gaagatctcc  240
agggtggagg ccgaggacgt gggcgtgtac tactgccagc agtccaagga ggaccccagg  300
accttcggcc agggcaccaa gctggagatc aagggaggcg gtggatcagg cggaggtggc  360
tcaggtggag gcggttctga ggtgcagctg gtgcagtccg gcgccgaggt gaagaagccc  420
ggcgcctccg tgaaggtgtc ctgcaaggcc tccggctaca ccttcaccga ctacaacatg  480
gactgggtga ggcaggcccc cggccagggc ctggagtgga tgggcgacat caaccccaac  540
aacggcggca ccctgtacaa ccagaagttc aggggcaggg tgaccatgac cgtggacacc  600
tccatctcca ccgcctacat ggagctgtcc aggctgaggt ccgacgacac cgccgtgtac  660
tactgcgcca ggtccgaggt gttctacggc aactacgccg actactgggg ccagggcacc  720
accgtgaccg tgtcctccga gcccaagtcc tgcgacaaga cccacacctg cccccccctgc  780
cccgcccccg aggccgccgg cggcccctcc gtgttcctgt tcccccccaa gcccaaggac  840
accctgatga tctccaggac ccccgaggtg acctgcgtgg tggtggacgt gtcccacgag  900
gaccccgagg tgaagttcaa ctggtacgtg gacggcgtgg aggtgcacaa cgccaagacc  960
aagcccaggg aggagcagta caactccacc tacagggtgg tgtccgtgct gaccgtgctg  1020
caccaggact ggctgaacgg caaggagtac aagtgcaagg tgtccaacaa ggccctgccc  1080
gcccccatcg agaagaccat ctccaaggcc aagggccagc ccagggagcc ccaggtgtgc  1140
accctgcccc cctccaggga cgagctgacc aagaaccagg tgtccctgtc ctgcgccgtg  1200
aagggcttct accccctccga catcgccgtg gagtgggagt ccaacggcca gcccgagaac  1260
aactacaaga ccacccccccc cgtgctggac tccgacggct ccttcttcct ggtgtccaag  1320
ctgaccgtgg acaagtccag gtggcagcag ggcaacgtgt tctcctgctc cgtgatgcac  1380
gaggccctgc acaaccacta cacccagaag tccctgtccc tgtcccccgg caagtaa     1437

SEQ ID NO: 79            moltype = DNA  length = 1437
FEATURE                  Location/Qualifiers
misc_feature             1..1437
                         note = 79
source                   1..1437
                         mol_type = other DNA
                         organism = synthetic construct
SEQUENCE: 79
gacatcgtgc tgacccagac cccccctgtcc ctgtccgtga cccccggcca gcccgcctcc  60
atctcctgca aggcctccca gtccgtggac tacgacggcg actcctacat gaactggtac  120
ctgcagaagc ccggccagcc cccccagctg ctgatctacg ccgcctccac cctgcactcc  180
ggcgtgcccg acaggttctc cggctccggc tccggcaccg acttcaccct gaagatctcc  240
agggtggagg ccgaggacgt gggcgtgtac tactgccagc agtccaagga ggaccccagg  300
accttcggcc agggcaccaa gctggagatc aagggaggcg gtggatcagg cggaggtggc  360
tcaggtggag gcggttctga ggtgcagctg gtgcagtccg gcgccgaggt gaagaagccc  420
ggcgcctccg tgaaggtgtc ctgcaaggcc tccggctaca ccttcaccga ctacaacatg  480
gactgggtga ggcaggcccc cggccagggc ctggagtgga tcggcgacat caaccccaac  540
aacggcggca ccctgtacaa ccagaagttc aggggcaggg tgaccctgac cgtggacacc  600
tccatctcca ccgcctacat ggagctgtcc aggctgaggt ccgacgacac cgccgtgtac  660
tactgcgcca ggtccgaggt gttctacggc aactacgccg actactgggg ccagggcacc  720
accgtgaccg tgtcctccga gcccaagtcc tgcgacaaga cccacacctg cccccccctgc  780
cccgcccccg aggccgccgg cggcccctcc gtgttcctgt tcccccccaa gcccaaggac  840
accctgatga tctccaggac ccccgaggtg acctgcgtgg tggtggacgt gtcccacgag  900
gaccccgagg tgaagttcaa ctggtacgtg gacggcgtgg aggtgcacaa cgccaagacc  960
aagcccaggg aggagcagta caactccacc tacagggtgg tgtccgtgct gaccgtgctg  1020
caccaggact ggctgaacgg caaggagtac aagtgcaagg tgtccaacaa ggccctgccc  1080
gcccccatcg agaagaccat ctccaaggcc aagggccagc ccagggagcc ccaggtgtgc  1140
accctgcccc cctccaggga cgagctgacc aagaaccagg tgtccctgtc ctgcgccgtg  1200
aagggcttct accccctccga catcgccgtg gagtgggagt ccaacggcca gcccgagaac  1260
aactacaaga ccacccccccc cgtgctggac tccgacggct ccttcttcct ggtgtccaag  1320
ctgaccgtgg acaagtccag gtggcagcag ggcaacgtgt tctcctgctc cgtgatgcac  1380
gaggccctgc acaaccacta cacccagaag tccctgtccc tgtcccccgg caagtaa     1437

SEQ ID NO: 80            moltype = DNA  length = 1437
FEATURE                  Location/Qualifiers
misc_feature             1..1437
                         note = 80
source                   1..1437
                         mol_type = other DNA
                         organism = synthetic construct
SEQUENCE: 80
gacatcgtgc tgacccagac cccccctgtcc ctgtccgtga cccccggcca gcccgcctcc  60
atctcctgca aggcctccca gtccgtggac tacgacggcg actcctacat gaactggtac  120
ctgcagaagc ccggccagcc cccccagctg ctgatctacg ccgcctccac cctgcactcc  180
ggcgtgcccg acaggttctc cggctccggc tccggcaccg acttcaccct gaagatctcc  240
agggtggagg ccgaggacgt gggcgtgtac tactgccagc agtccaagga ggaccccagg  300
accttcggcc agggcaccaa gctggagatc aagggaggcg gtggatcagg cggaggtggc  360
tcaggtggag gcggttctga ggtgcagctg gtgcagtccg gcgccgaggt gaagaagccc  420
ggcgcctccg tgaaggtgtc ctgcaaggcc tccggctaca ccttcaccga ctacaacatg  480
gactgggtga ggcaggcccc cggccagggc ctggagtgga tcggcgacat caaccccaac  540
aacggcggca ccctgtacaa ccagaagttc aggggcaggg tgaccctgac cgtggacaag  600
```

```
tccatctcca ccgcctacat ggagctgtcc aggctgaggt ccgacgacac cgccgtgtac  660
tactgcgcca ggtccgaggt gttctacggc aactacgccg actactgggg ccagggcacc  720
accgtgaccg tgtcctccga gcccaagtcc tgcgacaaga cccacacctg cccccccctgc  780
cccgcccccg aggccgccgg cggcccctcc gtgttcctgt tcccccccaa gcccaaggac  840
accctgatga tctccaggac ccccgaggtg acctgcgtgg tggtggacgt gtcccacgag  900
gaccccgagg tgaagttcaa ctggtacgtg gacggcgtgg aggtgcacaa cgccaagacc  960
aagcccaggg aggagcagta caactccacc tacagggtgg tgtccgtgct gaccgtgctg  1020
caccaggact ggctgaacgg caaggagtac aagtgcaagg tgtccaacaa ggccctgccc  1080
gcccccatcg agaagaccat ctccaaggcc aagggccagc ccagggagcc ccaggtgtgc  1140
accctgcccc cctccaggga cgagctgacc aagaaccagg tgtccctgtc ctgcgccgtg  1200
aagggcttct accccctccga catcgccgtg gagtgggagt ccaacggcca gcccgagaac  1260
aactacaaga ccaccccccc cgtgctggac tccgacggct ccttcttcct ggtgtccaag  1320
ctgaccgtgg acaagtccag gtggcagcag ggcaacgtgt tctcctgctc cgtgatgcac  1380
gaggccctgc acaaccacta cacccagaag tccctgtccc tgtcccccgg caagtaa     1437

SEQ ID NO: 81          moltype = DNA  length = 1437
FEATURE                Location/Qualifiers
misc_feature           1..1437
                       note = 81
source                 1..1437
                       mol_type = other DNA
                       organism = synthetic construct
SEQUENCE: 81
gacatcgtgc tgacccagac cccccctgtcc ctgtccgtga cccccggcca gcccgcctcc  60
atctcctgca aggcctccca gtccgtggac tacgacggcg actcctacat gaactggtac  120
ctgcagaagc ccggccagcc cccccagctg ctgatctacg ccgcctccac cctgcactcc  180
ggcgtgcccg acaggttctc cggctccggc tccggcaccg acttcaccct gaagatctcc  240
agggtggagg ccgaggacgt gggcgtgtac tactgccagc agtccaagga ggaccccagg  300
accttcggcc agggcaccaa gctggagatc aagggaggcg gtggatcagg cggaggtggc  360
tcaggtggag gcggttctga ggtgcagctg gtgcagtccg gcgccgaggt gaagaagccc  420
ggcgcctccg tgaaggtgtc ctgcaaggcc tccggctaca ccttcaccga ctacaacatg  480
gactgggtga ggcaggcccc cggcaagggc ctggagtgga tcggcgacat caaccccaac  540
aacggcggca ccctgtacaa ccagaagttc aggggcaggg tgaccctgac cgtggacaag  600
tccatctcca ccgcctacat ggagctgtcc aggctgaggt ccgacgacac cgccgtgtac  660
tactgcgcca ggtccgaggt gttctacggc aactacgccg actactgggg ccagggcacc  720
accgtgaccg tgtcctccga gcccaagtcc tgcgacaaga cccacacctg cccccccctgc  780
cccgcccccg aggccgccgg cggcccctcc gtgttcctgt tcccccccaa gcccaaggac  840
accctgatga tctccaggac ccccgaggtg acctgcgtgg tggtggacgt gtcccacgag  900
gaccccgagg tgaagttcaa ctggtacgtg gacggcgtgg aggtgcacaa cgccaagacc  960
aagcccaggg aggagcagta caactccacc tacagggtgg tgtccgtgct gaccgtgctg  1020
caccaggact ggctgaacgg caaggagtac aagtgcaagg tgtccaacaa ggccctgccc  1080
gcccccatcg agaagaccat ctccaaggcc aagggccagc ccagggagcc ccaggtgtgc  1140
accctgcccc cctccaggga cgagctgacc aagaaccagg tgtccctgtc ctgcgccgtg  1200
aagggcttct accccctccga catcgccgtg gagtgggagt ccaacggcca gcccgagaac  1260
aactacaaga ccaccccccc cgtgctggac tccgacggct ccttcttcct ggtgtccaag  1320
ctgaccgtgg acaagtccag gtggcagcag ggcaacgtgt tctcctgctc cgtgatgcac  1380
gaggccctgc acaaccacta cacccagaag tccctgtccc tgtcccccgg caagtaa     1437

SEQ ID NO: 82          moltype = DNA  length = 1437
FEATURE                Location/Qualifiers
misc_feature           1..1437
                       note = 82
source                 1..1437
                       mol_type = other DNA
                       organism = synthetic construct
SEQUENCE: 82
gacatcgtgc tgacccagac cccccctgtcc ctgtccgtga cccccggcca gcccgcctcc  60
atctcctgca aggcctccca gtccgtggac tacgacggcg actcctacat gaactggtac  120
ctgcagaagc ccggccagcc cccccagctg ctgatctacg ccgcctccac cctgcactcc  180
ggcatccccg acaggttctc cggctccggc tccggcaccg acttcaccct gaagatctcc  240
agggtggagg ccgaggacgt gggcgtgtac tactgccagc agtccaagga ggaccccagg  300
accttcggcc agggcaccaa gctggagatc aagggaggcg gtggatcagg cggaggtggc  360
tcaggtggag gcggttctga ggtgcagctg gtgcagtccg gcgccgaggt gaagaagccc  420
ggcgcctccg tgaaggtgtc ctgcaaggcc tccggctaca ccttcaccga ctacaacatg  480
gactgggtga ggcaggcccc cggccagggc ctggagtgga tgggcgacat caaccccaac  540
aacggcggca ccctgtacaa ccagaagttc aggggcaggg tgaccatgac cgtggacacc  600
tccatctcca ccgcctacat ggagctgtcc aggctgaggt ccgacgacac cgccgtgtac  660
tactgcgcca ggtccgaggt gttctacggc aactacgccg actactgggg ccagggcacc  720
accgtgaccg tgtcctccga gcccaagtcc tgcgacaaga cccacacctg cccccccctgc  780
cccgcccccg aggccgccgg cggcccctcc gtgttcctgt tcccccccaa gcccaaggac  840
accctgatga tctccaggac ccccgaggtg acctgcgtgg tggtggacgt gtcccacgag  900
gaccccgagg tgaagttcaa ctggtacgtg gacggcgtgg aggtgcacaa cgccaagacc  960
aagcccaggg aggagcagta caactccacc tacagggtgg tgtccgtgct gaccgtgctg  1020
caccaggact ggctgaacgg caaggagtac aagtgcaagg tgtccaacaa ggccctgccc  1080
gcccccatcg agaagaccat ctccaaggcc aagggccagc ccagggagcc ccaggtgtgc  1140
accctgcccc cctccaggga cgagctgacc aagaaccagg tgtccctgtc ctgcgccgtg  1200
aagggcttct accccctccga catcgccgtg gagtgggagt ccaacggcca gcccgagaac  1260
aactacaaga ccaccccccc cgtgctggac tccgacggct ccttcttcct ggtgtccaag  1320
ctgaccgtgg acaagtccag gtggcagcag ggcaacgtgt tctcctgctc cgtgatgcac  1380
```

```
gaggccctgc acaaccacta cacccagaag tccctgtccc tgtcccccgg caagtaa     1437

SEQ ID NO: 83          moltype = DNA  length = 1437
FEATURE                Location/Qualifiers
misc_feature           1..1437
                       note = 83
source                 1..1437
                       mol_type = other DNA
                       organism = synthetic construct
SEQUENCE: 83
gacatcgtgc tgacccagac ccccctgtcc ctgtccgtga cccccggcca gcccgcctcc  60
atctcctgca aggcctccca gtccgtggac tacgacggcg actcctacat gaactggtac  120
ctgcagaagc ccggccagcc cccccagctg ctgatctacg ccgcctccac cctgcactcc  180
ggcatccccg acaggttctc cggctccggc tccggcaccg acttcaccct gaagatctcc  240
agggtggagg ccgaggacgt gggcgtgtac tactgccagc agtccaagga ggaccccagg  300
accttcggcc agggcaccaa gctggagatc aagggaggcg gtggatcagg cggaggtggc  360
tcaggtggag gcggttctga ggtgcagctg gtgcagtccg gcgccgaggt gaagaagccc  420
ggcgcctccg tgaaggtgtc ctgcaaggcc tccggctaca ccttcaccga ctacaacatg  480
gactgggtga ggcaggcccc cggccagggc ctggagtgga tcggcgacat caaccccaac  540
aacggcggca ccctgtacaa ccagaagttc aggggcaggg tgaccctgac cgtggacacc  600
tccatctcca ccgcctacat ggagctgtcc aggctgaggt ccgacgacac cgccgtgtac  660
tactgcgcca ggtccgaggt gttctacggc aactacgccg actactgggg ccagggcacc  720
accgtgaccg tgtcctccga gcccaagtcc tgcgacaaga cccacacctg cccccccctgc  780
cccgcccccg aggccgccgg cggcccctcc gtgttcctgt tcccccccaa gcccaaggac  840
accctgatga tctccaggac ccccgaggtg acctgcgtgg tggtggacgt gtcccacgag  900
gaccccgagg tgaagttcaa ctggtacgtg gacggcgtgg aggtgcacaa cgccaagacc  960
aagcccaggg aggagcagta caactccacc tacagggtgg tgtccgtgct gaccgtgctg  1020
caccaggact ggctgaacgg caaggagtac aagtgcaagg tgtccaacaa ggccctgccc  1080
gcccccatcg agaagaccat ctccaaggcc aagggccagc ccagggagcc ccaggtgtgc  1140
accctgcccc cctccaggga cgagctgacc aagaaccagg tgtccctgtc ctgcgccgtg  1200
aagggcttct accccctccga catcgccgtg gagtgggagt ccaacggcca gcccgagaac  1260
aactacaaga ccaccccccc cgtgctggac tccgacggct ccttcttcct ggtgtccaag  1320
ctgaccgtgg acaagtccag gtggcagcag ggcaacgtgt tctcctgctc cgtgatgcac  1380
gaggccctgc acaaccacta cacccagaag tccctgtccc tgtcccccgg caagtaa     1437

SEQ ID NO: 84          moltype = DNA  length = 1437
FEATURE                Location/Qualifiers
misc_feature           1..1437
                       note = 84
source                 1..1437
                       mol_type = other DNA
                       organism = synthetic construct
SEQUENCE: 84
gacatcgtgc tgacccagac ccccctgtcc ctgtccgtga cccccggcca gcccgcctcc  60
atctcctgca aggcctccca gtccgtggac tacgacggcg actcctacat gaactggtac  120
ctgcagaagc ccggccagcc cccccagctg ctgatctacg ccgcctccac cctgcactcc  180
ggcatccccg acaggttctc cggctccggc tccggcaccg acttcaccct gaagatctcc  240
agggtggagg ccgaggacgt gggcgtgtac tactgccagc agtccaagga ggaccccagg  300
accttcggcc agggcaccaa gctggagatc aagggaggcg gtggatcagg cggaggtggc  360
tcaggtggag gcggttctga ggtgcagctg gtgcagtccg gcgccgaggt gaagaagccc  420
ggcgcctccg tgaaggtgtc ctgcaaggcc tccggctaca ccttcaccga ctacaacatg  480
gactgggtga ggcaggcccc cggccagggc ctggagtgga tcggcgacat caaccccaac  540
aacggcggca ccctgtacaa ccagaagttc aggggcaggg tgaccctgac cgtggacaag  600
tccatctcca ccgcctacat ggagctgtcc aggctgaggt ccgacgacac cgccgtgtac  660
tactgcgcca ggtccgaggt gttctacggc aactacgccg actactgggg ccagggcacc  720
accgtgaccg tgtcctccga gcccaagtcc tgcgacaaga cccacacctg cccccccctgc  780
cccgcccccg aggccgccgg cggcccctcc gtgttcctgt tcccccccaa gcccaaggac  840
accctgatga tctccaggac ccccgaggtg acctgcgtgg tggtggacgt gtcccacgag  900
gaccccgagg tgaagttcaa ctggtacgtg gacggcgtgg aggtgcacaa cgccaagacc  960
aagcccaggg aggagcagta caactccacc tacagggtgg tgtccgtgct gaccgtgctg  1020
caccaggact ggctgaacgg caaggagtac aagtgcaagg tgtccaacaa ggccctgccc  1080
gcccccatcg agaagaccat ctccaaggcc aagggccagc ccagggagcc ccaggtgtgc  1140
accctgcccc cctccaggga cgagctgacc aagaaccagg tgtccctgtc ctgcgccgtg  1200
aagggcttct accccctccga catcgccgtg gagtgggagt ccaacggcca gcccgagaac  1260
aactacaaga ccaccccccc cgtgctggac tccgacggct ccttcttcct ggtgtccaag  1320
ctgaccgtgg acaagtccag gtggcagcag ggcaacgtgt tctcctgctc cgtgatgcac  1380
gaggccctgc acaaccacta cacccagaag tccctgtccc tgtcccccgg caagtaa     1437

SEQ ID NO: 85          moltype = DNA  length = 1437
FEATURE                Location/Qualifiers
misc_feature           1..1437
                       note = 85
source                 1..1437
                       mol_type = other DNA
                       organism = synthetic construct
SEQUENCE: 85
gacatcgtgc tgacccagac ccccctgtcc ctgtccgtga cccccggcca gcccgcctcc  60
atctcctgca aggcctccca gtccgtggac tacgacggcg actcctacat gaactggtac  120
ctgcagaagc ccggccagcc cccccagctg ctgatctacg ccgcctccac cctgcactcc  180
```

```
ggcatccccg acaggttctc cggctccggc tccggcaccg acttcaccct gaagatctcc  240
agggtggagg ccgaggacgt gggcgtgtac tactgccagc agtccaagga ggaccccagg  300
accttcggcc agggcaccaa gctggagatc aagggaggcg gtggatcagg cggaggtggc  360
tcaggtggag gcggttctga ggtgcagctg gtgcagtccg gcgccgaggt gaagaagccc  420
ggcgcctccg tgaaggtgtc ctgcaaggcc tccggctaca ccttcaccga ctacaacatg  480
gactgggtga ggcaggcccc cggcaagggc ctggagtgga tcggcgacat caaccccaac  540
aacggcggca ccctgtacaa ccagaagttc aggggcaggg tgaccctgac cgtggacaag  600
tccatctcca ccgcctacat ggagctgtcc aggctgaggt ccgacgacac cgccgtgtac  660
tactgcgcca ggtccgaggt gttctacggc aactacgccg actactgggg ccagggcacc  720
accgtgaccg tgtcctccga gcccaagtcc tgcgacaaga cccacacctg ccccccctgc  780
cccgcccccg aggccgccgg cggcccctcc gtgttcctgt tcccccccaa gcccaaggac  840
accctgatga tctccaggac ccccgaggtg acctgcgtgg tggtggacgt gtcccacgag  900
gaccccgagg tgaagttcaa ctggtacgtg gacggcgtgg aggtgcacaa cgccaagacc  960
aagcccaggg aggagcagta caactccacc tacagggtgg tgtccgtgct gaccgtgctg  1020
caccaggact ggctgaacgg caaggagtac aagtgcaagg tgtccaacaa ggccctgccc  1080
gcccccatcg agaagaccat ctccaaggcc aagggccagc ccagggagcc ccaggtgtgc  1140
accctgcccc cctccaggga cgagctgacc aagaaccagg tgtccctgtc ctgcgccgtg  1200
aagggcttct accccctccga catcgccgtg gagtgggagt ccaacggcca gcccgagaac  1260
aactacaaga ccaccccccc cgtgctggac tccgacggct ccttcttcct ggtgtccaag  1320
ctgaccgtgg acaagtccag gtggcagcag ggcaacgtgt tctcctgctc cgtgatgcac  1380
gaggccctgc acaaccacta cacccagaag tccctgtccc tgtcccccgg caagtaa     1437

SEQ ID NO: 86           moltype = DNA  length = 1437
FEATURE                 Location/Qualifiers
misc_feature            1..1437
                        note = 86
source                  1..1437
                        mol_type = other DNA
                        organism = synthetic construct
SEQUENCE: 86
gacatcgtgc tgacccagtc ccccgtgtcc ctggccgtgc ccctgggcca gagggccacc  60
atctcctgca aggcctccca gtccgtggac tacgacggcg actcctacat gaactggtac  120
cagcagaagc ccggccagcc ccccaagctg ctgatctacg ccgcctccac cctgcactcc  180
ggcatccccg tgaggttctc cggctccggc tccggcaccg acttcaccct gaacatccac  240
cccgtggagg aggaggacgc cgcctcctac tactgccagc agtccaagga ggaccccagg  300
accttcggcg gcggcaccaa gctggagatc aagggaggcg gtggatcagg cggaggtggc  360
tcaggtggag gcggttctga ggtgctgctg cagcagtccg gccccgaggt ggtgaagccc  420
ggcgcctccg tgaagatcac ctgcaaggcc tccggctaca ccttcaccga ctacaacatg  480
gactgggtga agcagtccca cggcaagtcc ctggagtgga tcggcgacat caaccccaac  540
aacgccggca ccctgtacaa ccagaagttc aggggcaggg tgaccctgat cgtggacaag  600
tcctcctcca ccgcctacat ggagctgagg tccctgacct ccgacgacac cgccgtgtac  660
tactgcgcca ggtccgaggt gttctacggc aactacgccg actactgggg ccagggcacc  720
accctgaccg tgtcctccga gcccaagtcc tgcgacaaga cccacacctg ccccccctgc  780
cccgcccccg aggccgccgg cggcccctcc gtgttcctgt tcccccccaa gcccaaggac  840
accctgatga tctccaggac ccccgaggtg acctgcgtgg tggtggacgt gtcccacgag  900
gaccccgagg tgaagttcaa ctggtacgtg gacggcgtgg aggtgcacaa cgccaagacc  960
aagcccaggg aggagcagta caactccacc tacagggtgg tgtccgtgct gaccgtgctg  1020
caccaggact ggctgaacgg caaggagtac aagtgcaagg tgtccaacaa ggccctgccc  1080
gcccccatcg agaagaccat ctccaaggcc aagggccagc ccagggagcc ccaggtgtgc  1140
accctgcccc cctccaggga cgagctgacc aagaaccagg tgtccctgtc ctgcgccgtg  1200
aagggcttct accccctccga catcgccgtg gagtgggagt ccaacggcca gcccgagaac  1260
aactacaaga ccaccccccc cgtgctggac tccgacggct ccttcttcct ggtgtccaag  1320
ctgaccgtgg acaagtccag gtggcagcag ggcaacgtgt tctcctgctc cgtgatgcac  1380
gaggccctgc acaaccacta cacccagaag tccctgtccc tgtcccccgg caagtaa     1437

SEQ ID NO: 87           moltype = DNA  length = 1437
FEATURE                 Location/Qualifiers
misc_feature            1..1437
                        note = 87
source                  1..1437
                        mol_type = other DNA
                        organism = synthetic construct
SEQUENCE: 87
gacatcgtgc tgacccagtc ccccgtgtcc ctggccgtgc ccctgggcca gagggccacc  60
atctcctgca aggcctccca gtccgtggac tacgacgccg actcctacat gaactggtac  120
cagcagaagc ccggccagcc ccccaagctg ctgatctacg ccgcctccac cctgcactcc  180
ggcatccccg tgaggttctc cggctccggc tccggcaccg acttcaccct gaacatccac  240
cccgtggagg aggaggacgc cgcctcctac tactgccagc agtccaagga ggaccccagg  300
accttcggcg gcggcaccaa gctggagatc aagggaggcg gtggatcagg cggaggtggc  360
tcaggtggag gcggttctga ggtgctgctg cagcagtccg gccccgaggt ggtgaagccc  420
ggcgcctccg tgaagatcac ctgcaaggcc tccggctaca ccttcaccga ctacaacatg  480
gactgggtga agcagtccca cggcaagtcc ctggagtgga tcggcgacat caaccccaac  540
aacggcggca ccctgtacaa ccagaagttc aggggcaggg tgaccctgat cgtggacaag  600
tcctcctcca ccgcctacat ggagctgagg tccctgacct ccgacgacac cgccgtgtac  660
tactgcgcca ggtccgaggt gttctacggc aactacgccg actactgggg ccagggcacc  720
accctgaccg tgtcctccga gcccaagtcc tgcgacaaga cccacacctg ccccccctgc  780
cccgcccccg aggccgccgg cggcccctcc gtgttcctgt tcccccccaa gcccaaggac  840
accctgatga tctccaggac ccccgaggtg acctgcgtgg tggtggacgt gtcccacgag  900
gaccccgagg tgaagttcaa ctggtacgtg gacggcgtgg aggtgcacaa cgccaagacc  960
```

-continued

```
aagcccaggg aggagcagta caactccacc tacagggtgg tgtccgtgct gaccgtgctg  1020
caccaggact ggctgaacgg caaggagtac aagtgcaagg tgtccaacaa ggccctgccc  1080
gccccccatcg agaagaccat ctccaaggcc aagggccagc ccagggagcc ccaggtgtgc  1140
accctgcccc cctccaggga cgagctgacc aagaaccagg tgtccctgtc ctgcgccgtg  1200
aagggcttct accccctccga catcgccgtg gagtgggagt ccaacggcca gcccgagaac  1260
aactacaaga ccaccccccc cgtgctggac tccgacggct ccttcttcct ggtgtccaag  1320
ctgaccgtgg acaagtccag gtggcagcag ggcaacgtgt tctcctgctc cgtgatgcac  1380
gaggccctgc acaaccacta cacccagaag tccctgtccc tgtcccccgg caagtaa     1437

SEQ ID NO: 88          moltype = DNA  length = 60
FEATURE                Location/Qualifiers
misc_feature           1..60
                       note = 88
source                 1..60
                       mol_type = other DNA
                       organism = synthetic construct
SEQUENCE: 88
atggagaccg acaccctgct gctgtgggtg ctgctgctgt gggtgcccgg ctccaccggc  60
```

BISPECIFIC ANTIBODIES TARGETING CD3 AND B7H6 AND USES OF THE SAME THEREOF

CROSS-REFERENCE TO RELATED APPLICATIONS

This application is a continuation of International Application No. PCT/CN7072/100475, filed on Jun. 22, 2022, which claims priority to Chinese Patent Application No. 202111485404.0, filed on Dec. 7, 2021. The disclosures of the aforementioned applications are hereby incorporated by reference in their entireties.

REFERENCE TO SEQUENCE LISTING

This application contains a sequence listing submitted as an ASCII text file, named "Sequence-Listing.xml" and created on Jul. 6, 2023, with 148 bytes in size. The material in the above-identified ASCII text file is incorporated herein by reference in its entirety.

FIELD

The present disclosure belongs to the field of bio-medicine, and particularly to a bispecific antibody and use thereof, more particularly to a recombinant antibody, an immune cell, a nucleic acid, an expression vector, a recombinant cell, a composition, uses of the above for the manufacture of a medicament, and a kit.

BACKGROUND

Bispecific antibodies are antibodies that specifically bind to two antigenic sites simultaneously. Bispecific antibodies for tumor therapy can be divided into three classes based on their mechanisms, i.e., bispecific antibodies for redirecting effector cells; bispecific antibodies for immunoregulation; bispecific antibodies for targeting tumor cell receptor and dual binding. Among them, antibodies with the redirecting function predominate, and two currently marketed antibodies for tumor therapy are also based on T cell redirecting. Depending upon the characteristics of the bispecific antibodies, they can also be used well in other therapeutic systems, such as dual immunoregulation or targeting two molecules of the same cell membrane.

B7H6 is a type I transmembrane protein belonging to the B7 family, and it contains two immunoglobulin domains. B7H6 is also a ligand for the NK cell activating receptor NKp30. B7H6 is expressed on a variety of tumor cells, but mRNA of B7H6 is not detected in normal tissues and healthy peripheral blood mononuclear cells of humans. In an inflammatory environment, certain proinflammatory cytokines such as IL-1β and TNT can stimulate the up-regulation of B7H6 expression by $CD14^+$ and $CD16^+$ mononuclear cells and neutrophils. The tumor expression profile of B7H6 is very wide, including leukemia, lymphoma, colorectal cancer, non-small cell lung cancer, breast cancer, ovarian cancer, gastric cancer, and liver cancer. B7H6 expression is associated with metastasis of some cancers. However, the role of B7H6 most tumors is currently unclear. Currently, although B7H6 is expressed in a variety of tumors, there are few tumor therapies targeting this molecule. Researchers have developed a bispecific antibody against B7H6, constructed in the form of BiTE, which does not contain the constant region of the native antibody, resulting an excessively short half-life of this molecule in vivo and thus limiting its use.

CD3 is an important target in T cell-based redirecting bispecific antibodies. Unlike immuno-checkpoint blocking antibodies, CD3-related bispecific antibodies can mediate T cell activation bypassing TCR and peptide-major histocompatibility complex (pMHC), but the molecular functioning process in the synapse is very similar to the classical TCR-pMHC interaction. The activity of bispecific antibodies is influenced by the affinity of CD3, which has a better pro-killing effect in in vitro experiments, but a lethal cytokine release syndrome toxicity in vivo, which is very similar to the chimeric antigen receptor (CAR) T cell toxicity. It has also been found that CD3 antibody sequences with very low affinity can also effectively stimulate T cell activation after the construction of bispecific antibodies. When the CD3 antibody with an affinity in the appropriate range (200±78 nM) and the tumor target-associated antibody is of high affinity, the bispecific antibody promotes that T cells are selectively located to the tumor site rather than to the peripheral circulation, avoiding systemic activation. Therefore, the development of highly targeted bispecific antibodies is of great value to the prevention and treatment of tumors.

SUMMARY

The present disclosure is based on the Applicant's discovery and recognition of the following facts and problems.

In the present disclosure, the Applicant carried out various combinations and screening for CD3 and B7H6 antigen-binding fragments and designed recombinant bispecific antibodies, which can specifically bind to CD3 and B71-16, thereby targeting a B7H6 molecule to the vicinity of tumor cells. The recombinant bispecific antibodies promote $CD3^+$ lymphocytes to form immunological synapses with tumor cells by binding to the B7H6 molecules on the mirror cells, thereby activating, the lymphocytes to kill the $B7H6^+$ tumor cells. The recombinant bispecific antibodies have high CD3- and B7H6-binding activities and high anti-tumor activity.

Thus, in a first aspect of the present disclosure, the present disclosure provides a recombinant antibody. According to an embodiment of the present disclosure, the recombinant antibody includes a CDR sequence selected from at least one of the following sequences, or an amino acid sequence having at least 95% identity thereto: CD3 antibody variable region CDR sequences: SEQ ID NO: 1 to SEQ ID NO: 6; and B7H6 antibody variable region CDR sequences: SEQ ID NO: 7 to SEQ ID NO: 12. The recombinant antibody according to the embodiments of the present disclosure can effectively bind to CD3 and B7H6, has strong in vivo and in vitro binding activities, a long in vivo half-life, and has a significant anti-tumor effect.

(SEQ ID NO: 1)
RASQDIRNYLN.

(SEQ ID NO: 2)
YTSRLES.

(SEQ ID NO: 3)
QQGNTLPWT.

(SEQ ID NO: 4)
GYTMN.

-continued (SEQ ID NO: 5)
LINPYKGVSTYNQKFKD.

(SEQ ID NO: 6)
SGYYGDSDWYFDV.

(SEQ ID NO: 7)
KASQSVDYDGDSYMN.

(SEQ ID NO: 8)
AASTLHS.

(SEQ ID NO: 9)
QQSKEDPRT.

(SEQ ID NO: 10)
DYNMD.

(SEQ ID NO: 11)
DINPNNGGTLYNQKFRG.

(SEQ ID NO: 12)
SEVFYGNYADY.

In a second aspect of the present disclosure, the present disclosure provides a recombinant antibody. According to an embodiment of the present disclosure, the recombinant antibody has an amino acid sequence as set forth in SEQ ID NO: 49 and SEQ ID NO: 63. The recombinant antibody according to the embodiments of the present disclosure can effectively bind to CD3 and B7H6 has strong in vivo and in vitro binding activities, a long in vivo half-life, and has a significant anti-tumor effect.

(SEQ ID NO: 49)
MDIQMTQSPSSLSASVGDRVTITCRASQDIRNYLNWYQQKPGKAPKLLI

YYTSRLESGVPSRFSGSGSGTDYTLTISSLQPEDFATYYCQQGNTLPWT

FGQGTKVEIKGGGGSGGGGSGGGGSEVQLVESGGGLVQPGGSLRLSCAA

SGYSFTGYTMNWVRQAPGKGLEWVALINPYKGVSTYNQKFKDRFTISVD

KSKNTAYLQMNSLRAEDTAVYYCARSGYYGDSDWYFDVWGQGTLVTVSS

EPKSCDKTHTCPPCPAPEAAGGPSVFLFPPKPKDTLMISRTPEVTCVVV

DVSHEDPEVKFNWYVDGVEVHNAKTKPREEQYNSTYRVVSVLTVLHQDW

LNGKEYKCKVSNKALPAPIEKTISKAKGQPREPQVYTLPPCRDELTKNQ

VSLWCLVKGFYPSDIAVEWESNGQPENNYKTTPPVLDSDGSFFLYSKLT

VDKSRWQQGNVFSCSVMHEALHNHYTQKSLSLSPGK.

(SEQ ID NO: 63)
DIVLTQTPLSLSVTPGQPASISCKASQSVDYDGDSYMNWYLQKPGQPPQ

LLIYAASTLHSGIPDRFSGSGSGTDFTLKISRVEAEDVGVYYCQQSKED

PRTFGQGTKLEIKGGGGSGGGGSGGGGSEVQLVQSGAEVKKPGASVKVS

CKASGYTFTDYNMDWVRQAPGQGLEWIGDINPNNGGTLYNQKFRGRVTL

TVDTSISTAYMELSRLRSDDTAVYYCARSEVFYGNYADYWGQGTTVTVS

SEPKSCDKTHTCPPCPAPEAAGGPSVFLFPPKPKDTLMISRTPEVTCVV

VDVSHEDPEVKFNWYVDGVEVHNAKTKPREEQYNSTYRVVSVLTVLHQD

WLNGKEYKCKVSNKALPAPIEKTISKAKGQPREPQVCTLPPSRDELTKN

QVSLSCAVKGFYPSDIAVEWESNGQPENNYKTTPPVLDSDGSFFLVSKL

TVDKSRWQQGNVFSCSVMHEALHNHYTQKSLSLSPGK.

In a third aspect of the present disclosure, the present disclosure provides a nucleic acid. According to an embodiment of the present disclosure, the nucleic acid encodes the recombinant antibody according to the first aspect. The recombinant antibody encoded by the nucleic acid according to the embodiments of the present disclosure can effectively bind to CD3 and B7H6, has strong in vivo and in vitro binding activities, a long in vivo half-life, and a significant anti-tumor effect.

In a fourth aspect of the present disclosure, the present disclosure provides an expression vector. According to an embodiment of the present disclosure, the expression vector carries the nucleic acid molecule according to the third aspect. The expression vector may include an optional control sequence operably linked to the nucleic acid molecule. The control sequence is one or more control sequences that direct expression of the nucleic acid molecule in a host. The expression vector proposed in the embodiments of the present disclosure can efficiently and massively express the recombinant antibody in suitable host cells, and thus it can be effectively used for specific treatment or prevention of tumors, and particularly tumors expressing B7H6.

In a fifth aspect of the present disclosure, the present disclosure provides a recombinant cell. According to an embodiment of the present disclosure, the recombinant cell carries the nucleic acid molecule according to the third aspect, the expression vector according to the fourth aspect, or the recombinant antibody according to the first aspect. The recombinant cell is obtained by transfecting or transforming the expression vector. According to an embodiment of the present disclosure, the recombinant cell can efficiently and massively express the recombinant antibody under suitable conditions, and the recombinant cell can be effectively used for specific treatment or prevention of a tumor, particularly a tumor expressing B7H6.

In a sixth aspect of the present disclosure, the present disclosure provides a composition. According, to an embodiment of the present disclosure, the composition includes the recombinant antibody according to the first or second aspect, the nucleic acid molecule according to the third aspect, the expression vector according to the fourth aspect, or the recombinant cell according to the fifth aspect. As described above, the recombinant antibody according to the embodiments of the present disclosure can effectively bind to CD3 or B7H6 protein molecules, thereby specifically recognizing tumor cells highly expressing B7H6 and promoting selective localization of T cells to the tumor site rather than in the peripheral circulation, avoiding systemic activation. The medicament including the recombinant antibody also has significant effects for treating or preventing the tumors expressing B7H6, with higher safety and fewer side effects.

In a seventh aspect of the present disclosure, the present disclosure provides use of the recombinant antibody according to the first or second aspect, the nucleic acid molecule according to the third aspect, the expression vector according to the fourth aspect, the recombinant cell according to the fifth aspect, or the composition according to the sixth aspect for the manufacture of a medicament. According to an embodiment of the present disclosure, the medicament is used for the treatment or prevention of tumors. As described above, the recombinant antibody according to the embodiments of the present disclosure can effectively bind to CD3 and B7H6 protein, thereby specifically recognizing tumor cells highly expressing the B7H6. Thus, the medicament prepared with the recombinant antibody and the corresponding series of substances also has significant effects for treating or preventing tumors expressing B7H6, with the medicament has higher safety and fewer side effects.

In an eighth aspect of the present disclosure, the present disclosure provides a medicament. According to an embodiment of the present disclosure, the medicament includes the recombinant antibody according to the first or second aspect, the nucleic acid molecule according to the third aspect, the expression vector according to the fourth aspect, or the recombinant cell according to the fifth aspect or the composition of the sixth aspect. The medicament is used for treating or preventing cancer. As described above, the recombinant antibody according to the embodiments of the present disclosure can effectively bind to CD3 and B7H6 protein, thereby specifically recognizing tumor cells highly expressing the B7H6. Thus, the medicament prepared using the recombinant antibody and the corresponding series of substances also has significant effects for treating or preventing rumors expressing B7H6, with higher safety and fewer side effects.

In a ninth aspect of the present disclosure, the present disclosure provides a kit. According to an embodiment of the present disclosure, the kit includes the recombinant antibody according to the first or second aspect. The antibody according to the embodiments of the present disclosure can effectively bind to CD3 and B7H6 protein molecules, and thus it can specifically recognize tumor cells specifically high expressing the B7H6. Therefore, the recombinant antibody can be used for the preparation of a kit for diagnosing or detecting at least one of rectal cancer, non-small cell lung cancer, breast cancer, and liver cancer. The kit can be used for scientific studies such as qualitative or quantitative detection of CD3 and/or B7H6 protein molecules in a biological sample.

Additional aspects and advantages of the present disclosure will be provided in part in the following description and will be in part obvious from the following description, or may be learned by practice of the present disclosure.

BRIEF DESCRIPTION OF DRAWINGS

The foregoing and/or additional aspects and advantages of the present disclosure will become apparent and readily appreciated from the following description of the embodiments, taken in conjunction with the accompanying drawings of which.

DETAILED DESCRIPTION

Figure 1:
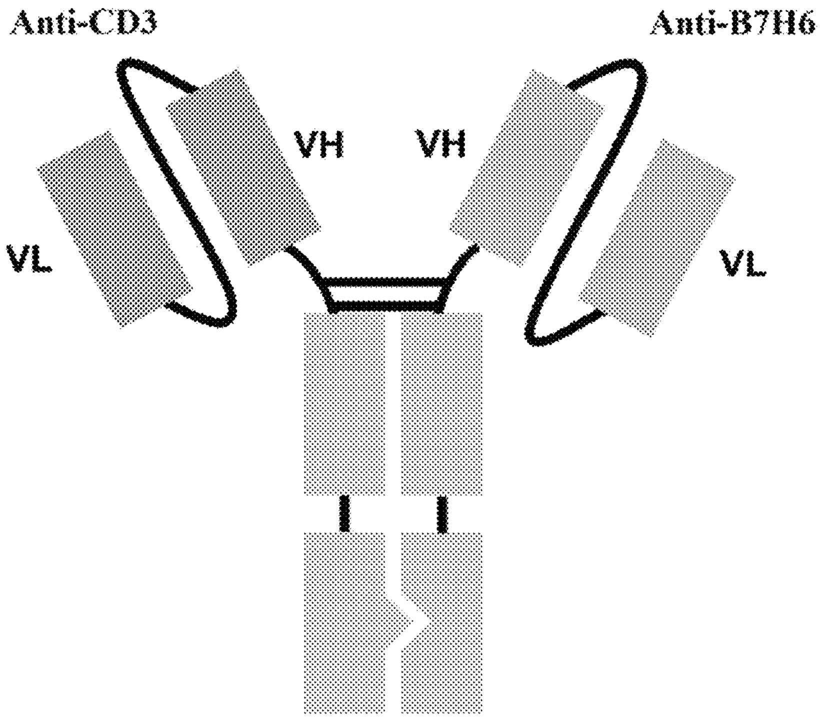
FIG. 1 is a schematic structural diagram of a recombinant bispecific antibody according to an embodiment of the present disclosure.

Embodiments of the present disclosure are described in detail below, and examples of the embodiments are illustrated in the accompanying drawings. The embodiments described below with reference to the accompanying drawings are illustrative and intended to explain the present disclosure, rather than limiting the present disclosure.

Furthermore, the terms such as "first" and "second" are used for descriptive purposes only and are not to be construed as indicating or implying relative importance or implicitly indicating the number of technical features indicated. Thus, a feature defined as "first" or "second" may explicitly or implicitly include at least one such feature. In the description of the present disclosure, the meaning of "plurality" is at least two, e.g., two, three, etc. unless specifically and specifically limited otherwise.

Recombinant Antibody

In a first aspect of the present disclosure, the present disclosure provides a recombinant antibody. According to some specific embodiments of the present disclosure, the recombinant antibody includes a first antigen-binding region for binding to CD3 and a second antigen-binding region for specifically binding to B7H6. The recombinant antibody according to the embodiments of the present disclosure can effectively bind to CD3 on T cells and B7H6 on tumor cells, have a strong in vivo and in vitro binding activities and a long in vivo half-life and the recombinant antibody can form cell synapses by simultaneously binding to T cells and tumor cells, thereby having a significant and-tumor effect.

According to some specific embodiments of the present disclosure, the above-mentioned recombinant antibody may further include at least one of the following additional technical features.

According to some specific embodiments of the present disclosure, the recombinant antibody includes a CDR sequence selected from at least one of the following sequences, or an amino acid sequence having at least 95% identity thereto: CD3 antibody variable region CDR sequences: SEQ ID NO: 1 to SEQ ID NO: 6; and B7H6 antibody variable region CDR sequences: SEQ ID NO: 7 to SEQ ID NO: 12. The recombinant antibody according to the embodiments of the present disclosure can effectively bind to CD3 and B7H6, has strong in vivo and in vitro binding activities, a long in vivo half-life, and a significant anti-tumor effect.

(SEQ ID NO: 1)
RASQDIRNYLN.

(SEQ ID NO: 2)
YTSRLES.

(SEQ ID NO: 3)
QQGNTLPWT.

(SEQ ID NO: 4)
GYTMN.

(SEQ ID NO: 5)
LINPYKGVSTYNQKFKD.

(SEQ ID NO: 6)
SGYYGDSDWYFDV.

(SEQ ID NO: 7)
KASQSVDYDGDSYMN.

(SEQ ID NO: 8)
AASTLHS.

(SEQ ID NO: 9)
QQSKEDPRT.

(SEQ ID NO: 10)
DYNMD.

-continued (SEQ ID NO: 11)
DINPNNGGTLYNQKFRG.

(SEQ ID NO: 12)
SEVFYGNYADY.

According to some specific embodiments of the present disclosure, the recombinant antibody includes CD3 antibody variable regions. The CD3 antibody variable regions include a light chain variable region as set forth in SEQ ID NO: 13 and a heavy chain variable region as set forth in SEQ ID NO: 14; or an amino acid sequence having at least 70%, at least 75%, at least 80%, at least 85%, at least 90%, at least 95%, or at least 99% identity to an amino acid sequence as set forth in SEQ ID NO: 13, and an amino acid sequence having at least 70%, at least 75%, at least 80%, at least 85%, at least 90%, at least 95%, or at least 99% identity to an amino acid sequence as set forth in SEQ ID NO: 14.

(SEQ ID NO: 13)
MDIQMTQSPSSLSASVGDRVTITCRASQDIRNYLNWYQQKPGKAPKLLI
YYTSRLESGVPSRFSGSGSGTDYTLTISSLQPEDFATYYCQQGNTLPWT
FGQGTKVEIK.

(SEQ ID NO: 14)
EVQLVESGGGLVQPGGSLRLSCAASGYSFTGYTMNWVRQAPGKGLEWVA
LINPYKGVSTYNQKFKDRFTISVDKSKNTAYLQMNSLRAEDTAVYYCAR
SGYYGDSDWYFDVWGQGTLVTVSS.

According to some specific embodiments of the present disclosure, the antibody includes B7H6 antibody variable regions. The B7H6 antibody variable regions include: a light chain variable region as set forth in SEQ ID NO: 20 and a heavy chain variable region of the amino acid sequence as set forth in SEQ ID NO: 23; or an amino acid sequence having at least 70%, at least 75%, at least 80%, at least 85%, at least 90%, at least 95%, or at least 99% identity to an amino acid sequence as set forth in SEQ ID NO: 20, and an amino acid sequence having at least 70%, at least 75%, at least 80%, at least 85%, at least 90%, at least 95%, or at least 99% identity to an amino acid sequence as set forth in SEQ ID NO: 23.

(SEQ ID NO: 20)
DIVLTQTPLSLSVTPGQPASISCKASQSVDYDGDSYMNWYLQKPGQPPQ
LLIYAASTLHSGIPDRFSGSGSGTDFTLKISRVEAEDVGVYYCQQSKED
PRTFGQGTKLEIK.

(SEQ ID NO: 23)
EVQLVQSGAEVKKPGASVKVSCKASGYTFTDYNMDWVRQAPGQGLEWIG
DINPNNGGTLYNQKFRGRVTLTVDTSISTAYMELSRLRSDDTAVYYCAR
SEVFYGNYADYWGQGTTVTVSS.

According to some specific embodiments of the present disclosure, the B7H6 antibody variable regions include: a light chain variable region as set forth in SEQ ID NO: 16 and a heavy chain variable region of the amino acid sequence as set forth in SEQ ID NO: 22; or an amino acid sequence having at least 70%, at least 75%, at least 80%, at least 85%, at least 90%, at least 95%, or at least 99% identity to an amino acid sequence as set forth in SEQ ID NO: 16, and an amino acid sequence having at least 70%, at least 75%, at least 80%, at least 85%, at least 90%, at least 95%, or at least 99% identity to an amino acid sequence as set forth in SEQ ID NO: 22.

According to some specific embodiments of the present disclosure, the B7H6 antibody variable regions include: a light chain variable region as set forth in SEQ ID NO: 16 and a heavy chain variable region of the amino acid sequence as set forth in SEQ ID NO: 23; or an amino acid sequence having at least 70%, at least 75%, at least 80%, at least 85%, at least 90%, at least 95%, or at least 99% identity to an amino acid sequence as set forth in SEQ ID NO: 16, and an amino acid sequence having at least 70%, at least 75%, at least 80%, at least 85%, at least 90%, at least 95%, or at least 99% identity to an amino acid sequence as set forth in SEQ ID NO: 23.

According to some specific embodiments of the present disclosure, the B7H6 antibody variable regions include: a light chain variable region as set forth in SEQ ID NO: 16 and a heavy chain variable region of the amino acid sequence as set forth in SEQ ID NO: 24; or an amino acid sequence having at least 70%, at least 75%, at least 80%, at least 85%, at least 90%, at least 95%, or at least 99% identity to an amino acid sequence as set forth in SEQ ID NO: 16, and an amino acid sequence having at least 70%, at least 75%, at least 80%, at least 85%, at least 90%, at least 95%, or at least 99% identity to an amino acid sequence as set forth in SEQ ID NO: 24.

According to some specific embodiments of the present disclosure, the B7H6 antibody variable regions include: a light chain variable region as set forth in SEQ ID NO: 16 and a heavy chain variable region of the amino acid sequence as set forth in SEQ ID NO: 25; or an amino acid sequence having at least 70%, at least 75%, at least 80%, at least 85%, at least 90%, at least 95%, or at least 99% identity to an amino acid sequence as set forth in SEQ ID NO: 16, and an amino acid sequence having at least 70%, at least 75%, at least 80%, at least 85%, at least 90%, at least 95%, or at least 99% identity to an amino acid sequence as set forth in SEQ ID NO: 25.

According to some specific embodiments of the present disclosure, the B7H6 antibody variable regions include: a light chain variable region as set forth in SEQ ID NO: 17 and a heavy chain variable region of the amino acid sequence as set forth in SEQ ID NO: 22; or an amino acid sequence having at least 70%, at least 75%, at least 80%, at least 85%, at least 90%, at least 95%, or at least 99% identity to an amino acid sequence as set forth in SEQ ID NO: 17, and an amino acid sequence having at least 70%, at least 75%, at least 80%, at least 85%, at least 90%, at least 95%, or at least 99% identity to an amino acid sequence as set forth in SEQ ID NO: 22.

According to some specific embodiments of the present disclosure, the B7H6 antibody variable regions include: a light chain variable region as set forth in SEQ ID NO: 17 and a heavy chain variable region of the amino acid sequence as set forth in SEQ ID NO: 23; or an amino acid sequence having at least 70%, at least 75%, at least 80%, at least 85%, at least 90%, at least 95%, or at least 99% identity to an amino acid sequence as set forth in SEQ ID NO: 17, and an amino acid sequence having at least 70%, at least 75%, at least 80%, at least 85%, at least 90%, at least 95%, or at least 99% identity to an amino acid sequence as set forth in SEQ ID NO: 23.

According to some specific embodiments of the present disclosure, the B7H6 antibody variable regions include: a light chain variable region as set forth in SEQ ID NO: 17 and a heavy chain variable region of the amino acid sequence as set forth in SEQ ID NO: 24; or an amino acid sequence having at least 70%, at least 75%, at least 80%, at least 85%, at least 90%, at least 95%, or at least 99% identity to an amino acid sequence as set forth in SEQ ID NO: 17, and an amino acid sequence having at least 70%, at least 75%, at least 80%, at least 85%, at least 90%, at least 95%, or at least 99% identity to an amino acid sequence as set forth in SEQ ID NO: 24.

According to some specific embodiments of the present disclosure, the B7H6 antibody variable regions include: a light chain variable region as set forth in SEQ ID NO: 17 and a heavy chain variable region of the amino acid sequence as set forth in SEQ ID NO: 25; or an amino acid sequence having at least 70%, at least 75%, at least 80%, at least 85%, at least 90%, at least 95%, or at least 99% identity to an amino acid sequence as set forth in SEQ ID NO: 17, and an amino acid sequence having at least 70%, at least 75%, at least 80%, at least 85%, at least 90%, at least 95%, or at least 99% identity to an amino acid sequence as set forth in SEQ ID NO: 25.

According to some specific embodiments of the present disclosure, the B7H6 antibody variable regions include: a light chain variable region as set forth in SEQ ID NO: 19 and a heavy chain variable region of the amino acid sequence as set forth in SEQ ID NO: 22; or an amino acid sequence having at least 70%, at least 75%, at least 80%, at least 85%, at least 90%, at least 95%, or at least 99% identity to an amino acid sequence as set forth in SEQ ID NO: 19, and an amino acid sequence having at least 70%, at least 75%, at least 80%, at least 85%, at least 90%, at least 95%, or at least 99% identity to an amino acid sequence as set forth in SEQ ID NO: 22.

According to some specific embodiments of the present disclosure, the B7H6 antibody variable regions include: a light chain variable region as set forth in SEQ ID NO: 19 and a heavy chain variable region of the amino acid sequence as set forth in SEQ ID NO: 23; or an amino acid sequence having at least 70%, at least 75%, at least 80%, at least 85%, at least 90%, at least 95%, or at least 99% identity to an amino acid sequence as set forth in SEQ ID NO: 19, and an amino acid sequence having at least 70%, at least 75%, at least 80%, at least 85%, at least 90%, at least 95%, or at least 99% identity to an amino acid sequence as set forth in SEQ ID NO: 23.

According to some specific embodiments of the present disclosure, the B7H6 antibody variable regions include: a light chain variable region as set forth in SEQ ID NO: 19 and a heavy chain variable region of the amino acid sequence as set forth in SEQ ID NO: 24; or an amino acid sequence having at least 70%, at least 75%, at least 80%, at least 85%, at least 90%, at least 95%, or at least 99% identity to an amino acid sequence as set forth in SEQ ID NO: 19, and an amino acid sequence having at least 70%, at least 75%, at least 80%, at least 85%, at least 90%, at least 95%, or at least 99% identity to an amino acid sequence as set forth in SEQ ID NO: 24.

According to some specific embodiments of the present disclosure, the B7H6 antibody variable regions include: a light chain variable region as set forth in SEQ ID NO: 19 and a heavy chain variable region of the amino acid sequence as set forth in SEQ ID NO: 25; or an amino acid sequence having at least 70%, at least 75%, at least 80%, at least 85%, at least 90%, at least 95%, or at least 99% identity to an amino acid sequence as set forth in SEQ ID NO: 19, and an amino acid sequence having at least 70%, at least 75%, at least 80%, at least 85%, at least 90%, at least 95%, or at least 99% identity to an amino acid sequence as set forth in SEQ ID NO: 25.

According to some specific embodiments of the present disclosure, the B7H6 antibody variable regions include: a light chain variable region as set forth in SEQ ID NO: 20 and a heavy chain variable region of the amino acid sequence as set forth in SEQ ID NO: 22; or an amino acid sequence having at least 70%, at least 75%, at least 80%, at least 85%, at least 90%, at least 95%, or at least 99% identity to an amino acid sequence as set forth in SEQ ID NO: 20, and an amino acid sequence having at least 70%, at least 75%, at least 80%, at least 85%, at least 90%, at least 95%, or at least 99% identity to an amino acid sequence as set forth in SEQ ID NO: 22.

According to some specific embodiments of the present disclosure, the B7H6 antibody variable regions include: a light chain variable region as set forth in SEQ ID NO: 20 and a heavy chain variable region of the amino acid sequence as set forth in SEQ ID NO: 24; or an amino acid sequence having at least 70%, at least 75%, at least 80%, at least 85%, at least 90%, at least 95%, or at least 99% identity to an amino acid sequence as set forth in SEQ ID NO: 20, and an amino acid sequence having at least 70%, at least 75%, at least 80%, at least 85%, at least 90%, at least 95%, or at least 99% identity to an amino acid sequence as set forth in SEQ ID NO: 24.

According to some specific embodiments of the present disclosure, the B7H6 antibody variable regions include: a light chain variable region as set forth in SEQ ID NO: 20 and a heavy chain variable region of the amino acid sequence as set forth in SEQ ID NO: 25; or an amino acid sequence having at least 70%, at least 75%, at least 80%, at least 85%, at least 90%, at least 95%, or at least 99% identity to an amino acid sequence as set forth in SEQ ID NO: 20, and an amino acid sequence having at least 70%, at least 75%, at least 80%, at least 85%, at least 90%, at least 95%, or at least 99% identity to an amino acid sequence as set forth in SEQ ID NO: 25.

According to some specific embodiments of the present disclosure, the B7H6 antibody variable regions include: a light chain variable region as set forth in SEQ ID NO: 15 and a heavy chain variable region of the amino acid sequence as set forth in SEQ ID NO: 26; or an amino acid sequence having at least 70%, at least 75%, at least 80%, at least 85%, at least 90%, at least 95%, or at least 99% identity to an amino acid sequence as set forth in SEQ ID NO: 15, and an amino acid sequence having at least 70%, at least 75%, at least 80%, at least 85%, at least 90%, at least 95%, or at least 99% identity to an amino acid sequence as set forth in SEQ ID NO: 26.

According to some specific embodiments of the present disclosure, the B7H6 antibody variable regions include: a light chain variable region as set forth In SEQ ID NO: 18 and a heavy chain variable region of the amino acid sequence as set forth in SEQ ID NO: 21 or an amino acid sequence having at least 70%, at least 75%, at least 80%, at least 85%, at least 90%, at least 95%, or at least 99% identity to an amino acid sequence as set forth in SEQ ID NO: 18, and an amino acid sequence having at least 70%, at least 75%, at least 80%, at least 85%, at least 90%, at least 95%, or at least 99% identity to an amino acid sequence as set forth in SEQ ID NO: 21.

```
                                            (SEQ ID NO: 15)
DIVLTQSPVSLAVPLGQRATISCKASQSVDYDGDSYMNWYQQKPGQPPK

LLIYAASTLHSGIPVRFSGSGSGTDFTLNIHPVEEEDAASYYCQQSKED

PRTFGGGTKLEIK.

                                            (SEQ ID NO: 16)
DIVLTQSPDSLAVSLGERATINCKASQSVDYDGDSYMNWYQQKPGQPPK

LLIYAASTLHSGVPDRFSGSGSGTDFTLTISSLQAEDVAVYYCQQSKED

PRTFGQGTKLEIK.

                                            (SEQ ID NO: 17)
DIVLTQSPDSLAVSLGERATINCKASQSVDYDGDSYMNWYQQKPGQPPK

LLIYAASTLHSGIPDRFSGSGSGTDFTLTISSLQAEDVAVYYCQQSKED

PRTFGQGTKLEIK.

                                            (SEQ ID NO: 18)
DIVLTQSPVSLAVPLGQRATISCKASQSVDYDADSYMNWYQQKPGQPPK

LLIYAASTLHSGIPVRFSGSGSGTDFTLNIHPVEEEDAASYYCQQSKED

PRTFGGGTKLEIK.

                                            (SEQ ID NO: 19)
DIVLTQTPLSLSVTPGQPASISCKASQSVDYDGDSYMNWYLQKPGQPPQ

LLIYAASTLHSGVPDRFSGSGSGTDFTLKISRVEAEDVGVYYCQQSKED

PRTFGQGTKLEIK.

                                            (SEQ ID NO: 21)
EVLLQQSGPEVVKPGASVKITCKASGYTFTDYNMDWVKQSHGKSLEWIG

DINPNNGGTLYNQKFRGRVTLIVDKSSSTAYMELRSLTSDDTAVYYCAR

SEVFYGNYADYWGQGTTLTVSS.

                                            (SEQ ID NO: 22)
EVQLVQSGAEVKKPGASVKVSCKASGYTFTDYNMDWVRQAPGQGLEWMG

DINPNNGGTLYNQKFRGRVTMTVDTSISTAYMELSRLRSDDTAVYYCAR

SEVFYGNYADYWGQGTTVTVSS.

                                            (SEQ ID NO: 24)
EVQLVQSGAEVKKPGASVKVSCKASGYTFTDYNMDWVRQAPGQGLEWIG

DINPNNGGTLYNQKFRGRVTLTVDKSISTAYMELSRLRSDDTAVYYCAR

SEVFYGNYADYWGQGTTVTVSS.

                                            (SEQ ID NO: 25)
EVQLVQSGAEVKKPGASVKVSCKASGYTFTDYNMDWVRQAPGKGLEWIG

DINPNNGGTLYNQKFRGRVTLTVDKSISTAYMELSRLRSDDTAVYYCAR

SEVFYGNYADYWGQGTTVTVSS.

                                            (SEQ ID NO: 26)
EVLLQQSGPEVVKPGASVKITCKASGYTFTDYNMDWVKQSHGKSLEWIG

DINPNNAGTLYNQKFRGRVTLIVDKSSSTAYMELRSLTSDDTAVYYCAR

SEVFYGNYADYWGQGTTLTVSS.
```

According to some specific embodiments of the present disclosure, the recombinant antibody further includes a linker peptide.

According to some specific embodiments of the present disclosure, the linker peptide has an amino acid sequence as set forth in SEQ ID NO: 46.

```
                                    (SEQ ID NO: 46)
GGGGSGGGGSGGGGS.
```

According to some specific embodiments of the present disclosure, an N-end of the linker peptide is linked to a C-end of an CD3 antibody light chain variable region, and a C-end of the linker peptide is linked to an N-end of an CD3 antibody heavy chain variable region.

According to some specific embodiments of the present disclosure, an N-end of the linker peptide is linked to a C-end of a B7H6 light chain variable region, and a C-end of the linker peptide is linked to an N-end of the B7H6 heavy chain variable region.

According to some specific embodiments of the present disclosure, the recombinant antibody further includes a first Fc region and a second Fc region; at least a portion of the first Fc region and the second Fc region is derived from at least one of a murine antibody, a human antibody, a primate antibody, or a mutant thereof.

According to some specific embodiments of the present disclosure, at least a portion of the first Fc region and the second Fc region is derived from human IgG or a mutant thereof.

According to some specific embodiments of the present disclosure, at least a portion of the first Fc region and the second Fc region is derived from human IgG1 or a mutant thereof.

According to some specific embodiments of the present disclosure, the first Fc region has at least one of S384C mutation and T396W mutation as compared to a Fc region of wild-type IgG1.

According to some specific embodiments of the present disclosure, the second Fc region has at least one of Y380C mutation, T3978 mutation, T399A mutation, and Y408V mutation as compared to the Fc region of wild-type IgG1.

According to some specific embodiments of the present disclosure, the first Fc region has an amino acid sequence as set forth in SEQ ID NO: 47, and the second Fc region has an amino acid sequence as set forth in SEQ ID NO: 48.

```
                                    (SEQ ID NO: 47)
EPKSCDKTHTCPPCPAPEAAGGPSVFLFPPKPKDTLMISRTPEVTCVVV

DVSHEDPEVKFNWYVDGVEVHNAKTKPREEQYNSTYRVVSVLTVLHQDW

LNGKEYKCKVSNKALPAPIEKTISKAKGQPREPQVYTLPPCRDELTKNQ

VSLWCLVKGFYPSDIAVEWESNGQPENNYKTTPPVLDSDGSFFLYSKLT

VDKSRWQQGNVFSCSVMHEALHNHYTQKSLSLSPGK.

                                    (SEQ ID NO: 48)
EPKSCDKTHTCPPCPAPEAAGGPSVFLFPPKPKDTLMISRTPEVTCVVV

DVSHEDPEVKFNWYVDGVEVHNAKTKPREEQYNSTYRVVSVLTVLHQDW

LNGKEYKCKVSNKALPAPIEKTISKAKGQPREPQVCTLPPSRDELTKNQ

VSLSCAVKGFYPSDIAVEWESNGQPENNYKTTPPVLDSDGSFFLVSKLT

VDKSRWQQGNVFSCSVMHEALHNHYTQKSLSLSPGK
```

In a second aspect of the present disclosure, the present disclosure provides a recombinant antibody. According to an embodiment of the present disclosure, the recombinant antibody has an amino acid sequence as set forth in SEQ ID NO: 49 and SEQ ID NO: 63. The recombinant antibody according to the embodiments of the present disclosure can effectively bind to CD3 and B7H6, has strong in vivo and in vitro binding activities, a long in vivo half-life, and a significant anti-tumor effect.

```
                                    (SEQ ID NO: 49)
MDIQMTQSPSSLSASVGDRVTITCRASQDIRNYLNWYQQKPGKAPKLLIYY

TSRLESGVPSRFSGSGSGTDYTLTISSLQPEDFATYYCQQGNTLPWTFGQGTKVEIKGG

GGSGGGGSGGGGSEVQLVESGGGLVQPGGSLRLSCAASGYSFTGYTMNWVRQAPGK

GLEWVALINPYKGVSTYNQKFKDRFTISVDKSKNTAYLQMNSLRAEDTAVYYCARSG

YYGDSDWYFDVWGQGTLVTVSSEPKSCDKTHTCPPCPAPEAAGGPSVFLFPPKPKDT

LMISRTPEVTCVVVDVSHEDPEVKFNWYVDGVEVHNAKTKPREEQYNSTYRVVSVL

TVLHQDWLNGKEYKCKVSNKALPAPIEKTISKAKGQPREPQVYTLPPCRDELTKNQV

SLWCLVKGFYPSDIAVEWESNGQPENNYKTTPPVLDSDGSFFLYSKLTVDKSRWQQG

NVFSCSVMHEALHNHYTQKSLSLSPGK.

                                    (SEQ ID NO: 63)
DIVLTQTPLSLSVTPGQPASISCKASQSVDYDGDSYMNWYLQKPGQPPQLL

IYAASTLHSGIPDRFSGSGSGTDFTLKISRVEAEDVGVYYCQQSKEDPRTFGQGTKLEI

KGGGGSGGGGSGGGGSEVQLVQSGAEVKKPGASVKVSCKASGYTFTDYNMDWVR

QAPGQGLEWIGDINPNNGGTLYNQKFRGRVTLTVDTSISTAYMELSRLRSDDTAVYYC

ARSEVFYGNYADYWGQGTTVTVSSEPKSCDKTHTCPPCPAPEAAGGPSVFLFPPKPK

DTLMISRTPEVTCVVVDVSHEDPEVKFNWYVDGVEVHNAKTKPREEQYNSTYRVVS

VLTVLHQDWLNGKEYKCKVSNKALPAPIEKTISKAKGQPREPQVCTLPPSRDELTKNQ
```

-continued

VSLSCAVKGFYPSDIAVEWESNGQPENNYKTTPPVLDSDGSFFLVSKLTVDKSRWQQG

NVFSCSVMHEALHNHYTQKSLSLSPGK.

A Preventive or Therapeutic Composition

In a third aspect of the present disclosure, the present disclosure provides a nucleic acid encoding the recombinant antibody as described above. The recombinant antibody encoded by the nucleic acid according to some specific embodiments of the present disclosure can effectively bind to CD3 and B7H6, has strong in vivo and in vitro binding activities, and a long in vivo half-life, and a significant anti-tumor effect.

According to some specific embodiments of the present disclosure, the nucleic acid has a nucleotide sequence as set forth in SEQ ID NO: 69 and at least one of nucleotide sequences as set forth in SEQ ID NO: 70 to SEQ ID NO: 87.

Nucleotide Sequence Encoding CD3 Antibody (SEQ ID NO: 69)

CAGGCCGTGGTGACCCAGGAGCCCTCCCTGACCGTGTCCCCCGGCGGC

ACCGTGACCCTGACCTGCAGGTCCTCCACCGGCGCCGTGACCACCTCCA

ACTACGCCAACTGGGTGCAGCAGAAGCCCGGCCAGGCCCCCAGGGGCCT

GATCGGCGGCACCAACAAGAGGGCCCCCTGGACCCCCGCCAGGTTCTCC

GGCTCCCTGCTGGGCGGCAAGGCCGCCCTGACCATCACCGGCGCCCAGG

CCGAGGACGAGGCCGACTACTACTGCGCCCTGTGGTACTCCAACCTGTG

GGTGTTCGGCGGCGGCACCAAGCTGACCGTGCTGGGCGGAGGCGGTGGA

TCAGGCGGAGGTGGCTCAGGTGGAGGCGGTTCTGAGGTGCAGCTGGTGG

AGTCCGGCGGCGGCCTGGTGCAGCCCGGCGGCTCCCTGAGGCTGTCCTG

CGCCGCCTCCGGCTTCACCTTCAACACCTACGCCATGAACTGGGTGAGG

CAGGCCCCCGGCAAGGGCCTGGAGTGGGTGGCCAGGATCAGGTCCAAGT

ACAACAACTACGCCACCTACTACGCCGACTCCGTGAAGGACAGGTTCAC

CATCTCCAGGGACGACTCCAAGAACTCCCTGTACCTGCAGATGAACTCC

CTGAAGACCGAGGACACCGCCGTGTACTACTGCGTGAGGCACGGCAACT

TCGGCAACTCCTACGTGTCCTGGTTCGCCTACTGGGGCCAGGGCACCCT

GGTGACCGTGTCCTCCGAGCCCAAGTCCTGCGACAAGACCCACACCTGC

CCCCCCTGCCCCGCCCCCGAGGCCGCCGGCGGCCCCTCCGTGTTCCTGT

TCCCCCCCAAGCCCAAGGACACCCTGATGATCTCCAGGACCCCCGAGGT

GACCTGCGTGGTGGTGGACGTGTCCCACGAGGACCCCGAGGTGAAGTTC

AACTGGTACGTGGACGGCGTGGAGGTGCACAACGCCAAGACCAAGCCCA

GGGAGGAGCAGTACAACTCCACCTACAGGGTGGTGTCCGTGCTGACCGT

GCTGCACCAGGACTGGCTGAACGGCAAGGAGTACAAGTGCAAGGTGTCC

AACAAGGCCCTGCCCGCCCCCATCGAGAAGACCATCTCCAAGGCCAAGG

GCCAGCCCAGGGAGCCCCAGGTGTACACCCTGCCCCCCTGCAGGGACGA

GCTGACCAAGAACCAGGTGTCCCTGTGGTGCCTGGTGAAGGGCTTCTAC

CCCTCCGACATCGCCGTGGAGTGGGAGTCCAACGGCCAGCCCGAGAACA

ACTACAAGACCACCCCCCCCGTGCTGGACTCCGACGGCTCCTTCTTCCT

GTACTCCAAGCTGACCGTGGACAAGTCCAGGTGGCAGCAGGGCAACGTG

-continued

TTCTCCTGCTCCGTGATGCACGAGGCCCTGCACAACCACTACACCCAGA

AGTCCCTGTCCCTGTCCCCCGGCAAGTAA.

Nucleotide Sequence Encoding B7H6-1 Antibody (SEQ ID NO: 70)

GACATCGTGCTGACCCAGTCCCCCGACTCCCTGGCCGTGTCCCTGGGCG

AGAGGGCCACCATCAACTGCAAGGCCTCCCAGTCCGTGGACTACGACGG

CGACTCCTACATGAACTGGTACCAGCAGAAGCCCGGCCAGCCCCCCAAG

CTGCTGATCTACGCCGCCTCCACCCTGCACTCCGGCGTGCCCGACAGGT

TCTCCGGCTCCGGCTCCGGCACCGACTTCACCCTGACCATCTCCTCCCT

GCAGGCCGAGGACGTGGCCGTGTACTACTGCCAGCAGTCCAAGGAGGAC

CCCAGGACCTTCGGCCAGGGCACCAAGCTGGAGATCAAGGGAGGCGGTG

GATCAGGCGGAGGTGGCTCAGGTGGAGGCGGTTCTGAGGTGCAGCTGGT

GCAGTCCGGCGCCGAGGTGAAGAAGCCCGGCGCCTCCGTGAAGGTGTCC

TGCAAGGCCTCCGGCTACACCTTCACCGACTACAACATGGACTGGGTGA

GGCAGGCCCCCGGCCAGGGCCTGGAGTGGATGGGCGACATCAACCCCAA

CAACGGCGGCACCCTGTACAACCAGAAGTTCAGGGGCAGGGTGACCATG

ACCGTGGACACCTCCATCTCCACCGCCTACATGGAGCTGTCCAGGCTGA

GGTCCGACGACACCGCCGTGTACTACTGCGCCAGGTCCGAGGTGTTCTA

CGGCAACTACGCCGACTACTGGGGCCAGGGCACCACCGTGACCGTGTCC

TCCGAGCCCAAGTCCTGCGACAAGACCCACACCTGCCCCCCCTGCCCCG

CCCCCGAGGCCGCCGGCGGCCCCTCCGTGTTCCTGTTCCCCCCCAAGCC

CAAGGACACCCTGATGATCTCCAGGACCCCCGAGGTGACCTGCGTGGTG

GTGGACGTGTCCCACGAGGACCCCGAGGTGAAGTTCAACTGGTACGTGG

ACGGCGTGGAGGTGCACAACGCCAAGACCAAGCCCAGGGAGGAGCAGTA

CAACTCCACCTACAGGGTGGTGTCCGTGCTGACCGTGCTGCACCAGGAC

TGGCTGAACGGCAAGGAGTACAAGTGCAAGGTGTCCAACAAGGCCCTGC

CCGCCCCCATCGAGAAGACCATCTCCAAGGCCAAGGGCCAGCCCAGGGA

GCCCCAGGTGTGCACCCTGCCCCCCTCCAGGGACGAGCTGACCAAGAAC

CAGGTGTCCCTGTCCTGCGCCGTGAAGGGCTTCTACCCCTCCGACATCG

CCGTGGAGTGGGAGTCCAACGGCCAGCCCGAGAACAACTACAAGACCAC

CCCCCCCGTGCTGGACTCCGACGGCTCCTTCTTCCTGGTGTCCAAGCTG

ACCGTGGACAAGTCCAGGTGGCAGCAGGGCAACGTGTTCTCCTGCTCCG

TGATGCACGAGGCCCTGCACAACCACTACACCCAGAAGTCCCTGTCCCT

GTCCCCCGGCAAGTAA.

Nucleotide Sequence Encoding B7H6-2 Antibody (SEQ ID NO: 71)

GACATCGTGCTGACCCAGTCCCCCGACTCCCTGGCCGTGTCCCTGGGCG
AGAGGGCCACCATCAACTGCAAGGCCTCCCAGTCCGTGGACTACGACGG
CGACTCCTACATGAACTGGTACCAGCAGAAGCCCGGCCAGCCCCCCAAG
CTGCTGATCTACGCCGCCTCCACCCTGCACTCCGGCGTGCCCGACAGGT
TCTCCGGCTCCGGCTCCGGCACCGACTTCACCCTGACCATCTCCTCCCT
GCAGGCCGAGGACGTGGCCGTGTACTACTGCCAGCAGTCCAAGGAGGAC
CCCAGGACCTTCGGCCAGGGCACCAAGCTGGAGATCAAGGGAGGCGGTG
GATCAGGCGGAGGTGGCTCAGGTGGAGGCGGTTCTGAGGTGCAGCTGGT
GCAGTCCGGCGCCGAGGTGAAGAAGCCCGGCGCCTCCGTGAAGGTGTCC
TGCAAGGCCTCCGGCTACACCTTCACCGACTACAACATGGACTGGGTGA
GGCAGGCCCCCGGCCAGGGCCTGGAGTGGATCGGCGACATCAACCCCAA
CAACGGCGGCACCCTGTACAACCAGAAGTTCAGGGGCAGGGTGACCCTG
ACCGTGGACACCTCCATCTCCACCGCCTACATGGAGCTGTCCAGGCTGA
GGTCCGACGACACCGCCGTGTACTACTGCGCCAGGTCCGAGGTGTTCTA
CGGCAACTACGCCGACTACTGGGGCCAGGGCACCACCGTGACCGTGTCC
TCCGAGCCCAAGTCCTGCGACAAGACCCACACCTGCCCCCCCTGCCCCG
CCCCCGAGGCCGCCGGCGGCCCCTCCGTGTTCCTGTTCCCCCCCAAGCC
CAAGGACACCCTGATGATCTCCAGGACCCCCGAGGTGACCTGCGTGGTG
GTGGACGTGTCCCACGAGGACCCCGAGGTGAAGTTCAACTGGTACGTGG
ACGGCGTGGAGGTGCACAACGCCAAGACCAAGCCCAGGGAGGAGCAGTA
CAACTCCACCTACAGGGTGGTGTCCGTGCTGACCGTGCTGCACCAGGAC
TGGCTGAACGGCAAGGAGTACAAGTGCAAGGTGTCCAACAAGGCCCTGC
CCGCCCCCATCGAGAAGACCATCTCCAAGGCCAAGGGCCAGCCCAGGGA
GCCCCAGGTGTGCACCCTGCCCCCCTCCAGGGACGAGCTGACCAAGAAC
CAGGTGTCCCTGTCCTGCGCCGTGAAGGGCTTCTACCCCTCCGACATCG
CCGTGGAGTGGGAGTCCAACGGCCAGCCCGAGAACAACTACAAGACCAC
CCCCCCCGTGCTGGACTCCGACGGCTCCTTCTTCCTGGTGTCCAAGCTG
ACCGTGGACAAGTCCAGGTGGCAGCAGGGCAACGTGTTCTCCTGCTCCG
TGATGCACGAGGCCCTGCACAACCACTACACCCAGAAGTCCCTGTCCCT
GTCCCCCGGCAAGTAA.

Nucleotide Sequence Encoding B7H6-3 Antibody (SEQ ID NO: 72)

GACATCGTGCTGACCCAGTCCCCCGACTCCCTGGCCGTGTCCCTGGGCG
AGAGGGCCACCATCAACTGCAAGGCCTCCCAGTCCGTGGACTACGACGG
CGACTCCTACATGAACTGGTACCAGCAGAAGCCCGGCCAGCCCCCCAAG
CTGCTGATCTACGCCGCCTCCACCCTGCACTCCGGCGTGCCCGACAGGT
TCTCCGGCTCCGGCTCCGGCACCGACTTCACCCTGACCATCTCCTCCCT
GCAGGCCGAGGACGTGGCCGTGTACTACTGCCAGCAGTCCAAGGAGGAC
CCCAGGACCTTCGGCCAGGGCACCAAGCTGGAGATCAAGGGAGGCGGTG

-continued

GATCAGGCGGAGGTGGCTCAGGTGGAGGCGGTTCTGAGGTGCAGCTGGT
GCAGTCCGGCGCCGAGGTGAAGAAGCCCGGCGCCTCCGTGAAGGTGTCC
TGCAAGGCCTCCGGCTACACCTTCACCGACTACAACATGGACTGGGTGA
GGCAGGCCCCCGGCCAGGGCCTGGAGTGGATCGGCGACATCAACCCCAA
CAACGGCGGCACCCTGTACAACCAGAAGTTCAGGGGCAGGGTGACCCTG
ACCGTGGACAAGTCCATCTCCACCGCCTACATGGAGCTGTCCAGGCTGA
GGTCCGACGACACCGCCGTGTACTACTGCGCCAGGTCCGAGGTGTTCTA
CGGCAACTACGCCGACTACTGGGGCCAGGGCACCACCGTGACCGTGTCC
TCCGAGCCCAAGTCCTGCGACAAGACCCACACCTGCCCCCCCTGCCCCG
CCCCCGAGGCCGCCGGCGGCCCCTCCGTGTTCCTGTTCCCCCCCAAGCC
CAAGGACACCCTGATGATCTCCAGGACCCCCGAGGTGACCTGCGTGGTG
GTGGACGTGTCCCACGAGGACCCCGAGGTGAAGTTCAACTGGTACGTGG
ACGGCGTGGAGGTGCACAACGCCAAGACCAAGCCCAGGGAGGAGCAGTA
CAACTCCACCTACAGGGTGGTGTCCGTGCTGACCGTGCTGCACCAGGAC
TGGCTGAACGGCAAGGAGTACAAGTGCAAGGTGTCCAACAAGGCCCTGC
CCGCCCCCATCGAGAAGACCATCTCCAAGGCCAAGGGCCAGCCCAGGGA
GCCCCAGGTGTGCACCCTGCCCCCCTCCAGGGACGAGCTGACCAAGAAC
CAGGTGTCCCTGTCCTGCGCCGTGAAGGGCTTCTACCCCTCCGACATCG
CCGTGGAGTGGGAGTCCAACGGCCAGCCCGAGAACAACTACAAGACCAC
CCCCCCCGTGCTGGACTCCGACGGCTCCTTCTTCCTGGTGTCCAAGCTG
ACCGTGGACAAGTCCAGGTGGCAGCAGGGCAACGTGTTCTCCTGCTCCG
TGATGCACGAGGCCCTGCACAACCACTACACCCAGAAGTCCCTGTCCCT
GTCCCCCGGCAAGTAA.

Nucleotide Sequence Encoding B7H6-4 Antibody (SEQ ID NO: 73)

GACATCGTGCTGACCCAGTCCCCCGACTCCCTGGCCGTGTCCCTGGGCG
AGAGGGCCACCATCAACTGCAAGGCCTCCCAGTCCGTGGACTACGACGG
CGACTCCTACATGAACTGGTACCAGCAGAAGCCCGGCCAGCCCCCCAAG
CTGCTGATCTACGCCGCCTCCACCCTGCACTCCGGCGTGCCCGACAGGT
TCTCCGGCTCCGGCTCCGGCACCGACTTCACCCTGACCATCTCCTCCCT
GCAGGCCGAGGACGTGGCCGTGTACTACTGCCAGCAGTCCAAGGAGGAC
CCCAGGACCTTCGGCCAGGGCACCAAGCTGGAGATCAAGGGAGGCGGTG
GATCAGGCGGAGGTGGCTCAGGTGGAGGCGGTTCTGAGGTGCAGCTGGT
GCAGTCCGGCGCCGAGGTGAAGAAGCCCGGCGCCTCCGTGAAGGTGTCC
TGCAAGGCCTCCGGCTACACCTTCACCGACTACAACATGGACTGGGTGA
GGCAGGCCCCCGGCAAGGGCCTGGAGTGGATCGGCGACATCAACCCCAA
CAACGGCGGCACCCTGTACAACCAGAAGTTCAGGGGCAGGGTGACCCTG
ACCGTGGACAAGTCCATCTCCACCGCCTACATGGAGCTGTCCAGGCTGA
GGTCCGACGACACCGCCGTGTACTACTGCGCCAGGTCCGAGGTGTTCTA
CGGCAACTACGCCGACTACTGGGGCCAGGGCACCACCGTGACCGTGTCC

-continued

```
TCCGAGCCCAAGTCCTGCGACAAGACCCACACCTGCCCCCCCTGCCCCG
CCCCCGAGGCCGCCGGCGGCCCCTCCGTGTTCCTGTTCCCCCCCAAGCC
CAAGGACACCCTGATGATCTCCAGGACCCCCGAGGTGACCTGCGTGGTG
GTGGACGTGTCCCACGAGGACCCCGAGGTGAAGTTCAACTGGTACGTGG
ACGGCGTGGAGGTGCACAACGCCAAGACCAAGCCCAGGGAGGAGCAGTA
CAACTCCACCTACAGGGTGGTGTCCGTGCTGACCGTGCTGCACCAGGAC
TGGCTGAACGGCAAGGAGTACAAGTGCAAGGTGTCCAACAAGGCCCTGC
CCGCCCCCATCGAGAAGACCATCTCCAAGGCCAAGGGCCAGCCCAGGGA
GCCCCAGGTGTGCACCCTGCCCCCCTCCAGGGACGAGCTGACCAAGAAC
CAGGTGTCCCTGTCCTGCGCCGTGAAGGGCTTCTACCCCTCCGACATCG
CCGTGGAGTGGGAGTCCAACGGCCAGCCCGAGAACAACTACAAGACCAC
CCCCCCCGTGCTGGACTCCGACGGCTCCTTCTTCCTGGTGTCCAAGCTG
ACCGTGGACAAGTCCAGGTGGCAGCAGGGCAACGTGTTCTCCTGCTCCG
TGATGCACGAGGCCCTGCACAACCACTACACCCAGAAGTCCCTGTCCCT
GTCCCCCGGCAAGTAA.
```

Nucleotide Sequence Encoding B7H6-5 Antibody (SEQ ID NO: 74)

```
GACATCGTGCTGACCCAGTCCCCCGACTCCCTGGCCGTGTCCCTGGGCG
AGAGGGCCACCATCAACTGCAAGGCCTCCCAGTCCGTGGACTACGACGG
CGACTCCTACATGAACTGGTACCAGCAGAAGCCCGGCCAGCCCCCCAAG
CTGCTGATCTACGCCGCCTCCACCCTGCACTCCGGCATCCCCGACAGGT
TCTCCGGCTCCGGCTCCGGCACCGACTTCACCCTGACCATCTCCTCCCT
GCAGGCCGAGGACGTGGCCGTGTACTACTGCCAGCAGTCCAAGGAGGAC
CCCAGGACCTTCGGCCAGGGCACCAAGCTGGAGATCAAGGGAGGCGGTG
GATCAGGCGGAGGTGGCTCAGGTGGAGGCGGTTCTGAGGTGCAGCTGGT
GCAGTCCGGCGCCGAGGTGAAGAAGCCCGGCGCCTCCGTGAAGGTGTCC
TGCAAGGCCTCCGGCTACACCTTCACCGACTACAACATGGACTGGGTGA
GGCAGGCCCCCGGCCAGGGCCTGGAGTGGATGGGCGACATCAACCCCAA
CAACGGCGGCACCCTGTACAACCAGAAGTTCAGGGGCAGGGTGACCATG
ACCGTGGACACCTCCATCTCCACCGCCTACATGGAGCTGTCCAGGCTGA
GGTCCGACGACACCGCCGTGTACTACTGCGCCAGGTCCGAGGTGTTCTA
CGGCAACTACGCCGACTACTGGGGCCAGGGCACCACCGTGACCGTGTCC
TCCGAGCCCAAGTCCTGCGACAAGACCCACACCTGCCCCCCCTGCCCCG
CCCCCGAGGCCGCCGGCGGCCCCTCCGTGTTCCTGTTCCCCCCCAAGCC
CAAGGACACCCTGATGATCTCCAGGACCCCCGAGGTGACCTGCGTGGTG
GTGGACGTGTCCCACGAGGACCCCGAGGTGAAGTTCAACTGGTACGTGG
ACGGCGTGGAGGTGCACAACGCCAAGACCAAGCCCAGGGAGGAGCAGTA
CAACTCCACCTACAGGGTGGTGTCCGTGCTGACCGTGCTGCACCAGGAC
TGGCTGAACGGCAAGGAGTACAAGTGCAAGGTGTCCAACAAGGCCCTGC
CCGCCCCCATCGAGAAGACCATCTCCAAGGCCAAGGGCCAGCCCAGGGA
GCCCCAGGTGTGCACCCTGCCCCCCTCCAGGGACGAGCTGACCAAGAAC
CAGGTGTCCCTGTCCTGCGCCGTGAAGGGCTTCTACCCCTCCGACATCG
CCGTGGAGTGGGAGTCCAACGGCCAGCCCGAGAACAACTACAAGACCAC
CCCCCCCGTGCTGGACTCCGACGGCTCCTTCTTCCTGGTGTCCAAGCTG
ACCGTGGACAAGTCCAGGTGGCAGCAGGGCAACGTGTTCTCCTGCTCCG
TGATGCACGAGGCCCTGCACAACCACTACACCCAGAAGTCCCTGTCCCT
GTCCCCCGGCAAGTAA.
```

Nucleotide Sequence Encoding B7H6-6 Antibody (SEQ ID NO: 75)

```
GACATCGTGCTGACCCAGTCCCCCGACTCCCTGGCCGTGTCCCTGGGCG
AGAGGGCCACCATCAACTGCAAGGCCTCCCAGTCCGTGGACTACGACGG
CGACTCCTACATGAACTGGTACCAGCAGAAGCCCGGCCAGCCCCCCAAG
CTGCTGATCTACGCCGCCTCCACCCTGCACTCCGGCATCCCCGACAGGT
TCTCCGGCTCCGGCTCCGGCACCGACTTCACCCTGACCATCTCCTCCCT
GCAGGCCGAGGACGTGGCCGTGTACTACTGCCAGCAGTCCAAGGAGGAC
CCCAGGACCTTCGGCCAGGGCACCAAGCTGGAGATCAAGGGAGGCGGTG
GATCAGGCGGAGGTGGCTCAGGTGGAGGCGGTTCTGAGGTGCAGCTGGT
GCAGTCCGGCGCCGAGGTGAAGAAGCCCGGCGCCTCCGTGAAGGTGTCC
TGCAAGGCCTCCGGCTACACCTTCACCGACTACAACATGGACTGGGTGA
GGCAGGCCCCCGGCCAGGGCCTGGAGTGGATCGGCGACATCAACCCCAA
CAACGGCGGCACCCTGTACAACCAGAAGTTCAGGGGCAGGGTGACCCTG
ACCGTGGACACCTCCATCTCCACCGCCTACATGGAGCTGTCCAGGCTGA
GGTCCGACGACACCGCCGTGTACTACTGCGCCAGGTCCGAGGTGTTCTA
CGGCAACTACGCCGACTACTGGGGCCAGGGCACCACCGTGACCGTGTCC
TCCGAGCCCAAGTCCTGCGACAAGACCCACACCTGCCCCCCCTGCCCCG
CCCCCGAGGCCGCCGGCGGCCCCTCCGTGTTCCTGTTCCCCCCCAAGCC
CAAGGACACCCTGATGATCTCCAGGACCCCCGAGGTGACCTGCGTGGTG
GTGGACGTGTCCCACGAGGACCCCGAGGTGAAGTTCAACTGGTACGTGG
ACGGCGTGGAGGTGCACAACGCCAAGACCAAGCCCAGGGAGGAGCAGTA
CAACTCCACCTACAGGGTGGTGTCCGTGCTGACCGTGCTGCACCAGGAC
TGGCTGAACGGCAAGGAGTACAAGTGCAAGGTGTCCAACAAGGCCCTGC
CCGCCCCCATCGAGAAGACCATCTCCAAGGCCAAGGGCCAGCCCAGGGA
GCCCCAGGTGTGCACCCTGCCCCCCTCCAGGGACGAGCTGACCAAGAAC
CAGGTGTCCCTGTCCTGCGCCGTGAAGGGCTTCTACCCCTCCGACATCG
CCGTGGAGTGGGAGTCCAACGGCCAGCCCGAGAACAACTACAAGACCAC
CCCCCCCGTGCTGGACTCCGACGGCTCCTTCTTCCTGGTGTCCAAGCTG
ACCGTGGACAAGTCCAGGTGGCAGCAGGGCAACGTGTTCTCCTGCTCCG
TGATGCACGAGGCCCTGCACAACCACTACACCCAGAAGTCCCTGTCCCT
GTCCCCCGGCAAGTAA.
```

Nucleotide Sequence Encoding B7H6-7 Antibody (SEQ ID NO: 76)
GACATCGTGCTGACCCAGTCCCCCGACTCCCTGGCCGTGTCCCTGGGCG
AGAGGGCCACCATCAACTGCAAGGCCTCCCAGTCCGTGGACTACGACGG
CGACTCCTACATGAACTGGTACCAGCAGAAGCCCGGCCAGCCCCCCAAG
CTGCTGATCTACGCCGCCTCCACCCTGCACTCCGGCATCCCCGACAGGT
TCTCCGGCTCCGGCTCCGGCACCGACTTCACCCTGACCATCTCCTCCCT
GCAGGCCGAGGACGTGGCCGTGTACTACTGCCAGCAGTCCAAGGAGGAC
CCCAGGACCTTCGGCCAGGGCACCAAGCTGGAGATCAAGGGAGGCGGTG
GATCAGGCGGAGGTGGCTCAGGTGGAGGCGGTTCTGAGGTGCAGCTGGT
GCAGTCCGGCGCCGAGGTGAAGAAGCCCGGCGCCTCCGTGAAGGTGTCC
TGCAAGGCCTCCGGCTACACCTTCACCGACTACAACATGGACTGGGTGA
GGCAGGCCCCCGGCCAGGGCCTGGAGTGGATCGGCGACATCAACCCCAA
CAACGGCGGCACCCTGTACAACCAGAAGTTCAGGGGCAGGGTGACCCTG
ACCGTGGACAAGTCCATCTCCACCGCCTACATGGAGCTGTCCAGGCTGA
GGTCCGACGACACCGCCGTGTACTACTGCGCCAGGTCCGAGGTGTTCTA
CGGCAACTACGCCGACTACTGGGGCCAGGGCACCACCGTGACCGTGTCC
TCCGAGCCCAAGTCCTGCGACAAGACCCACACCTGCCCCCCCTGCCCCG
CCCCCGAGGCCGCCGGCGGCCCCTCCGTGTTCCTGTTCCCCCCCAAGCC
CAAGGACACCCTGATGATCTCCAGGACCCCCGAGGTGACCTGCGTGGTG
GTGGACGTGTCCCACGAGGACCCCGAGGTGAAGTTCAACTGGTACGTGG
ACGGCGTGGAGGTGCACAACGCCAAGACCAAGCCCAGGGAGGAGCAGTA
CAACTCCACCTACAGGGTGGTGTCCGTGCTGACCGTGCTGCACCAGGAC
TGGCTGAACGGCAAGGAGTACAAGTGCAAGGTGTCCAACAAGGCCCTGC
CCGCCCCCATCGAGAAGACCATCTCCAAGGCCAAGGGCCAGCCCAGGGA
GCCCCAGGTGTGCACCCTGCCCCCCTCCAGGGACGAGCTGACCAAGAAC
CAGGTGTCCCTGTCCTGCGCCGTGAAGGGCTTCTACCCCTCCGACATCG
CCGTGGAGTGGGAGTCCAACGGCCAGCCCGAGAACAACTACAAGACCAC
CCCCCCCGTGCTGGACTCCGACGGCTCCTTCTTCCTGGTGTCCAAGCTG
ACCGTGGACAAGTCCAGGTGGCAGCAGGGCAACGTGTTCTCCTGCTCCG
TGATGCACGAGGCCCTGCACAACCACTACACCCAGAAGTCCCTGTCCCT
GTCCCCCGGCAAGTAA.

Nucleotide Sequence Encoding B7H6-8 Antibody (SEQ ID NO: 77)
GACATCGTGCTGACCCAGTCCCCCGACTCCCTGGCCGTGTCCCTGGGCG
AGAGGGCCACCATCAACTGCAAGGCCTCCCAGTCCGTGGACTACGACGG
CGACTCCTACATGAACTGGTACCAGCAGAAGCCCGGCCAGCCCCCCAAG
CTGCTGATCTACGCCGCCTCCACCCTGCACTCCGGCATCCCCGACAGGT
TCTCCGGCTCCGGCTCCGGCACCGACTTCACCCTGACCATCTCCTCCCT
GCAGGCCGAGGACGTGGCCGTGTACTACTGCCAGCAGTCCAAGGAGGAC
CCCAGGACCTTCGGCCAGGGCACCAAGCTGGAGATCAAGGGAGGCGGTG -continued GATCAGGCGGAGGTGGCTCAGGTGGAGGCGGTTCTGAGGTGCAGCTGGT
GCAGTCCGGCGCCGAGGTGAAGAAGCCCGGCGCCTCCGTGAAGGTGTCC
TGCAAGGCCTCCGGCTACACCTTCACCGACTACAACATGGACTGGGTGA
GGCAGGCCCCCGGCAAGGGCCTGGAGTGGATCGGCGACATCAACCCCAA
CAACGGCGGCACCCTGTACAACCAGAAGTTCAGGGGCAGGGTGACCCTG
ACCGTGGACAAGTCCATCTCCACCGCCTACATGGAGCTGTCCAGGCTGA
GGTCCGACGACACCGCCGTGTACTACTGCGCCAGGTCCGAGGTGTTCTA
CGGCAACTACGCCGACTACTGGGGCCAGGGCACCACCGTGACCGTGTCC
TCCGAGCCCAAGTCCTGCGACAAGACCCACACCTGCCCCCCCTGCCCCG
CCCCCGAGGCCGCCGGCGGCCCCTCCGTGTTCCTGTTCCCCCCCAAGCC
CAAGGACACCCTGATGATCTCCAGGACCCCCGAGGTGACCTGCGTGGTG
GTGGACGTGTCCCACGAGGACCCCGAGGTGAAGTTCAACTGGTACGTGG
ACGGCGTGGAGGTGCACAACGCCAAGACCAAGCCCAGGGAGGAGCAGTA
CAACTCCACCTACAGGGTGGTGTCCGTGCTGACCGTGCTGCACCAGGAC
TGGCTGAACGGCAAGGAGTACAAGTGCAAGGTGTCCAACAAGGCCCTGC
CCGCCCCCATCGAGAAGACCATCTCCAAGGCCAAGGGCCAGCCCAGGGA
GCCCCAGGTGTGCACCCTGCCCCCCTCCAGGGACGAGCTGACCAAGAAC
CAGGTGTCCCTGTCCTGCGCCGTGAAGGGCTTCTACCCCTCCGACATCG
CCGTGGAGTGGGAGTCCAACGGCCAGCCCGAGAACAACTACAAGACCAC
CCCCCCCGTGCTGGACTCCGACGGCTCCTTCTTCCTGGTGTCCAAGCTG
ACCGTGGACAAGTCCAGGTGGCAGCAGGGCAACGTGTTCTCCTGCTCCG
TGATGCACGAGGCCCTGCACAACCACTACACCCAGAAGTCCCTGTCCCT
GTCCCCCGGCAAGTAA.

Nucleotide Sequence Encoding B7H6-9 Antibody (SEQ ID NO: 78)
GACATCGTGCTGACCCAGACCCCCCTGTCCCTGTCCGTGACCCCCGGCC
AGCCCGCCTCCATCTCCTGCAAGGCCTCCCAGTCCGTGGACTACGACGG
CGACTCCTACATGAACTGGTACCTGCAGAAGCCCGGCCAGCCCCCCCAG
CTGCTGATCTACGCCGCCTCCACCCTGCACTCCGGCGTGCCCGACAGGT
TCTCCGGCTCCGGCTCCGGCACCGACTTCACCCTGAAGATCTCCAGGGT
GGAGGCCGAGGACGTGGGCGTGTACTACTGCCAGCAGTCCAAGGAGGAC
CCCAGGACCTTCGGCCAGGGCACCAAGCTGGAGATCAAGGGAGGCGGTG
GATCAGGCGGAGGTGGCTCAGGTGGAGGCGGTTCTGAGGTGCAGCTGGT
GCAGTCCGGCGCCGAGGTGAAGAAGCCCGGCGCCTCCGTGAAGGTGTCC
TGCAAGGCCTCCGGCTACACCTTCACCGACTACAACATGGACTGGGTGA
GGCAGGCCCCCGGCCAGGGCCTGGAGTGGATGGGCGACATCAACCCCAA
CAACGGCGGCACCCTGTACAACCAGAAGTTCAGGGGCAGGGTGACCATG
ACCGTGGACACCTCCATCTCCACCGCCTACATGGAGCTGTCCAGGCTGA
GGTCCGACGACACCGCCGTGTACTACTGCGCCAGGTCCGAGGTGTTCTA
CGGCAACTACGCCGACTACTGGGGCCAGGGCACCACCGTGACCGTGTCC -continued TCCGAGCCCAAGTCCTGCGACAAGACCCACACCTGCCCCCCCTGCCCCG
CCCCCGAGGCCGCCGGCGGCCCCTCCGTGTTCCTGTTCCCCCCCAAGCC
CAAGGACACCCTGATGATCTCCAGGACCCCCGAGGTGACCTGCGTGGTG
GTGGACGTGTCCCACGAGGACCCCGAGGTGAAGTTCAACTGGTACGTGG
ACGGCGTGGAGGTGCACAACGCCAAGACCAAGCCCAGGGAGGAGCAGTA
CAACTCCACCTACAGGGTGGTGTCCGTGCTGACCGTGCTGCACCAGGAC
TGGCTGAACGGCAAGGAGTACAAGTGCAAGGTGTCCAACAAGGCCCTGC
CCGCCCCCATCGAGAAGACCATCTCCAAGGCCAAGGGCCAGCCCAGGGA
GCCCCAGGTGTGCACCCTGCCCCCCTCCAGGGACGAGCTGACCAAGAAC
CAGGTGTCCCTGTCCTGCGCCGTGAAGGGCTTCTACCCCTCCGACATCG
CCGTGGAGTGGGAGTCCAACGGCCAGCCCGAGAACAACTACAAGACCAC
CCCCCCCGTGCTGGACTCCGACGGCTCCTTCTTCCTGGTGTCCAAGCTG
ACCGTGGACAAGTCCAGGTGGCAGCAGGGCAACGTGTTCTCCTGCTCCG
TGATGCACGAGGCCCTGCACAACCACTACACCCAGAAGTCCCTGTCCCT
GTCCCCCGGCAAGTAA.

Nucleotide Sequence Encoding B7H6-10 Antibody (SEQ ID NO: 79)
GACATCGTGCTGACCCAGACCCCCCTGTCCCTGTCCGTGACCCCCGGCC
AGCCCGCCTCCATCTCCTGCAAGGCCTCCCAGTCCGTGGACTACGACGG
CGACTCCTACATGAACTGGTACCTGCAGAAGCCCGGCCAGCCCCCCCAG
CTGCTGATCTACGCCGCCTCCACCCTGCACTCCGGCGTGCCCGACAGGT
TCTCCGGCTCCGGCTCCGGCACCGACTTCACCCTGAAGATCTCCAGGGT
GGAGGCCGAGGACGTGGGCGTGTACTACTGCCAGCAGTCCAAGGAGGAC
CCCAGGACCTTCGGCCAGGGCACCAAGCTGGAGATCAAGGGAGGCGGTG
GATCAGGCGGAGGTGGCTCAGGTGGAGGCGGTTCTGAGGTGCAGCTGGT
GCAGTCCGGCGCCGAGGTGAAGAAGCCCGGCGCCTCCGTGAAGGTGTCC
TGCAAGGCCTCCGGCTACACCTTCACCGACTACAACATGGACTGGGTGA
GGCAGGCCCCCGGCCAGGGCCTGGAGTGGATCGGCGACATCAACCCCAA
CAACGGCGGCACCCTGTACAACCAGAAGTTCAGGGGCAGGGTGACCCTG
ACCGTGGACACCTCCATCTCCACCGCCTACATGGAGCTGTCCAGGCTGA
GGTCCGACGACACCGCCGTGTACTACTGCGCCAGGTCCGAGGTGTTCTA
CGGCAACTACGCCGACTACTGGGGCCAGGGCACCACCGTGACCGTGTCC
TCCGAGCCCAAGTCCTGCGACAAGACCCACACCTGCCCCCCCTGCCCCG
CCCCCGAGGCCGCCGGCGGCCCCTCCGTGTTCCTGTTCCCCCCCAAGCC
CAAGGACACCCTGATGATCTCCAGGACCCCCGAGGTGACCTGCGTGGTG
GTGGACGTGTCCCACGAGGACCCCGAGGTGAAGTTCAACTGGTACGTGG
ACGGCGTGGAGGTGCACAACGCCAAGACCAAGCCCAGGGAGGAGCAGTA
CAACTCCACCTACAGGGTGGTGTCCGTGCTGACCGTGCTGCACCAGGAC
TGGCTGAACGGCAAGGAGTACAAGTGCAAGGTGTCCAACAAGGCCCTGC
CCGCCCCCATCGAGAAGACCATCTCCAAGGCCAAGGGCCAGCCCAGGGA
GCCCCAGGTGTGCACCCTGCCCCCCTCCAGGGACGAGCTGACCAAGAAC
CAGGTGTCCCTGTCCTGCGCCGTGAAGGGCTTCTACCCCTCCGACATCG
CCGTGGAGTGGGAGTCCAACGGCCAGCCCGAGAACAACTACAAGACCAC
CCCCCCCGTGCTGGACTCCGACGGCTCCTTCTTCCTGGTGTCCAAGCTG
ACCGTGGACAAGTCCAGGTGGCAGCAGGGCAACGTGTTCTCCTGCTCCG
TGATGCACGAGGCCCTGCACAACCACTACACCCAGAAGTCCCTGTCCCT
GTCCCCCGGCAAGTAA.

Nucleotide Sequence Encoding B7H6-11 Antibody (SEQ ID NO: 80)
GACATCGTGCTGACCCAGACCCCCCTGTCCCTGTCCGTGACCCCCGGCC
AGCCCGCCTCCATCTCCTGCAAGGCCTCCCAGTCCGTGGACTACGACGG
CGACTCCTACATGAACTGGTACCTGCAGAAGCCCGGCCAGCCCCCCCAG
CTGCTGATCTACGCCGCCTCCACCCTGCACTCCGGCGTGCCCGACAGGT
TCTCCGGCTCCGGCTCCGGCACCGACTTCACCCTGAAGATCTCCAGGGT
GGAGGCCGAGGACGTGGGCGTGTACTACTGCCAGCAGTCCAAGGAGGAC
CCCAGGACCTTCGGCCAGGGCACCAAGCTGGAGATCAAGGGAGGCGGTG
GATCAGGCGGAGGTGGCTCAGGTGGAGGCGGTTCTGAGGTGCAGCTGGT
GCAGTCCGGCGCCGAGGTGAAGAAGCCCGGCGCCTCCGTGAAGGTGTCC
TGCAAGGCCTCCGGCTACACCTTCACCGACTACAACATGGACTGGGTGA
GGCAGGCCCCCGGCCAGGGCCTGGAGTGGATCGGCGACATCAACCCCAA
CAACGGCGGCACCCTGTACAACCAGAAGTTCAGGGGCAGGGTGACCCTG
ACCGTGGACAAGTCCATCTCCACCGCCTACATGGAGCTGTCCAGGCTGA
GGTCCGACGACACCGCCGTGTACTACTGCGCCAGGTCCGAGGTGTTCTA
CGGCAACTACGCCGACTACTGGGGCCAGGGCACCACCGTGACCGTGTCC
TCCGAGCCCAAGTCCTGCGACAAGACCCACACCTGCCCCCCCTGCCCCG
CCCCCGAGGCCGCCGGCGGCCCCTCCGTGTTCCTGTTCCCCCCCAAGCC
CAAGGACACCCTGATGATCTCCAGGACCCCCGAGGTGACCTGCGTGGTG
GTGGACGTGTCCCACGAGGACCCCGAGGTGAAGTTCAACTGGTACGTGG
ACGGCGTGGAGGTGCACAACGCCAAGACCAAGCCCAGGGAGGAGCAGTA
CAACTCCACCTACAGGGTGGTGTCCGTGCTGACCGTGCTGCACCAGGAC
TGGCTGAACGGCAAGGAGTACAAGTGCAAGGTGTCCAACAAGGCCCTGC
CCGCCCCCATCGAGAAGACCATCTCCAAGGCCAAGGGCCAGCCCAGGGA
GCCCCAGGTGTGCACCCTGCCCCCCTCCAGGGACGAGCTGACCAAGAAC
CAGGTGTCCCTGTCCTGCGCCGTGAAGGGCTTCTACCCCTCCGACATCG
CCGTGGAGTGGGAGTCCAACGGCCAGCCCGAGAACAACTACAAGACCAC
CCCCCCCGTGCTGGACTCCGACGGCTCCTTCTTCCTGGTGTCCAAGCTG
ACCGTGGACAAGTCCAGGTGGCAGCAGGGCAACGTGTTCTCCTGCTCCG
TGATGCACGAGGCCCTGCACAACCACTACACCCAGAAGTCCCTGTCCCT
GTCCCCCGGCAAGTAA.

Nucleotide Sequence Encoding B7H6-12 Antibody (SEQ ID NO: 81)

GACATCGTGCTGACCCAGACCCCCCTGTCCCTGTCCGTGACCCCCGGCC
AGCCCGCCTCCATCTCCTGCAAGGCCTCCCAGTCCGTGGACTACGACGG
CGACTCCTACATGAACTGGTACCTGCAGAAGCCCGGCCAGCCCCCCCAG
CTGCTGATCTACGCCGCCTCCACCCTGCACTCCGGCGTGCCCGACAGGT
TCTCCGGCTCCGGCTCCGGCACCGACTTCACCCTGAAGATCTCCAGGGT
GGAGGCCGAGGACGTGGGCGTGTACTACTGCCAGCAGTCCAAGGAGGAC
CCCAGGACCTTCGGCCAGGGCACCAAGCTGGAGATCAAGGGAGGCGGTG
GATCAGGCGGAGGTGGCTCAGGTGGAGGCGGTTCTGAGGTGCAGCTGGT
GCAGTCCGGCGCCGAGGTGAAGAAGCCCGGCGCCTCCGTGAAGGTGTCC
TGCAAGGCCTCCGGCTACACCTTCACCGACTACAACATGGACTGGGTGA
GGCAGGCCCCCGGCAAGGGCCTGGAGTGGATCGGCGACATCAACCCCAA
CAACGGCGGCACCCTGTACAACCAGAAGTTCAGGGGCAGGGTGACCCTG
ACCGTGGACAAGTCCATCTCCACCGCCTACATGGAGCTGTCCAGGCTGA
GGTCCGACGACACCGCCGTGTACTACTGCGCCAGGTCCGAGGTGTTCTA
CGGCAACTACGCCGACTACTGGGGCCAGGGCACCACCGTGACCGTGTCC
TCCGAGCCCAAGTCCTGCGACAAGACCCACACCTGCCCCCCCTGCCCCG
CCCCCGAGGCCGCCGGCGGCCCCTCCGTGTTCCTGTTCCCCCCCAAGCC
CAAGGACACCCTGATGATCTCCAGGACCCCCGAGGTGACCTGCGTGGTG
GTGGACGTGTCCCACGAGGACCCCGAGGTGAAGTTCAACTGGTACGTGG
ACGGCGTGGAGGTGCACAACGCCAAGACCAAGCCCAGGGAGGAGCAGTA
CAACTCCACCTACAGGGTGGTGTCCGTGCTGACCGTGCTGCACCAGGAC
TGGCTGAACGGCAAGGAGTACAAGTGCAAGGTGTCCAACAAGGCCCTGC
CCGCCCCCATCGAGAAGACCATCTCCAAGGCCAAGGGCCAGCCCAGGGA
GCCCCAGGTGTGCACCCTGCCCCCCTCCAGGGACGAGCTGACCAAGAAC
CAGGTGTCCCTGTCCTGCGCCGTGAAGGGCTTCTACCCCTCCGACATCG
CCGTGGAGTGGGAGTCCAACGGCCAGCCCGAGAACAACTACAAGACCAC
CCCCCCCGTGCTGGACTCCGACGGCTCCTTCTTCCTGGTGTCCAAGCTG
ACCGTGGACAAGTCCAGGTGGCAGCAGGGCAACGTGTTCTCCTGCTCCG
TGATGCACGAGGCCCTGCACAACCACTACACCCAGAAGTCCCTGTCCCT
GTCCCCCGGCAAGTAA.

Nucleotide Sequence Encoding B7H6-13 Antibody (SEQ ID NO: 82)

GACATCGTGCTGACCCAGACCCCCCTGTCCCTGTCCGTGACCCCCGGCC
AGCCCGCCTCCATCTCCTGCAAGGCCTCCCAGTCCGTGGACTACGACGG
CGACTCCTACATGAACTGGTACCTGCAGAAGCCCGGCCAGCCCCCCCAG
CTGCTGATCTACGCCGCCTCCACCCTGCACTCCGGCATCCCCGACAGGT
TCTCCGGCTCCGGCTCCGGCACCGACTTCACCCTGAAGATCTCCAGGGT
GGAGGCCGAGGACGTGGGCGTGTACTACTGCCAGCAGTCCAAGGAGGAC
CCCAGGACCTTCGGCCAGGGCACCAAGCTGGAGATCAAGGGAGGCGGTG

-continued

GATCAGGCGGAGGTGGCTCAGGTGGAGGCGGTTCTGAGGTGCAGCTGGT
GCAGTCCGGCGCCGAGGTGAAGAAGCCCGGCGCCTCCGTGAAGGTGTCC
TGCAAGGCCTCCGGCTACACCTTCACCGACTACAACATGGACTGGGTGA
GGCAGGCCCCCGGCCAGGGCCTGGAGTGGATGGGCGACATCAACCCCAA
CAACGGCGGCACCCTGTACAACCAGAAGTTCAGGGGCAGGGTGACCATG
ACCGTGGACACCTCCATCTCCACCGCCTACATGGAGCTGTCCAGGCTGA
GGTCCGACGACACCGCCGTGTACTACTGCGCCAGGTCCGAGGTGTTCTA
CGGCAACTACGCCGACTACTGGGGCCAGGGCACCACCGTGACCGTGTCC
TCCGAGCCCAAGTCCTGCGACAAGACCCACACCTGCCCCCCCTGCCCCG
CCCCCGAGGCCGCCGGCGGCCCCTCCGTGTTCCTGTTCCCCCCCAAGCC
CAAGGACACCCTGATGATCTCCAGGACCCCCGAGGTGACCTGCGTGGTG
GTGGACGTGTCCCACGAGGACCCCGAGGTGAAGTTCAACTGGTACGTGG
ACGGCGTGGAGGTGCACAACGCCAAGACCAAGCCCAGGGAGGAGCAGTA
CAACTCCACCTACAGGGTGGTGTCCGTGCTGACCGTGCTGCACCAGGAC
TGGCTGAACGGCAAGGAGTACAAGTGCAAGGTGTCCAACAAGGCCCTGC
CCGCCCCCATCGAGAAGACCATCTCCAAGGCCAAGGGCCAGCCCAGGGA
GCCCCAGGTGTGCACCCTGCCCCCCTCCAGGGACGAGCTGACCAAGAAC
CAGGTGTCCCTGTCCTGCGCCGTGAAGGGCTTCTACCCCTCCGACATCG
CCGTGGAGTGGGAGTCCAACGGCCAGCCCGAGAACAACTACAAGACCAC
CCCCCCCGTGCTGGACTCCGACGGCTCCTTCTTCCTGGTGTCCAAGCTG
ACCGTGGACAAGTCCAGGTGGCAGCAGGGCAACGTGTTCTCCTGCTCCG
TGATGCACGAGGCCCTGCACAACCACTACACCCAGAAGTCCCTGTCCCT
GTCCCCCGGCAAGTAA.

Nucleotide Sequence Encoding B7H6-14 Antibody (SEQ ID NO: 83)

GACATCGTGCTGACCCAGACCCCCCTGTCCCTGTCCGTGACCCCCGGCC
AGCCCGCCTCCATCTCCTGCAAGGCCTCCCAGTCCGTGGACTACGACGG
CGACTCCTACATGAACTGGTACCTGCAGAAGCCCGGCCAGCCCCCCCAG
CTGCTGATCTACGCCGCCTCCACCCTGCACTGCGGCATCCCCGACAGGT
TCTCCGGCTCCGGCTCCGGCACCGACTTCACCCTGAAGATCTCCAGGGT
GGAGGCCGAGGACGTGGGCGTGTACTACTGCCAGCAGTCCAAGGAGGAC
CCCAGGACCTTCGGCCAGGGCACCAAGCTGGAGATCAAGGGAGGCGGTG
GATCAGGCGGAGGTGGCTCAGGTGGAGGCGGTTCTGAGGTGCAGCTGGT
GCAGTCCGGCGCCGAGGTGAAGAAGCCCGGCGCCTCCGTGAAGGTGTCC
TGCAAGGCCTCCGGCTACACCTTCACCGACTACAACATGGACTGGGTGA
GGCAGGCCCCCGGCCAGGGCCTGGAGTGGATCGGCGACATCAACCCCAA
CAACGGCGGCACCCTGTACAACCAGAAGTTCAGGGGCAGGGTGACCCTG
ACCGTGGACACCTCCATCTCCACCGCCTACATGGAGCTGTCCAGGCTGA
GGTCCGACGACACCGCCGTGTACTACTGCGCCAGGTCCGAGGTGTTCTA
CGGCAACTACGCCGACTACTGGGGCCAGGGCACCACCGTGACCGTGTCC

-continued

TCCGAGCCCAAGTCCTGCGACAAGACCCACACCTGCCCCCCCTGCCCCG
CCCCCGAGGCCGCCGGCGGCCCCTCCGTGTTCCTGTTCCCCCCCAAGCC
CAAGGACACCCTGATGATCTCCAGGACCCCCGAGGTGACCTGCGTGGTG
GTGGACGTGTCCCACGAGGACCCCGAGGTGAAGTTCAACTGGTACGTGG
ACGGCGTGGAGGTGCACAACGCCAAGACCAAGCCCAGGGAGGAGCAGTA
CAACTCCACCTACAGGGTGGTGTCCGTGCTGACCGTGCTGCACCAGGAC
TGGCTGAACGGCAAGGAGTACAAGTGCAAGGTGTCCAACAAGGCCCTGC
CCGCCCCCATCGAGAAGACCATCTCCAAGGCCAAGGGCCAGCCCAGGGA
GCCCCAGGTGTGCACCCTGCCCCCCTCCAGGGACGAGCTGACCAAGAAC
CAGGTGTCCCTGTCCTGCGCCGTGAAGGGCTTCTACCCCTCCGACATCG
CCGTGGAGTGGGAGTCCAACGGCCAGCCCGAGAACAACTACAAGACCAC
CCCCCCCGTGCTGGACTCCGACGGCTCCTTCTTCCTGGTGTCCAAGCTG
ACCGTGGACAAGTCCAGGTGGCAGCAGGGCAACGTGTTCTCCTGCTCCG
TGATGCACGAGGCCCTGCACAACCACTACACCCAGAAGTCCCTGTCCCT
GTCCCCCGGCAAGTAA.

Nucleotide Sequence Encoding B7H6-15

(SEQ ID NO: 84)
GACATCGTGCTGACCCAGACCCCCCTGTCCCTGTCCGTGACCCCCGGCCA
GCCCGCCTCCATCTCCTGCAAGGCCTCCCAGTCCGTGGACTACGACGGCG
ACTCCTACATGAACTGGTACCTGCAGAAGCCCGGCCAGCCCCCCCAGCTG
CTGATCTACGCCGCCTCCACCCTGCACTCCGGCATCCCCGACAGGTTCTC
CGGCTCCGGCTCCGGCACCGACTTCACCCTGAAGATCTCCAGGGTGGAGG
CCGAGGACGTGGGCGTGTACTACTGCCAGCAGTCCAAGGAGGACCCCAGG
ACCTTCGGCCAGGGCACCAAGCTGGAGATCAAGGGAGGCGGTGGATCAGG
CGGAGGTGGCTCAGGTGGAGGCGGTTCTGAGGTGCAGCTGGTGCAGTCCG
GCGCCGAGGTGAAGAAGCCCGGCGCCTCCGTGAAGGTGTCCTGCAAGGCC
TCCGGCTACACCTTCACCGACTACAACATGGACTGGGTGAGGCAGGCCCC
CGGCCAGGGCCTGGAGTGGATCGGCGACATCAACCCCAACAACGGCGGCA
CCCTGTACAACCAGAAGTTCAGGGGCAGGGTGACCCTGACCGTGGACAAG
TCCATCTCCACCGCCTACATGGAGCTGTCCAGGCTGAGGTCCGACGACAC
CGCCGTGTACTACTGCGCCAGGTCCGAGGTGTTCTACGGCAACTACGCCG
ACTACTGGGGCCAGGGCACCACCGTGACCGTGTCCTCCGAGCCCAAGTCC
TGCGACAAGACCCACACCTGCCCCCCCTGCCCCGCCCCCGAGGCCGCCGG
CGGCCCCTCCGTGTTCCTGTTCCCCCCCAAGCCCAAGGACACCCTGATGA
TCTCCAGGACCCCCGAGGTGACCTGCGTGGTGGTGGACGTGTCCCACGAG
GACCCCGAGGTGAAGTTCAACTGGTACGTGGACGGCGTGGAGGTGCACAA
CGCCAAGACCAAGCCCAGGGAGGAGCAGTACAACTCCACCTACAGGGTGG
TGTCCGTGCTGACCGTGCTGCACCAGGACTGGCTGAACGGCAAGGAGTAC
AAGTGCAAGGTGTCCAACAAGGCCCTGCCCGCCCCCATCGAGAAGACCAT
CTCCAAGGCCAAGGGCCAGCCCAGGGAGCCCCAGGTGTGCACCCTGCCCC

-continued

CCTCCAGGGACGAGCTGACCAAGAACCAGGTGTCCCTGTCCTGCGCCGTG
AAGGGCTTCTACCCCTCCGACATCGCCGTGGAGTGGGAGTCCAACGGCCA
GCCCGAGAACAACTACAAGACCACCCCCCCCGTGCTGGACTCCGACGGCT
CCTTCTTCCTGGTGTCCAAGCTGACCGTGGACAAGTCCAGGTGGCAGCAG
GGCAACGTGTTCTCCTGCTCCGTGATGCACGAGGCCCTGCACAACCACTA
CACCCAGAAGTCCCTGTCCCTGTCCCCCGGCAAGTAA.

Nucleotide Sequence Encoding B7H6-16 Antibody (SEQ ID NO: 85)
GACATCGTGCTGACCCAGACCCCCCTGTCCCTGTCCGTGACCCCCGGCCA
GCCCGCCTCCATCTCCTGCAAGGCCTCCCAGTCCGTGGACTACGACGGCG
ACTCCTACATGAACTGGTACCTGCAGAAGCCCGGCCAGCCCCCCCAGCTG
CTGATCTACGCCGCCTCCACCCTGCACTCCGGCATCCCCGACAGGTTCTC
CGGCTCCGGCTCCGGCACCGACTTCACCCTGAAGATCTCCAGGGTGGAGG
CCGAGGACGTGGGCGTGTACTACTGCCAGCAGTCCAAGGAGGACCCCAGG
ACCTTCGGCCAGGGCACCAAGCTGGAGATCAAGGGAGGCGGTGGATCAGG
CGGAGGTGGCTCAGGTGGAGGCGGTTCTGAGGTGCAGCTGGTGCAGTCCG
GCGCCGAGGTGAAGAAGCCCGGCGCCTCCGTGAAGGTGTCCTGCAAGGCC
TCCGGCTACACCTTCACCGACTACAACATGGACTGGGTGAGGCAGGCCCC
CGGCAAGGGCCTGGAGTGGATCGGCGACATCAACCCCAACAACGGCGGCA
CCCTGTACAACCAGAAGTTCAGGGGCAGGGTGACCCTGACCGTGGACAAG
TCCATCTCCACCGCCTACATGGAGCTGTCCAGGCTGAGGTCCGACGACAC
CGCCGTGTACTACTGCGCCAGGTCCGAGGTGTTCTACGGCAACTACGCCG
ACTACTGGGGCCAGGGCACCACCGTGACCGTGTCCTCCGAGCCCAAGTCC
TGCGACAAGACCCACACCTGCCCCCCCTGCCCCGCCCCCGAGGCCGCCGG
CGGCCCCTCCGTGTTCCTGTTCCCCCCCAAGCCCAAGGACACCCTGATGA
TCTCCAGGACCCCCGAGGTGACCTGCGTGGTGGTGGACGTGTCCCACGAG
GACCCCGAGGTGAAGTTCAACTGGTACGTGGACGGCGTGGAGGTGCACAA
CGCCAAGACCAAGCCCAGGGAGGAGCAGTACAACTCCACCTACAGGGTGG
TGTCCGTGCTGACCGTGCTGCACCAGGACTGGCTGAACGGCAAGGAGTAC
AAGTGCAAGGTGTCCAACAAGGCCCTGCCCGCCCCCATCGAGAAGACCAT
CTCCAAGGCCAAGGGCCAGCCCAGGGAGCCCCAGGTGTGCACCCTGCCCC
CCTCCAGGGACGAGCTGACCAAGAACCAGGTGTCCCTGTCCTGCGCCGTG
AAGGGCTTCTACCCCTCCGACATCGCCGTGGAGTGGGAGTCCAACGGCCA
GCCCGAGAACAACTACAAGACCACCCCCCCCGTGCTGGACTCCGACGGCT
CCTTCTTCCTGGTGTCCAAGCTGACCGTGGACAAGTCCAGGTGGCAGCAG
GGCAACGTGTTCTCCTGCTCCGTGATGCACGAGGCCCTGCACAACCACTA
CACCCAGAAGTCCCTGTCCCTGTCCCCCGGCAAGTAA.

Nucleotide Sequence Encoding B7H6-17 Antibody (SEQ ID NO: 86)
GACATCGTGCTGACCCAGTCCCCCGTGTCCCTGGCCGTGCCCCTGGGCCA
GAGGGCCACCATCTCCTGCAAGGCCTCCCAGTCCGTGGACTACGACGGCG
ACTCCTACATGAACTGGTACCAGCAGAAGCCCGGCCAGCCCCCCAAGCTG
CTGATCTACGCCGCCTCCACCCTGCACTCCGGCATCCCCGTGAGGTTCTC
CGGCTCCGGCTCCGGCACCGACTTCACCCTGAACATCCACCCCGTGGAGG
AGGAGGACGCCGCCTCCTACTACTGCCAGCAGTCCAAGGAGGACCCCAGG
ACCTTCGGCGGCGGCACCAAGCTGGAGATCAAGGGAGGCGGTGGATCAGG
CGGAGGTGGCTCAGGTGGAGGCGGTTCTGAGGTGCTGCTGCAGCAGTCCG
GCCCCGAGGTGGTGAAGCCCGGCGCCTCCGTGAAGATCACCTGCAAGGCC
TCCGGCTACACCTTCACCGACTACAACATGGACTGGGTGAAGCAGTCCCA
CGGCAAGTCCCTGGAGTGGATCGGCGACATCAACCCCAACAACGCCGGCA
CCCTGTACAACCAGAAGTTCAGGGGCAGGGTGACCCTGATCGTGGACAAG
TCCTCCTCCACCGCCTACATGGAGCTGAGGTCCCTGACCTCCGACGACAC
CGCCGTGTACTACTGCGCCAGGTCCGAGGTGTTCTACGGCAACTACGCCG
ACTACTGGGGCCAGGGCACCACCCTGACCGTGTCCTCCGAGCCCAAGTCC
TGCGACAAGACCCACACCTGCCCCCCCTGCCCCGCCCCCGAGGCCGCCGG
CGGCCCCTCCGTGTTCCTGTTCCCCCCCAAGCCCAAGGACACCCTGATGA
TCTCCAGGACCCCCGAGGTGACCTGCGTGGTGGTGGACGTGTCCCACGAG
GACCCCGAGGTGAAGTTCAACTGGTACGTGGACGGCGTGGAGGTGCACAA
CGCCAAGACCAAGCCCAGGGAGGAGCAGTACAACTCCACCTACAGGGTGG
TGTCCGTGCTGACCGTGCTGCACCAGGACTGGCTGAACGGCAAGGAGTAC
AAGTGCAAGGTGTCCAACAAGGCCCTGCCCGCCCCCATCGAGAAGACCAT
CTCCAAGGCCAAGGGCCAGCCCAGGGAGCCCCAGGTGTGCACCCTGCCCC
CCTCCAGGGACGAGCTGACCAAGAACCAGGTGTCCCTGTCCTGCGCCGTG
AAGGGCTTCTACCCCTCCGACATCGCCGTGGAGTGGGAGTCCAACGGCCA
GCCCGAGAACAACTACAAGACCACCCCCCCCGTGCTGGACTCCGACGGCT
CCTTCTTCCTGGTGTCCAAGCTGACCGTGGACAAGTCCAGGTGGCAGCAG
GGCAACGTGTTCTCCTGCTCCGTGATGCACGAGGCCCTGCACAACCACTA
CACCCAGAAGTCCCTGTCCCTGTCCCCCGGCAAGTAA.

Nucleotide Sequence Encoding B7H6-18 Antibody (SEQ ID NO: 87)
GACATCGTGCTGACCCAGTCCCCCGTGTCCCTGGCCGTGCCCCTGGGCCA
GAGGGCCACCATCTCCTGCAAGGCCTCCCAGTCCGTGGACTACGACGCCG
ACTCCTACATGAACTGGTACCAGCAGAAGCCCGGCCAGCCCCCCAAGCTG
CTGATCTACGCCGCCTCCACCCTGCACTCCGGCATCCCCGTGAGGTTCTC
CGGCTCCGGCTCCGGCACCGACTTCACCCTGAACATCCACCCCGTGGAGG
AGGAGGACGCCGCCTCCTACTACTGCCAGCAGTCCAAGGAGGACCCCAGG
ACCTTCGGCGGCGGCACCAAGCTGGAGATCAAGGGAGGCGGTGGATCAGG
CGGAGGTGGCTCAGGTGGAGGCGGTTCTGAGGTGCTGCTGCAGCAGTCCG -continued GCCCCGAGGTGGTGAAGCCCGGCGCCTCCGTGAAGATCACCTGCAAGGCC
TCCGGCTACACCTTCACCGACTACAACATGGACTGGGTGAAGCAGTCCCA
CGGCAAGTCCCTGGAGTGGATCGGCGACATCAACCCCAACAACGGCGGCA
CCCTGTACAACCAGAAGTTCAGGGGCAGGGTGACCCTGATCGTGGACAAG
TCCTCCTCCACCGCCTACATGGAGCTGAGGTCCCTGACCTCCGACGACAC
CGCCGTGTACTACTGCGCCAGGTCCGAGGTGTTCTACGGCAACTACGCCG
ACTACTGGGGCCAGGGCACCACCCTGACCGTGTCCTCCGAGCCCAAGTCC
TGCGACAAGACCCACACCTGCCCCCCCTGCCCCGCCCCCGAGGCCGCCGG
CGGCCCCTCCGTGTTCCTGTTCCCCCCCAAGCCCAAGGACACCCTGATGA
TCTCCAGGACCCCCGAGGTGACCTGCGTGGTGGTGGACGTGTCCCACGAG
GACCCCGAGGTGAAGTTCAACTGGTACGTGGACGGCGTGGAGGTGCACAA
CGCCAAGACCAAGCCCAGGGAGGAGCAGTACAACTCCACCTACAGGGTGG
TGTCCGTGCTGACCGTGCTGCACCAGGACTGGCTGAACGGCAAGGAGTAC
AAGTGCAAGGTGTCCAACAAGGCCCTGCCCGCCCCCATCGAGAAGACCAT
CTCCAAGGCCAAGGGCCAGCCCAGGGAGCCCCAGGTGTGCACCCTGCCCC
CCTCCAGGGACGAGCTGACCAAGAACCAGGTGTCCCTGTCCTGCGCCGTG
AAGGGCTTCTACCCCTCCGACATCGCCGTGGAGTGGGAGTCCAACGGCCA
GCCCGAGAACAACTACAAGACCACCCCCCCCGTGCTGGACTCCGACGGCT
CCTTCTTCCTGGTGTCCAAGCTGACCGTGGACAAGTCCAGGTGGCAGCAG
GGCAACGTGTTCTCCTGCTCCGTGATGCACGAGGCCCTGCACAACCACTA
CACCCAGAAGTCCCTGTCCCTGTCCCCCGGCAAGTAA.

It should be noted that with respect to the nucleic acid referred to in the present specification and claims, those skilled in the art can understand that the nucleic acid includes any one of two complementary strands, or both. For convenience, in this specification and claims, in most cases only one strand is shown, but another strand complementary thereto is disclosed in fact. In addition, the nucleic acid sequences in the present disclosure include the form of DNA or RNA. When one of them is disclosed, the other is also disclosed.

In a fourth aspect of the present disclosure, the present disclosure provides an expression vector carrying the nucleic acid molecule as described above. The expression vector may include an optional control sequence operably linked to the nucleic acid molecule. The control sequence is one or more control sequences that direct expression of the nucleic acid molecule in a host. The expression vector proposed in some specific embodiments of the present disclosure can efficiently express the recombinant antibody in suitable host cells, and thus can be effectively used for specific treatment or prevention of tumors, particularly tumors expressing B7H6.

In a fifth aspect of the present disclosure, the present disclosure provides a recombinant cell carrying the nucleic acid molecule according to the third aspect, the expression vector according to the fourth aspect, or the recombinant antibody according to the first or second aspect. The recombinant cell is obtained by transfecting or transforming the expression vector. According to some specific embodiments of the present disclosure, the recombinant cells can efficiently express the recombinant antibody under suitable conditions, and the recombinant cells can be effectively used for specific treatment or prevention Of a tumor, particularly a tumor expressing B7H6.

It should be noted that "suitable conditions" in the specification refers to conditions suitable for the expression of the recombinant antibodies described in the present disclosure. Those skilled in the art will readily appreciate that suitable conditions for the expression of the recombinant antibodies include, but are not limited to, suitable transformation or transfection manners, suitable transformation or transfection conditions, healthy host cell status, suitable host cell density, suitable cell culture environment, and suitable cell culture time. The "suitable conditions" are not particularly limited. Those skilled in the art can optimize the conditions for the expression of the recombinant antibody according to the specific circumstances of the laboratory.

In a sixth aspect of the present disclosure, the present disclosure provides a composition including the recombinant antibody according to the first or second aspect, the nucleic acid molecule according to the third aspect, the expression vector according to the fourth aspect or the recombinant cell according to the fifth aspect. As described above, the recombinant antibody according to the embodiments of the present disclosure can effectively bind to CD3 or B7H6 protein molecules, thereby specifically recognizing tumor cells highly expressing the B7H6. They can promote selective localization of T cells to the tumor site rather than in the peripheral circulation, avoiding systemic activation. The composition, such as a food composition or a pharmaceutical composition, including the recombinant antibody and a series of corresponding substances, also has significant effects for treating or preventing tumors expressing B7H6, with higher safety and fewer side effects.

In an eighth aspect of the present disclosure, the present disclosure provides a medicament including the recombinant antibody according to the first or second aspect, the nucleic acid molecule according to the third aspect, the expression vector according to the fourth aspect, the recombinant cell according to the fifth aspect, or the composition according to the sixth aspect. The medicament is used for treating or preventing cancer. As described above, the recombinant antibody according to the embodiments of the present disclosure can effectively bind to CD3 or B7H6 protein molecules, thereby specifically recognizing tumor cells highly expressing the B7H6. They can also promote selective localization of T cells to the tumor site rather than in the peripheral circulation, avoiding systemic activation. The medicament including the recombinant antibody or a series of corresponding substances also has significant effects for treating or preventing tumors expressing B7H6, with higher safety and fewer side effects.

According to some specific embodiments of the present disclosure, the cancer includes at least one of rectal cancer, non-small cell lung cancer, breast cancer, and liver cancer.

The medicament according to some specific embodiments of the present disclosure includes a pharmaceutically acceptable carrier and an effective amount of the antibody active ingredient.

As used herein, the term "effective amount" or "effective dose" refers to an amount capable of producing function or activity and acceptable for humans and/or animals.

As used herein, the "pharmaceutically acceptable" ingredient is a substance suitable for use in humans and/or mammals without casing undue adverse side effects (such as toxicity, irritation, and allergic response), i.e., a substance having an appropriate benefit/risk ratio. The term "pharmaceutically acceptable carrier" refers to a carrier used in the administration of therapeutic agents, including various excipients and diluents.

The medicament according to the present disclosure contains a safe and effective amount of the active ingredient of the present disclosure and a pharmaceutically acceptable carrier. The carrier includes, but not limited to, saline, buffer, glucose, water, glycerol, ethanol, and combinations thereof. Generally, the pharmaceutical preparation should be adapted to the administration route. A formulation of the medicament according to the present disclosure is injection, oral preparation (tablet, capsule, oral liquid), transdermal agent, or sustained-release agent. For example, the formulation is prepared with the conventional methods using physiological saline or aqueous solutions containing glucose and other adjuvants. The medicament is preferably manufactured under sterile conditions.

The effective amount of active ingredient described herein may vary depending on the administration route and the severity of the disease to be treated. A preferred effective amount can be selected and determined by those skilled in the art based on a variety of factors (e.g., through clinical trials). These factors include, but are not limited to, pharmacokinetic parameters of the active ingredient such as bioavailability, metabolism, half-life, and the like; the severity of the disease to be treated of the patient, the weight of the patient, the immune status of the patient, the administration route, etc. For example, several divided doses may be administered daily, or the dose may be proportionally reduced, based on the exigencies of therapeutic situation.

The pharmaceutically acceptable carrier described herein includes, but not limited to, water, saline, liposomes, lipids, proteins, protein-antibody conjugates, peptides, cellulose, nanogels, or combinations thereof. The selection of carrier should be adapted to the administration route, which is well-known to those skilled in the art.

Uses

In a seventh aspect of the present disclosure, the present disclosure provides use of the recombinant antibody according, to the first or second aspect, the nucleic acid molecule according to the third aspect, the expression vector according to the fourth aspect, the recombinant cell according to the fifth aspect, or the composition according to the sixth aspect in the manufacture of a medicament. The medicament is used for treating or preventing a tumor. As described above, the recombinant antibody provided by some specific embodiments of the present disclosure can effectively bind to CD3 and B7H6 protein, thereby specifically recognizing tumor cells specifically highly expressing the B7H6. Thus, the medicament prepared using the recombinant antibody and a series of corresponding substances also has significant effects for treating or preventing tumors expressing B7H6, with higher safety and fewer side effects.

According to some specific embodiments of the present disclosure, the above-mentioned uses may further include at least one of the following additional technical features.

According to some specific embodiments of the present disclosure, the tumor includes at least one of rectal cancer, non-small cell lung cancer, breast cancer, and liver cancer.

Kit

In a ninth aspect of the present disclosure, the present disclosure provides a kit including the recombinant antibody according to the first or second aspect. The recombinant antibody provided by some specific embodiments of the present disclosure can bind to the B7H6. Therefore, the kit including the recombinant antibody can be used for effectively diagnosing or detecting tumors highly expressing the B7H6 protein.

According to some specific embodiments of the present disclosure, the kit is used for diagnosing or detecting at least one of rectal cancer, non-small cell lung cancer, breast cancer, and liver cancer. The antibody provided by some specific embodiments of the present disclosure can effectively bind to CD3 and B7H6 protein molecules, thereby specifically recognizing the tumor cells, which specifically and highly express the B7H6. Therefore, the recombinant antibody can be used in the preparation of a kit for diagnosing or detecting at least one of rectal cancer, non-small cell lung cancer, breast cancer, and liver cancer. The kit can be used for scientific studies such as qualitative or quantitative detection of CD3 and/or B7H6 protein molecules in a biological sample.

Disease Therapeutic Uses and Methods

In a tenth aspect of the present disclosure, the present disclosure provides use of the above-mentioned recombinant antibody, nucleic acid molecule, expression vector, recombinant cell, composition or medicament in the treatment or prevention of cancer. As described above, the recombinant antibody can specifically recognize the above-mentioned CD3 and/or B7H6 proteins. When the affinity of the CD3 antibody is in an appropriate range and the tumor target-associated antibody has a high affinity, the bispecific antibody can promote the selective localization of T cells to the tumor site rather than in the peripheral circulation, thereby avoiding the systemic activation While effectively treating and preventing cancer. Therefore, cancer can be treated or prevented by the recombinant antibody; composition including the recombinant antibody and medicament according to the embodiments of the present disclosure, as well as a series of substances capable of obtaining the recombinant antibody expressed under the appropriate conditions, for example, the above-mentioned nucleic acid molecule, expression vector, recombinant cell, and the like.

According to some specific embodiments of the present disclosure, the cancer includes at least one of rectal cancer, non-small cell lung cancer, breast cancer, and liver cancer.

In an eleventh aspect of the present disclosure, the present disclosure provides a method for treating or preventing cancer. According to some specific embodiments of the present disclosure, the method includes: administering to the subject at least one of: 1) the recombinant antibody as described above; 2) the nucleic acid molecule as described above; 3) the expression vector as described above; 4) the recombinant cell as described above; or 5) the composition as described above. As described above, the recombinant antibody can specifically recognize the above-mentioned CD3 and/or B7H6 protein. When the affinity of the CD3 antibody is in an appropriate range and the tumor target-associated antibody has a high affinity, the bispecific antibody can promote the selective localization of T cells to the tumor site rather than in the peripheral circulation, thereby avoiding the systemic activation while effectively treating, and preventing cancer. Therefore, the method according to embodiments of the present disclosure can effectively treat or prevent cancer and avoid systemic T cell activation.

According to some specific embodiments of the present disclosure, the cancer includes at least one of rectal cancer, non-small cell lung cancer, breast cancer, and liver cancer.

Hereinafter, examples will be described in detail. Where specific techniques or conditions are not specified in the examples, they are performed according to techniques or conditions described in the literature in the related art or according to the product description. The used reagents or instruments without indicating the manufacturer are conventional and commercially available products.

Example 1: Design and Construction of CD3xB7H6 Bispecific Antibody Molecule

In this example, by performing screening on various configurations, the Applicant identified a bispecific antibody in the scFv-Fc configuration, which was designated CD3xB7H6. The antibody includes two monovalent units, one of which is an anti-CD3 ScFv-Fc form, and the other one of which an anti-B7H6 ScFv-Fc form. The light chain variable region and the heavy chain variable region of the CD3 antibody were connected by one linker peptide, and the same linker peptide was also used to connect the light chain variable region and the heavy chain variable region of the B7H6 antibody. The linker peptide has an amino acid sequence as set forth in SEQ ID NO: 46. The CD3 antibody includes the light chain variable region as set forth in SEQ ID NO: 13, and the heavy chain variable region as set forth in SEQ ID NO: 14. The B7H6 antibody includes the light chain variable region as set forth in SEQ ID NO: 15 to SEQ ID NO: 20, and the heavy chain variable region as set forth in SEQ ID NO: 21 to SEQ ID NO: 26. The Applicant performed screening on different combinations of the variable regions of the B7H6 antibody and the variable regions of the CD3 antibody, and constructed a total of 18 CD3xB7H6 recombinant antibody molecules. In addition, the Applicant performed amino acid mutation on the Fc region of the monovalent unit. The amino acids of the Fc region of the anti-CD3 were changed to cysteine (S384C) at position 384 and tryptophan (T396W) at position 396, and the amino acids of the Fc region of the anti-B7H6 were changed to cysteine (Y380C) at position 380, serine (T397S) at position 397, alanine (L399A) at position 399 and valine (Y408V) at position 408, such that homodimer thereof was unlikely to be formed and heterodimer thereof can be easily formed. The heterodimer is a bispecific antibody CD3xB7H6, and the specific structure is illustrated in FIG. 1. The 18 CD3xB7H6 recombinant antibody molecules have a CD3 single-chain antibody as set forth in SEQ ID NO: 27, a B7H6 single-chain antibody as set forth in SEQ ID NO: 28 to SEQ ID NO: 45, a primary antibody Fc region as set forth in SEQ ID NO: 47, and a secondary antibody Fc region as set forth in SEQ ID NO: 48, which are subjected to the above-mentioned mutations and linked by in a knob-into-hole structure.

Nucleic acid sequences encoding the polypeptide chains of the CD3 and B7H6 (1-18) monovalent units were cloned into the expression vector pTT5 (YouBio, cat. No. VT2202) by means of common molecular biology techniques, respectively. The specific nucleotide sequence is at least one of the nucleotide sequences as set forth in SEQ ID NO: 69, and SEQ ID NO: 70 to SEQ ID NO: 87. In the meantime, in order to express the expression vector and secrete it into the culture medium, a leader peptide of a kappa chain of murine antibody was selected and inserted into the expression vector as secretion signal peptide, which was located at the N-end of the variable region of the antibody. The amino acid sequence of the signal peptide was: METDTLLLWVLLLWVPGSTG (SEQ ID NO: 68), and the nucleotide sequence encoding the signal peptide is shown in SEQ ID NO: 88.

(SEQ ID NO: 88)
ATGGAGACCGACACCCTGCTGCTGTGGGTGCTGCTGCTGTGGGTGCCCGG

CTCCACCGGC.

CD3 Single-Chain Antibody (SEQ ID NO: 27)
MDIQMTQSPSSLSASVGDRVTITCRASQDIRNYLNWYQQKPGKAPKLLIY

YTSRLESGVPSRFSGSGSGTDYTLTISSLQPEDFATYYCQQGNTLPWTFG

QGTKVEIKGGGGSGGGGSGGGGSEVQLVESGGGLVQPGGSLRLSCAASGY

SFTGYTMNWVRQAPGKGLEWVALINPYKGVSTYNQKFKDRFTISVDKSKN

TAYLQMNSLRAEDTAVYYCARSGYYGDSDWYFDVWGQGTLVTVSS.

B7H6-1 Single-Chain Antibody (SEQ ID NO: 28)
DIVLTQSPDSLAVSLGERATINCKASQSVDYDGDSYMNWYQQKPGQPPKL

LIYAASTLHSGVPDRFSGSGSGTDFTLTISSLQAEDVAVYYCQQSKEDPR

TFGQGTKLEIKGGGGSGGGGSGGGGSEVQLVQSGAEVKKPGASVKVSCKA

SGYTFTDYNMDWVRQAPGQGLEWMGDINPNNGGTLYNQKFRGRVTMTVDT

SISTAYMELSRLRSDDTAVYYCARSEVFYGNYADYWGQGTTVTVSS.

B7H6-2 Single-Chain Antibody (SEQ ID NO: 29)
DIVLTQSPDSLAVSLGERATINCKASQSVDYDGDSYMNWYQQKPGQPPKL

LIYAASTLHSGVPDRFSGSGSGTDFTLTISSLQAEDVAVYYCQQSKEDPR

TFGQGTKLEIKGGGGSGGGGSGGGGSEVQLVQSGAEVKKPGASVKVSCKA

SGYTFTDYNMDWVRQAPGQGLEWIGDINPNNGGTLYNQKFRGRVTLTVDT

SISTAYMELSRLRSDDTAVYYCARSEVFYGNYADYWGQGTTVTVSS.

B7H6-3 Single-Chain Antibody (SEQ ID NO: 30)
DIVLTQSPDSLAVSLGERATINCKASQSVDYDGDSYMNWYQQKPGQPPKL

LIYAASTLHSGVPDRFSGSGSGTDFTLTISSLQAEDVAVYYCQQSKEDPR

TFGQGTKLEIKGGGGSGGGGSGGGGSEVQLVQSGAEVKKPGASVKVSCKA

SGYTFTDYNMDWVRQAPGQGLEWIGDINPNNGGTLYNQKFRGRVTLTVDK

SISTAYMELSRLRSDDTAVYYCARSEVFYGNYADYWGQGTTVTVSS.

B7H6-4 Single-Chain Antibody (SEQ ID NO: 31)
DIVLTQSPDSLAVSLGERATINCKASQSVDYDGDSYMNWYQQKPGQPPKL

LIYAASTLHSGVPDRFSGSGSGTDFTLTISSLQAEDVAVYYCQQSKEDPR

TFGQGTKLEIKGGGGSGGGGSGGGGSEVQLVQSGAEVKKPGASVKVSCKA

SGYTFTDYNMDWVRQAPGKGLEWIGDINPNNGGTLYNQKFRGRVTLTVDK

SISTAYMELSRLRSDDTAVYYCARSEVFYGNYADYWGQGTTVTVSS.

B7H6-5 Single-Chain Antibody (SEQ ID NO: 32)
DIVLTQSPDSLAVSLGERATINCKASQSVDYDGDSYMNWYQQKPGQPPKL

LIYAASTLHSGIPDRFSGSGSGTDFTLTISSLQAEDVAVYYCQQSKEDPR

TFGQGTKLEIKGGGGSGGGGSGGGGSEVQLVQSGAEVKKPGASVKVSCKA

SGYTFTDYNMDWVRQAPGQGLEWMGDINPNNGGTLYNQKFRGRVTMTVDT

SISTAYMELSRLRSDDTAVYYCARSEVFYGNYADYWGQGTTVTVSS.

B7H6-6 Single-Chain Antibody (SEQ ID NO: 33)
DIVLTQSPDSLAVSLGERATINCKASQSVDYDGDSYMNWYQQKPGQPPKL

LIYAASTLHSGIPDRFSGSGSGTDFTLTISSLQAEDVAVYYCQQSKEDPR

TFGQGTKLEIKGGGGSGGGGSGGGGSEVQLVQSGAEVKKPGASVKVSCKA

SGYTFTDYNMDWVRQAPGQGLEWIGDINPNNGGTLYNQKFRGRVTLTVDT

SISTAYMELSRLRSDDTAVYYCARSEVFYGNYADYWGQGTTVTVSS.

B7H6-7 Single-Chain Antibody (SEQ ID NO: 34)
DIVLTQSPDSLAVSLGERATINCKASQSVDYDGDSYMNWYQQKPGQPPKL

LIYAASTLHSGIPDRFSGSGSGTDFTLTISSLQAEDVAVYYCQQSKEDPR

TFGQGTKLEIKGGGGSGGGGSGGGGSEVQLVQSGAEVKKPGASVKVSCKA

SGYTFTDYNMDWVRQAPGQGLEWIGDINPNNGGTLYNQKFRGRVTLTVDK

SISTAYMELSRLRSDDTAVYYCARSEVFYGNYADYWGQGTTVTVSS.

B7H6-8 Single-Chain Antibody (SEQ ID NO: 35)
DIVLTQSPDSLAVSLGERATINCKASQSVDYDGDSYMNWYQQKPGQPPKL

LIYAASTLHSGIPDRFSGSGSGTDFTLTISSLQAEDVAVYYCQQSKEDPR

TFGQGTKLEIKGGGGSGGGGSGGGGSEVQLVQSGAEVKKPGASVKVSCKA

SGYTFTDYNMDWVRQAPGKGLEWIGDINPNNGGTLYNQKFRGRVTLTVDK

SISTAYMELSRLRSDDTAVYYCARSEVFYGNYADYWGQGTTVTVSS.

B7H6-9 Single-Chain Antibody (SEQ ID NO: 36)
DIVLTQTPLSLSVTPGQPASISCKASQSVDYDGDSYMNWYLQKPGQPPQL

LIYAASTLHSGVPDRFSGSGSGTDFTLKISRVEAEDVGVYYCQQSKEDPR

TFGQGTKLEIKGGGGSGGGGSGGGGSEVQLVQSGAEVKKPGASVKVSCKA

SGYTFTDYNMDWVRQAPGQGLEWMGDINPNNGGTLYNQKFRGRVTMTVDT

SISTAYMELSRLRSDDTAVYYCARSEVFYGNYADYWGQGTTVTVSS.

B7H6-10 Single-Chain Antibody (SEQ ID NO: 37)
DIVLTQTPLSLSVTPGQPASISCKASQSVDYDGDSYMNWYLQKPGQPPQL

LIYAASTLHSGVPDRFSGSGSGTDFTLKISRVEAEDVGVYYCQQSKEDPR

TFGQGTKLEIKGGGGSGGGGSGGGGSEVQLVQSGAEVKKPGASVKVSCKA

-continued

SGYTFTDYNMDWVRQAPGQGLEWIGDINPNNGGTLYNQKFRGRVTLTVDT

SISTAYMELSRLRSDDTAVYYCARSEVFYGNYADYWGQGTTVTVSS.

B7H6-11 Single-Chain Antibody (SEQ ID NO: 38)
DIVLTQTPLSLSVTPGQPASISCKASQSVDYDGDSYMNWYLQKPGQPPQL

LIYAASTLHSGVPDRFSGSGSGTDFTLKISRVEAEDVGVYYCQQSKEDPR

TFGQGTKLEIKGGGGSGGGGSGGGGSEVQLVQSGAEVKKPGASVKVSCKA

SGYTFTDYNMDWVRQAPGQGLEWIGDINPNNGGTLYNQKFRGRVTLTVDK

SISTAYMELSRLRSDDTAVYYCARSEVFYGNYADYWGQGTTVTVSS.

B7H6-12 Single-Chain Antibody (SEQ ID NO: 39)
DIVLTQTPLSLSVTPGQPASISCKASQSVDYDGDSYMNWYLQKPGQPPQL

LIYAASTLHSGVPDRFSGSGSGTDFTLKISRVEAEDVGVYYCQQSKEDPR

TFGQGTKLEIKGGGGSGGGGSGGGGSEVQLVQSGAEVKKPGASVKVSCKA

SGYTFTDYNMDWVRQAPGKGLEWIGDINPNNGGTLYNQKFRGRVTLTVDK

SISTAYMELSRLRSDDTAVYYCARSEVFYGNYADYWGQGTTVTVSS.

B7H6-13 Single-Chain Antibody (SEQ ID NO: 40)
DIVLTQTPLSLSVTPGQPASISCKASQSVDYDGDSYMNWYLQKPGQPPQL

LIYAASTLHSGIPDRFSGSGSGTDFTLKISRVEAEDVGVYYCQQSKEDPR

TFGQGTKLEIKGGGGSGGGGSGGGGSEVOLVOSGAEVKKPGASVKVSCKA

SGYTFTDYNMDWVRQAPGQGLEWMGDINPNNGGTLYNQKFRGRVTMTVDT

SISTAYMELSRLRSDDTAVYYCARSEVFYGNYADYWGQGTTVTVSS.

B7H6-14 Single-Chain Antibody (SEQ ID NO: 41)
DIVLTQTPLSLSVTPGQPASISCKASQSVDYDGDSYMNWYLQKPGQPPQL

LIYAASTLHSGIPDRFSGSGSGTDFTLKISRVEAEDVGVYYCQQSKEDPR

TFGQGTKLEIKGGGGSGGGGSGGGGSEVQLVQSGAEVKKPGASVKVSCKA

SGYTFTDYNMDWVRQAPGQGLEWIGDINPNNGGTLYNQKFRGRVTLTVDT

SISTAYMELSRLRSDDTAVYYCARSEVFYGNYADYWGQGTTVTVSS.

B7H6-15 Single-Chain Antibody (SEQ ID NO: 42)
DIVLTQTPLSLSVTPGQPASISCKASQSVDYDGDSYMNWYLQKPGQPPQL

LIYAASTLHSGIPDRFSGSGSGTDFTLKISRVEAEDVGVYYCQQSKEDPR

TFGQGTKLEIKGGGGSGGGGSGGGGSEVQLVQSGAEVKKPGASVKVSCKA

SGYTFTDYNMDWVRQAPGQGLEWIGDINPNNGGTLYNQKFRGRVTLTVDK

SISTAYMELSRLRSDDTAVYYCARSEVFYGNYADYWGQGTTVTVSS.

B7H6-16 Single-Chain Antibody (SEQ ID NO: 43)
DIVLTQTPLSLSVTPGQPASISCKASQSVDYDGDSYMNWYLQKPGQPPQL

LIYAASTLHSGIPDRFSGSGSGTDFTLKISRVEAEDVGVYYCQQSKEDPR

TFGQGTKLEIKGGGGSGGGGSGGGGSEVQLVQSGAEVKKPGASVKVSCKA

SGYTFTDYNMDWVRQAPGKGLEWIGDINPNNGGTLYNQKFRGRVTLTVDK

SISTAYMELSRLRSDDTAVYYCARSEVFYGNYADYWGQGTTVTVSS.

B7H6-17 Single-Chain Antibody (SEQ ID NO: 44)
DIVLTQSPVSLAVPLGQRATISCKASQSVDYDGDSYMNWYQQKPGQPPKL

LIYAASTLHSGIPVRFSGSGSGTDFTLNIHPVEEEDAASYYCQQSKEDPR

TFGGGTKLEIKGGGGSGGGGSGGGGSEVLLQQSGPEVVKPGASVKITCKA

SGYTFTDYNMDWVKQSHGKSLEWIGDINPNNAGTLYNQKFRGRVTLIVDK

SSSTAYMELRSLTSDDTAVYYCARSEVFYGNYADYWGQGTTLTVSS.

B7H6-18 Single-Chain Antibody (SEQ ID NO: 45)
DIVLTQSPVSLAVPLGQRATISCKASQSVDYDADSYMNWYQQKPGQPPKL

LIYAASTLHSGIPVRFSGSGSGTDFTLNIHPVEEEDAASYYCQQSKEDPR

TFGGGTKLEIKGGGGSGGGGSGGGGSEVLLQQSGPEVVKPGASVKITCKA

SGYTFTDYNMDWVKQSHGKSLEWIGDINPNNGGTLYNQKFRGRVTLIVDK

SSSTAYMELRSLTSDDTAVYYCARSEVFYGNYADYWGQGTTLTVSS.

Amino Acid Sequence of First Fc Region (SEQ ID NO: 47)
EPKSCDKTHTCPPCPAPEAAGGPSVFLFPPKPKDTLMISRTPEVTCVVVD

VSHEDPEVKFNWYVDGVEVHNAKTKPREEQYNSTYRVVSVLTVLHQDWLN

GKEYKCKVSNKALPAPIEKTISKAKGQPREPQVYTLPPCRDELTKNQVSL

WCLVKGFYPSDIAVEWESNGQPENNYKTTPPVLDSDGSFFLYSKLTVDKS

RWQQGNVFSCSVMHEALHNHYTQKSLSLSPGK.

Amino Acid Sequence of Second Fc Region (SEQ ID NO: 48)
EPKSCDKTHTCPPCPAPEAAGGPSVFLFPPKPKDTLMISRTPEVTCVVVD

VSHEDPEVKFNWYVDGVEVHNAKTKPREEQYNSTYRVVSVLTVLHQDWLN

GKEYKCKVSNKALPAPIEKTISKAKGQPREPQVCTLPPSRDELTKNQVSL

SCAVKGFYPSDIAVEWESNGQPENNYKTTPPVLDSDGSFFLVSKLTVDKS

RWQQGNVFSCSVMHEALHNHYTQKSLSLSPGK.

Example 2: Expression and Purification of CD3xB7H6 Bispecific Antibodies

2.1 Expression of CD3xB7H6 Bispecific Antibody Molecules

Bispecific molecules binding to CD3 and B7H6 were prepared by transient transfection of ExpiCHO-S cells (Gibco, cat. No. A29127) with pTT5 vectors carrying the CD3xB7H6 chain encoding genes. The eighteen CD3xB7H6 chain encoding genes had anti-CD3 ScFv-Fc as set forth in SEQ ID NO: 49, and anti-B7H6 ScFv-Fc as set forth in SEQ ID NO: 50 to SEQ ID NO: 67, respectively. Specific experimental procedures are described below. One day before the transfection, a cell density of the ExpiCHO-S cells was adjusted to (3-4)×$10^6$/mL and incubated overnight under the conditions of 37° C. and 8% $CO_2$, with shaking at 120 rpm. On the day of the transfection, when the cells were grown to a cell density of 7×$10^6$ to 1×$10^7$/mL and had a viability greater than 95%, the transfection began. The cells were diluted to a cell density of 6×$10^6$/mL with fleshly pre-warmed ExpiCHO medium (Gibco, cat. No. A2910002). Plasmids containing CD3 polypeptide chains and B7H6 polypeptide chains were transfected into the ExpiCHO-S cells at a mass ratio of 1:1 using ExpiFectamine CHO transfection reagent (Gibco, cat. No. A29129) and incubated under the conditions of 37° C. and 8% $CO_2$, with shaking at 120 rpm. 18 to 22 hours after the transfection, Expi-Fectamine CHO Enhancer and ExpiCHO Feed were mixed and immediately added into the transfected cells, mixed well, and the mixture was incubated at 32° C., 5% $CO_2$, with shaking at 120 min. Five days after the transfection, the cells were supplemented with 8 ml, of ExpiCHO Feed, mixed well, and incubated. The changes in cell number and cell viability were observed every day. After the cell viability has decreased to less than 80 or the cells had been cultured for 10-14 days, the cells were harvested through centrifugation, and the supernatant was purified or frozen at −80° C. for later use.

2.2 Purification of CD3xB7H6 Bispecific Antibody Molecules 2.1 The obtained supernatant was filtered with a 0.22 μm filter membrane, and the Fc domain-containing, antibodies were captured from the expression supernatant using a Mahselect prism A affinity chromatography column (GE, cat. No. 17549854). After the chromatography column was equilibrated with phosphate buffer (pH 7.2), the supernatant was passed through the affinity chromatography column, eluted with elution buffer (100 mM citric acid, pH 2.7), and finally concentrated and replaced with PBS buffer. The purified antibodies had a purity above 95%, as identified by means of SDS-PAGE.

CD3 ScFv-Fc Amino Acid Sequence (SEQ ID NO: 49)
MDIQMTQSPSSLSASVGDRVTITCRASQDIRNYLNWYQQKPGKAPKLLIY
YTSRLESGVPSRFSGSGSGTDYTLTISSLQPEDFATYYCQQGNTLPWTFG
QGTKVEIKGGGGSGGGGSGGGGSEVQLVESGGGLVQPGGSLRLSCAASGY
SFTGYTMNWVRQAPGKGLEWVALINPYKGVSTYNQKFKDRFTISVDKSKN
TAYLQMNSLRAEDTAVYYCARSGYYGDSDWYFDVWGQGTLVTVSSEPKSC
DKTHTCPPCPAPEAAGGPSVFLFPPKPKDTLMISRTPEVTCVVVDVSHED
PEVKFNWYVDGVEVHNAKTKPREEQYNSTYRVVSVLTVLHQDWLNGKEYK
CKVSNKALPAPIEKTISKAKGQPREPQVYTLPPCRDELTKNQVSLWCLVK
GFYPSDIAVEWESNGQPENNYKTTPPVLDSDGSFFLYSKLTVDKSRWQQG
NVFSCSVMHEALHNHYTQKSLSLSPGK.

B7H6-1 ScFv-Fc Amino Acid Sequence (SEQ ID NO: 50)
DIVLTQSPDSLAVSLGERATINCKASQSVDYDGDSYMNWYQQKPGQPPKL
LIYAASTLHSGVPDRFSGSGSGTDFTLTISSLQAEDVAVYYCQQSKEDPR
TFGQGTKLEIKGGGGSGGGGSGGGGSEVQLVQSGAEVKKPGASVKVSCKA
SGYTFTDYNMDWVRQAPGQGLEWMGDINPNNGGTLYNQKFRGRVTMTVDT
SISTAYMELSRLRSDDTAVYYCARSEVFYGNYADYWGQGTTVTVSSEPKS
CDKTHTCPPCPAPEAAGGPSVFLFPPKPKDTLMISRTPEVTCVVVDVSHE
DPEVKFNWYVDGVEVHNAKTKPREEQYNSTYRVVSVLTVLHQDWLNGKEY
KCKVSNKALPAPIEKTISKAKGQPREPQVCTLPPSRDELTKNQVSLSCAV
KGFYPSDIAVEWESNGQPENNYKTTPPVLDSDGSFFLVSKLTVDKSRWQQ
GNVFSCSVMHEALHNHYTQKSLSLSPGK.

B7H6-2 SCE-Fc Amino Acid Sequence (SEQ ID NO: 51)
DIVLTQSPDSLAVSLGERATINCKASQSVDYDGDSYMNWYQQKPGQPPKL
LIYAASTLHSGVPDRFSGSGSGTDFTLTISSLQAEDVAVYYCQQSKEDPR
TFGQGTKLEIKGGGGSGGGGSGGGGSEVQLVQSGAEVKKPGASVKVSCKA
SGYTFTDYNMDWVRQAPGQGLEWIGDINPNNGGTLYNOKFRGRVTLTVDT
SISTAYMELSRLRSDDTAVYYCARSEVFYGNYADYWGQGTTVTVSSEPKS
CDKTHTCPPCPAPEAAGGPSVFLFPPKPKDTLMISRTPEVTCVVVDVSHE
DPEVKFNWYVDGVEVHNAKTKPREEQYNSTYRVVSVLTVLHQDWLNGKEY
KCKVSNKALPAPIEKTISKAKGQPREPQVCTLPPSRDELTKNQVSLSCAV
KGFYPSDIAVEWESNGQPENNYKTTPPVLDSDGSFFLVSKLTVDKSRWQQ
GNVFSCSVMHEALHNHYTQKSLSLSPGK.

B7H6-3 ScFv-Fc Amino Acid Sequence (SEQ ID NO: 52)
DIVLTQSPDSLAVSLGERATINCKASQSVDYDGDSYMNWYQQKPGQPPKL
LIYAASTLHSGVPDRFSGSGSGTDFTLTISSLQAEDVAVYYCQQSKEDPR
TFGQGTKLEIKGGGGSGGGGSGGGGSEVQLVQSGAEVKKPGASVKVSCKA
SGYTFTDYNMDWVRQAPGQGLEWIGDINPNNGGTLYNQKFRGRVTLTVDK
SISTAYMELSRLRSDDTAVYYCARSEVFYGNYADYWGQGTTVTVSSEPKS
CDKTHTCPPCPAPEAAGGPSVFLFPPKPKDTLMISRTPEVTCVVVDVSHE
DPEVKFNWYVDGVEVHNAKTKPREEQYNSTYRVVSVLTVLHQDWLNGKEY
KCKVSNKALPAPIEKTISKAKGQPREPQVCTLPPSRDELTKNQVSLSCAV
KGFYPSDIAVEWESNGQPENNYKTTPPVLDSDGSFFLVSKLTVDKSRWQQ
GNVFSCSVMHEALHNHYTQKSLSLSPGK.

B7H6-4 ScFv-Fc Amino Acid Sequence (SEQ ID NO: 53)
DIVLTQSPDSLAVSLGERATINCKASQSVDYDGDSYMNWYQQKPGQPPKL
LIYAASTLHSGVPDRFSGSGSGTDFTLTISSLQAEDVAVYYCQQSKEDPR -continued TFGQGTKLEIKGGGGSGGGGSGGGGSEVQLVQSGAEVKKPGASVKVSCKA
SGYTFTDYNMDWVRQAPGKGLEWIGDINPNNGGTLYNQKFRGRVTLTVDK
SISTAYMELSRLRSDDTAVYYCARSEVFYGNYADYWGQGTTVTVSSEPKS
CDKTHTCPPCPAPEAAGGPSVFLFPPKPKDTLMISRTPEVTCVVVDVSHE
DPEVKFNWYVDGVEVHNAKTKPREEQYNSTYRVVSVLTVLHQDWLNGKEY
KCKVSNKALPAPIEKTISKAKGQPREPQVCTLPPSRDELTKNQVSLSCAV
KGFYPSDIAVEWESNGQPENNYKTTPPVLDSDGSFFLVSKLTVDKSRWQQ
GNVFSCSVMHEALHNHYTQKSLSLSPGK.

B7H6-5 ScFv-Fc Amino Acid Sequence (SEQ ID NO: 54)
DIVLTQSPDSLAVSLGERATINCKASQSVDYDGDSYMNWYQQKPGQPPKL
LIYAASTLHSGIPDRFSGSGSGTDFTLTISSLQAEDVAVYYCQQSKEDPR
TFGQGTKLEIKGGGGSGGGGSGGGGSEVQLVQSGAEVKKPGASVKVSCKA
SGYTFTDYNMDWVRQAPGQGLEWMGDINPNNGGTLYNQKFRGRVTMTVDT
SISTAYMELSRLRSDDTAVYYCARSEVFYGNYADYWGQGTTVTVSSEPKS
CDKTHTCPPCPAPEAAGGPSVFLFPPKPKDTLMISRTPEVTCVVVDVSHE
DPEVKFNWYVDGVEVHNAKTKPREEQYNSTYRVVSVLTVLHQDWLNGKEY
KCKVSNKALPAPIEKTISKAKGQPREPQVCTLPPSRDELTKNQVSLSCAV
KGFYPSDIAVEWESNGQPENNYKTTPPVLDSDGSFELVSKLTVDKSRWQQ
GNVFSCSVMHEALHNHYTQKSLSLSPGK.

B7H6-6 ScFV-Fc Amino Acid Sequence (SEQ ID NO: 55)
DIVLTQSPDSLAVSLGERATINCKASQSVDYDGDSYMNWYQQKPGQPPKL
LIYAASTLHSGIPDRFSGSGSGTDFTLTISSLQAEDVAVYYCQQSKEDPR
TFGQGTKLEIKGGGGSGGGGSGGGGSEVQLVQSGAEVKKPGASVKVSCKA
SGYTFTDYNMDWVRQAPGQGLEWIGDINPNNGGTLYNQKFRGRVTLTVDT
SISTAYMELSRLRSDDTAVYYCARSEVFYGNYADYWGQGTTVTVSSEPKS
CDKTHTCPPCPAPEAAGGPSVFLFPPKPKDTLMISRTPEVTCVVVDVSHE
DPEVKFNWYVDGVEVHNAKTKPREEQYNSTYRVVSVLTVLHQDWLNGKEY
KCKVSNKALPAPIEKTISKAKGQPREPQVCTLPPSRDELTKNQVSLSCAV
KGFYPSDIAVEWESNGQPENNYKTTPPVLDSDGSFFLVSKLTVDKSRWQQ
GNVFSCSVMHEALHNHYTQKSLSLSPGK.

B7H6-7 ScFv-Fc Amino Acid Sequence (SEQ ID NO: 56)
DIVLTQSPDSLAVSLGERATINCKASQSVDYDGDSYMNWYQQKPGQPPKL
LIYAASTLHSGIPDRFSGSGSGTDFTLTISSLQAEDVAVYYCQQSKEDPR
TFGQGTKLEIKGGGGSGGGGSGGGGSEVQLVQSGAEVKKPGASVKVSCKA
SGYTFTDYNMDWVRQAPGQGLEWIGDINPNNGGTLYNQKFRGRVTLTVDK
SISTAYMELSRLRSDDTAVYYCARSEVFYGNYADYWGQGTTVTVSSEPKS
CDKTHTCPPCPAPEAAGGPSVFLFPPKPKDTLMISRTPEVTCVVVDVSHE -continued DPEVKFNWYVDGVEVHNAKTKPREEQYNSTYRVVSVLTVLHQDWLNGKEY
KCKVSNKALPAPIEKTISKAKGQPREPQVCTLPPSRDELTKNQVSLSCAV
KGFYPSDIAVEWESNGQPENNYKTTPPVLDSDGSFFLVSKLTVDKSRWQQ
GNVFSCSVMHEALHNHYTQKSLSLSPGK.

B7H6-8 ScFV-Fc Amino Acid Sequence (SEQ ID NO: 57)
DIVLTQSPDSLAVSLGERATINCKASQSVDYDGDSYMNWYQQKPGQPPKL
LIYAASTLHSGIPDRFSGSGSGTDFTLTISSLQAEDVAVYYCQQSKEDPR
TFGQGTKLEIKGGGGSGGGGSGGGGSEVQLVQSGAEVKKPGASVKVSCKA
SGYTFTDYNMDWVRQAPGKGLEWIGDINPNNGGTLYNQKFRGRVTLTVDK
SISTAYMELSRLRSDDTAVYYCARSEVFYGNYADYWGQGTTVTVSSEPKS
CDKTHTCPPCPAPEAAGGPSVFLFPPKPKDTLMISRTPEVTCVVVDVSHE
DPEVKFNWYVDGVEVHNAKTKPREEQYNSTYRVVSVLTVLHQDWLNGKEY
KCKVSNKALPAPIEKTISKAKGQPREPQVCTLPPSRDELTKNQVSLSCAV
KGFYPSDIAVEWESNGQPENNYKTTPPVLDSDGSFFLVSKLTVDKSRWQQ
GNVFSCSVMHEALHNHYTQKSLSLSPGK.

B7H6-9 ScFV-Fc Amino Acid Sequence (SEQ ID NO: 58)
DIVLTQTPLSLSVTPGQPASISCKASQSVDYDGDSYMNWYLQKPGQPPQL
LIYAASTLHSGVPDRFSGSGSGTDFTLKISRVEAEDVGVYYCQQSKEDPR
TFGQGTKLEIKGGGGSGGGGGGGGSEVQLVQSGAEVKKPGASVKVSCKAS
GYTFTDYNMDWVRQAPGQGLEWMGDINPNNGGTLYNQKFRGRVTMTVDTS
ISTAYMELSRLRSDDTAVYYCARSEVFYGNYADYWGQGTTVTVSSEPKSC
DKTHTCPPCPAPEAAGGPSVFLFPPKPKDTLMISRTPEVTCVVVDVSHED
PEVKFNWYVDGVEVHNAKTKPREEQYNSTYRVVSVLTVLHQDWLNGKEYK
CKVSNKALPAPIEKTISKAKGQPREPQVCTLPPSRDELTKNQVSLSCAVK
GFYPSDIAVEWESNGQPENNYKTTPPVLDSDGSFFLVSKLTVDKSRWQQG
NVFSCSVMHEALHNHYTQKSLSLSPGK.

B7H6-10 ScFv-Fc Amino Acid Sequence (SEQ ID NO: 59)
DIVLTQTPLSLSVTPGQPASISCKASQSVDYDGDSYMNWYLQKPGQPPQL
LIYAASTLHSGVPDRFSGSGSGTDFTLKISRVEAEDVGVYYCQQSKEDPR
TFGQGTKLEIKGGGGSGGGGSGGGGSEVQLVQSGAEVKKPGASVKVSCKA
SGYTFTDYNMDWVRQAPGQGLEWIGDINPNNGGTLYNQKFRGRVTLTVDT
SISTAYMELSRLRSDDTAVYYCARSEVFYGNYADYWGQGTTVTVSSEPKS
CDKTHTCPPCPAPEAAGGPSVFLFPPKPKDTLMISRTPEVTCVVVDVSHE
DPEVKFNWYVDGVEVHNAKTKPREEQYNSTYRVVSVLTVLHQDWLNGKEY
KCKVSNKALPAPIEKTISKAKGQPREPQVCTLPPSRDELTKNQVSLSCAV -continued

KGFYPSDIAVEWESNGQPENNYKTTPPVLDSDGSFFLVSKLTVDKSRWQQ

GNVFSCSVMHEALHNHYTQKSLSLSPGK.

B7H6-11 ScFV-Fc Amino Acid Sequence (SEQ ID NO: 60)
DIVLTQTPLSLSVTPGQPASISCKASQSVDYDGDSYMNWYLQKPGQPPQL
LIYAASTLHSGVPDRFSGSGSGTDFTLKISRVEAEDVGVYYCQQSKEDPR
TFGQGTKLEIKGGGGSGGGGSGGGGSEVQLVQSGAEVKKPGASVKVSCKA
SGYTFTDYNMDWVRQAPGQGLEWIGDINPNNGGTLYNQKFRGRVTLTVDK
SISTAYMELSRLRSDDTAVYYCARSEVFYGNYADYWGQGTTVTVSSEPKS
CDKTHTCPPCPAPEAAGGPSVFLFPPKPKDTLMISRTPEVTCVVVDVSHE
DPEVKFNWYVDGVEVHNAKTKPREEQYNSTYRVVSVLIVLHQDWLNGKEY
KCKVSNKALPAPIEKTISKAKGQPREPQVCTLPPSRDELTKNQVSLSCAV
KGFYPSDIAVEWESNGQPENNYKTTPPVLDSDGSFFLVSKLTVDKSRWQQ
GNVFSCSVMHEALHNHYTQKSLSLSPGK.

B7H6-12 ScFv-Fc Amino Acid Sequence (SEQ ID NO: 61)
DIVLTQTPLSLSVTPGQPASISCKASQSVDYDGDSYMNWYLQKPGQPPQL
LIYAASTLHSGVPDRFSGSGSGTDFTLKISRVEAEDVGVYYCQQSKEDPR
TFGQGTKLEIKGGGGSGGGGSGGGGSEVQLVQSGAEVKKPGASVKVSCKA
SGYTFTDYNMDWVRQAPGKGLEWIGDINPNNGGTLYNQKFRGRVTLTVDK
SISTAYMELSRLRSDDTAVYYCARSEVFYGNYADYWGQGTTVTVSSEPKS
CDKTHTCPPCPAPEAAGGPSVFLFPPKPKDTLMISRTPEVTCVVVDVSHE
DPEVKFNWYVDGVEVHNAKTKPREEQYNSTYRVVSVLTVLHQDWLNGKEY
KCKVSNKALPAPIEKTISKAKGQPREPQVCTLPPSRDELTKNQVSLSCAV
KGFYPSDIAVEWESNGQPENNYKTTPPVLDSDGSFFLVSKLTVDKSRWQQ
GNVFSCSVMHEALHNHYTQKSLSLSPGK.

B7H6-13 ScFv-Fc Amino Acid Sequence (SEQ ID NO: 62)
DIVLTQTPLSLSVTPGQPASISCKASQSVDYDGDSYMNWYLQKPGQPPQL
LIYAASTLHSGIPDRFSGSGSGTDFTLKISRVEAEDVGVYYCQQSKEDPR
TFGQGTKLEIKGGGGSGGGGSGGGGSEVQLVQSGAEVKKPGASVKVSCKA
SGYTFTDYNMDWVRQAPGQGLEWMGDINPNNGGTLYNQKFRGRVTMTVDT
SISTAYMELSRLRSDDTAVYYCARSEVFYGNYADYWGQGTTVTVSSEPKS
CDKTHTCPPCPAPEAAGGPSVFLFPPKPKDTLMISRTPEVTCVVVDVSHE
DPEVKFNWYVDGVEVHNAKTKPREEQYNSTYRVVSVLTVLHQDWLNGKEY
KCKVSNKALPAPIEKTISKAKGQPREPQVCTLPPSRDELTKNQVSLSCAV
KGFYPSDIAVEWESNGQPENNYKTTPPVLDSDGSFFLVSKLTVDKSRWQQ
GNVFSCSVMHEALHNHYTQKSLSLSPGK.

B7H6-14 ScFv-Fc Amino Acid Sequence (SEQ ID NO: 63)
DIVLTQTPLSLSVTPGQPASISCKASQSVDYDGDSYMNWYLQKPGQPPQL
LIYAASTLHSGIPDRFSGSGSGTDFTLKISRVEAEDVGVYYCQQSKEDPR
TFGQGTKLEIKGGGGSGGGGSGGGGSEVQLVQSGAEVKKPGASVKVSCKA
SGYTFTDYNMDWVRQAPGQGLEWIGDINPNNGGTLYNQKFRGRVTLTVDT
SISTAYMELSRLRSDDTAVYYCARSEVFYGNYADYWGQGTTVTVSSEPKS
CDKTHTCPPCPAPEAAGGPSVFLFPPKPKDTLMISRTPEVTCVVVDVSHE
DPEVKFNWYVDGVEVHNAKTKPREEQYNSTYRVVSVLTVLHQDWLNGKEY
KCKVSNKALPAPIEKTISKAKGQPREPQVCTLPPSRDELTKNQVSLSCAV
KGFYPSDIAVEWESNGQPENNYKTTPPVLDSDGSFFLVSKLTVDKSRWQQ
GNVFSCSVMHEALHNHYTQKSLSLSPGK.

B7H6-15 ScFv-Fc Amino Acid Sequence (SEQ ID NO: 64)
DIVLTQTPLSLSVTPGQPASISCKASQSVDYDGDSYMNWYLQKPGQPPQL
LIYAASTLHSGIPDRFSGSGSGTDFTLKISRVEAEDVGVYYCQQSKEDPR
TFGQGTKLEIKGGGGSGGGGSGGGGSEVQLVQSGAEVKKPGASVKVSCKA
SGYTFTDYNMDWVRQAPGQGLEWIGDINPNNGGTLYNQKFRGRVTLTVDK
SISTAYMELSRLRSDDTAVYYCARSEVFYGNYADYWGQGTTVTVSSEPKS
CDKTHTCPPCPAPEAAGGPSVFLFPPKPKDTLMISRTPEVTCVVVDVSHE
DPEVKFNWYVDGVEVHNAKTKPREEQYNSTYRVVSVLTVLHQDWLNGKEY
KCKVSNKALPAPIEKTISKAKGQPREPQVCTLPPSRDELTKNQVSLSCAV
KGFYPSDIAVEWESNGQPENNYKTTPPVLDSDGSFFLVSKLTVDKSRWQQ
GNVFSCSVMHEALHNHYTQKSLSLSPGK.

B7H6-16 ScFv-Fc Amino Acid Sequence (SEQ ID NO: 65)
DIVLTQTPLSLSVTPGQPASISCKASQSVDYDGDSYMNWYLQKPGQPPQL
LIYAASTLHSGIPDRFSGSGSGTDFTLKISRVEAEDVGVYYCQQSKEDPR
TFGQGTKLEIKGGGGSGGGGSGGGGSEVQLVQSGAEVKKPGASVKVSCKA
SGYTFTDYNMDWVRQAPGKGLEWIGDINPNNGGTLYNQKFRGRVTLTVDK
SISTAYMELSRLRSDDTAVYYCARSEVFYGNYADYWGQGTTVTVSSEPKS
CDKTHTCPPCPAPEAAGGPSVFLFPPKPKDTLMISRTPEVTCVVVDVSHE
DPEVKFNWYVDGVEVHNAKTKPREEQYNSTYRVVSVLTVLHQDWLNGKEY
KCKVSNKALPAPIEKTISKAKGQPREPQVCTLPPSRDELTKNQVSLSCAV
KGFYPSDIAVEWESNGQPENNYKTTPPVLDSDGSFFLVSKLTVDKSRWQQ
GNVFSCSVMHEALHNHYTQKSLSLSPGK.

B7H6-17 ScFv-Fc Amino Acid Sequence (SEQ ID NO: 66)
DIVLTQSPVSLAVPLGQRATISCKASQSVDYDGDSYMNWYQQKPGQPPKL
LIYAASTLHSGIPVRFSGSGSGTDFTLNIHPVEEEDAASYYCQQSKEDPR -continued

```
TFGGGTKLEIKGGGGSGGGGSGGGGSEVLLQQSGPEVVKPGASVKITCKA

SGYTFTDYNMDWVKQSHGKSLEWIGDINPNNAGTLYNQKFRGRVTLIVDK

SSSTAYMELRSLTSDDTAVYYCARSEVFYGNYADYWGQGTTLTVSSEPKS

CDKTHTCPPCPAPEAAGGPSVFLFPPKPKDTLMISRTPEVTCVVVDVSHE

DPEVKFNWYVDGVEVHNAKTKPREEQYNSTYRVVSVLTVLHQDWLNGKEY

KCKVSNKALPAPIEKTISKAKGQPREPQVCTLPPSRDELTKNQVSLSCAV

KGFYPSDIAVEWESNGQPENNYKTTPPVLDSDGSFFLVSKLTVDKSRWQQ

GNVFSCSVMHEALHNHYTQKSLSLSPGK.
```

B7H6-18 ScFv-Fc Amino Acid Sequence

```
                                        (SEQ ID NO: 67)
DIVLTQSPVSLAVPLGQRATISCKASQSVDYDADSYMNWYQQKPGQPPKL

LIYAASTLHSGIPVRFSGSGSGTDFTLNIHPVEEEDAASYYCQQSKEDPR

TFGGGTKLEIKGGGGSGGGGSGGGGSEVLLQQSGPEVVKPGASVKITCKA

SGYTFTDYNMDWVKQSHGKSLEWIGDINPNNGGTLYNQKFRGRVTLIVDK

SSSTAYMELRSLTSDDTAVYYCARSEVFYGNYADYWGQGTTLTVSSEPKS

CDKTHTCPPCPAPEAAGGPSVFLFPPKPKDTLMISRTPEVTCVVVDVSHE

DPEVKFNWYVDGVEVHNAKTKPREEQYNSTYRVVSVLTVLHQDWLNGKEY

KCKVSNKALPAPIEKTISKAKGQPREPQVCTLPPSRDELTKNQVSLSCAV

KGFYPSDIAVEWESNGQPENNYKTTPPVLDSDGSFFLVSKLTVDKSRWQQ

GNVFSCSVMHEALHNHYTQKSLSLSPGK.
```

Example 3: Detection of Binding Activity of CD3xB7H6 Bispecific Antibodies to Antigen (ELISA)

In this example, the binding activity of CD3xB7H6 bispecific antibodies to a single antigen (the B7H6 antigen or the CD3 antigen) and the binding activity of the CD3xB7H6 bispecific antibodies simultaneously to the double antigens (the B7H6 antigen and the CD3 antigen) were detected, respectively. The specific experimental procedures are described below.

3.1 Determination of Binding Activity of CD3xB7H6 Bispecific Antibody to Single Antigen Human B7H6 (ACRO biosystems, cat. No. B76-H52H8) and human CD3 antigen (ACRO biosystems, cat. No. CDD-H52W1) were diluted to 2 μg/mL with coating buffer (35 mM $NaHCO_3$, 15 mM $Na_2CO_3$, pH 9.6), respectively. 100 μL of the diluted solution was added to each well of an ELISA plate at 4° C. overnight, and then washes with PBST (0.05% Tween 20-PBS, pH 7.2) 3 times. 300 μL of blocking buffer (1% BSA, 0.05% Tween20-PBS, pH 7.2) was added to the plate and allowed to stand at room temperature for 2 h, followed by washing with PBST three times. The corresponding bispecific antibody was added to each well and incubated at room temperature for 1 h, followed by washing with PBST three times. 100 μL of HRP-rabbit anti human IgG secondary antibody (Boster, cat. No. BA1070) diluted in blocking buffer was added to each well and incubated for 1 h at room temperature, followed by washing with PBST three times. TMB was added into each well. The plate was kept away from light at room temperature for 2-5 min, the reaction was stopped by adding 2 M sulfuric acid in each well, and finally OD450 values were read with microplate reader.

Figure 2A:
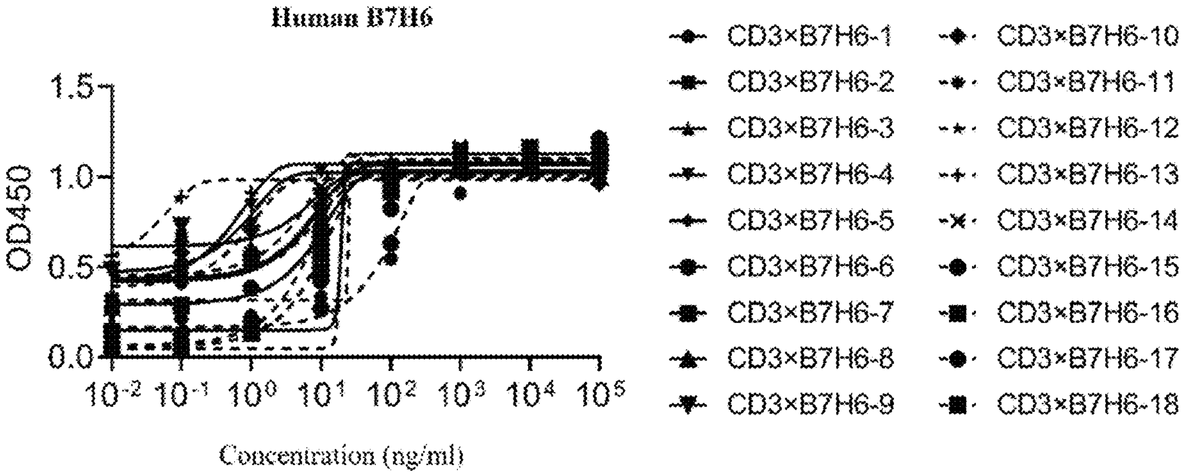
FIG. 2A is a binding analysis result graph of a CD3xB7H6 recombinant bispecific antibody binding to human B7H6 protein according to an embodiment of the present disclosure.
Figure 2B:
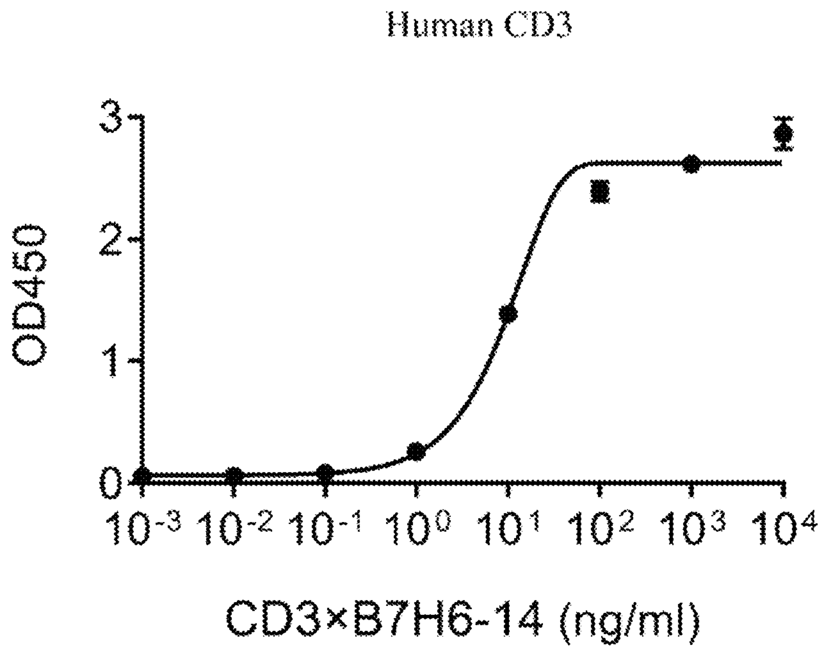
FIG. 2B is a binding analysis result graph of a CD3xB7H6 recombinant bispecific antibody binding to human CD3 protein according to an embodiment of the present disclosure.

Specific experimental results are shown in FIG. 2A. FIG. 2A shows the binding of CD3kB7H6 bispecific antibody molecules to B7H6 antigen, the CD3kB7H6 bispecific antibody molecules being composed of different B7H6 sequences and CD3 sequences. It can be seen from FIG. 2 that these bispecific antibody molecules can all bind to B7H6 antigen. Among them, CD3xB7H6-14 has the strongest binding, activity. Therefore, subsequent experiments mainly focus on CD3kB7H6-14. FIG. 2B shows that CD3xB7H6-14 bispecific antibody molecules can bind to CD3 antigen.

Figure 2C:
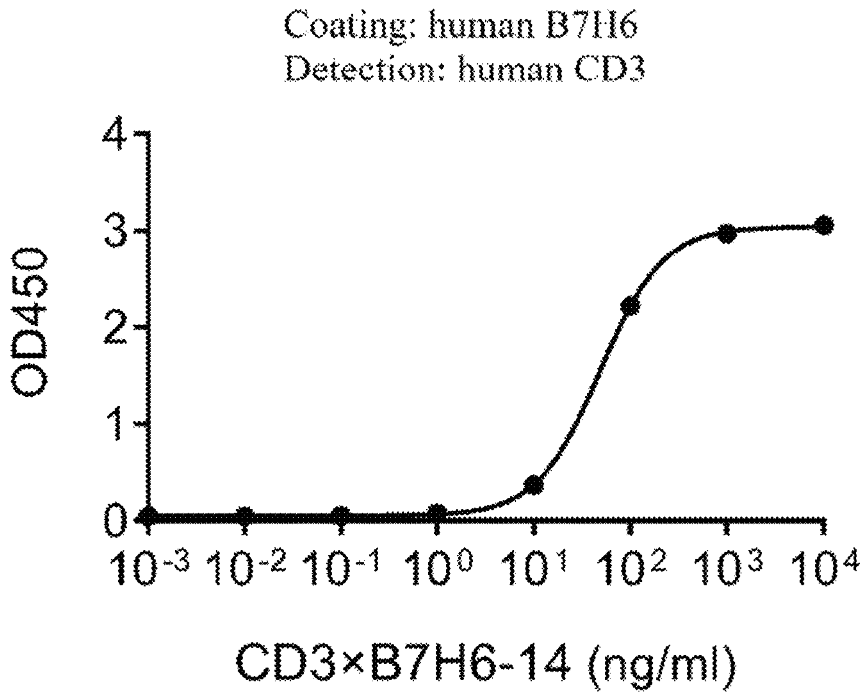
FIG. 2C is an ELISA detection result graph of a CD3xB7H6 recombinant bispecific antibody with B7H6 and human CD3 double antigen according to an embodiment of the present disclosure.

3.2 Determination of Binding Activity of CD3xB7H6 Bispecific Antibody and Double Antigen Human B7H6 (ACRO biosystems, cat. No. B76-H82Wb) was diluted to 2 μg/mL with coating buffer (35 mM. $NaHCO_3$, 15 mM $Na_2CO_3$, pH 9.6), and 100 μL of the diluted solution was added to each well of an ELISA date at 4° C. overnight. The plate was washed with PBST (0.05% Tween 20-PBS, pH 7.2) three times. 300 μL of blocking buffer (1% BSA, 0.05% TWeen20PBS, pH 7.2) was added to the plate and allowed to stand at room temperature for 2 h, followed by washing with PBST three times. The corresponding bispecific antibody was added to each well and incubated at room temperature for 1 h, followed by washing with PBST three times. 100 μL of human CD3 antigen (ACRO biosystems, cat. No. CDD-H52W1) diluted in blocking buffer was added to each well and incubated for 1 h at room temperature, followed by washing with PBST three times. 100 μL of HRP-anti-His tagged secondary antibody (Genscript, cat. No. A00612) diluted in blocking buffer was added to each well and incubated for 1 h at room temperature, followed by washing with PBST three times. TMB was added into each well. The plate was kept away from light at room temperature for 2-5 min. The reaction was stopped by adding 2 M sulfuric acid in each well, and finally, OD450 values were read with a microplate reader. The results are shown in FIG. 2C and show that as the concentration of the CD3xB7H6-14 bispecific antibody molecule increases, the OD450 reading increases, indicating that the bispecific antibody molecule can bind to both human CD3 and B7H6 antigens.

Example 4 In Vitro Killing Detection of Bispecific Antibody Molecules

4.1 Isolation of Human Peripheral Blood Mononuclear Cells (PBMCs)

Anticoagulated human peripheral blood was added into an equal volume of sterile PBS, and 25 mL of diluted peripheral blood was gently added onto 15 mL of lymph separation fluid (GE healthcare, cat. No. 17144003) in a 50 mL sterile centrifuge tube. The interface was kept clear without shaking during the whole process, followed by centrifuging at 21° C. for 30 min at 400 g, with the centrifuge increasing at speed 1 and decreasing at speed 0. After the centrifugation, the tube was divided into three layers, with the lymphocyte layer in the middle layer. The white membrane layer in the middle layer was sucked and added into a new 50 mL centrifuge tube, added with PBS to 50 mL after completion of suction, and then centrifugation was performed at 500 g for 10 min. The supernatant was discarded, 1 mL PBS was added to gently blow, PBS was added to 40 mL, and centrifugation was performed for 10 min at 250 g.

Supernatants were discarded after centrifugation, the remaining was resuspended with 1 mL of MACS buffer (0.5% BSA, 2.5 mM EDTA-PBS), and counted by dilution.

4.2 Isolation of Purified T-Cells

Human T Cells were Isolated from Peripheral Blood Using Magnetic Bead Sorting (Miltenyi, cat. No. 130096535). After PBMCs were collected, the supernatant was discarded, 40 μL of MACS buffer was added for every $10^7$ cells to resuspend the cells, then 10 μL of T Cell Biotin-Antibody Cocktail was added, mixed well, and incubated at 4° C. for 10 min. 30 μL of MACS buffer and 20 μL of T Cell MicroBead Cocktail were added per $10^7$ cells, mixed well, and incubated for 15 min at 4° C. The LS separation column was placed in the magnetic field, the separation column was wetted with 3 mL MACS buffer, the cell suspension was added to the separation column, after the centrifuge tube was rinsed with 1 mL MACS buffer, the separation column was added, and the effluent was collected. The column was washed with 3 mL MACS buffer and the effluent was collected. After mixing well, the cells were counted. 300 g of the cell suspension was centrifuged at 4° C. for 10 min and resuspended in a culture medium.

4.3 In Vitro Killing Detection of Adherent Tumor Cells

Adherently cultured tumor cells were digested and counted, and the cell density thereof was adjusted to $2\times10^5$/mL. RTCA instrument (Agilent) was activated to select instrument type DP and experiment mode, and to fill in cell information and medicament information. After entering the schedule set-up experiment step, 50 μL of fresh medium (89% RPMI 1640 medium+10% fetal bovine serum+1% Penicillin Streptomycin) was added to the plate, and the plate Was put into the instrument. The instrument was closed, and the first step initiated by clicking. The plate was taken out after the first step Was done, added with 100 μL, of cell suspension, and left to stand at room temperature for 15-30 min to prevent edge effect. Then, the plate was put into the instrument, and Start button was clicked. After the cells grew to the log phase, the procedure was stopped, 50 μL of purified T cells ($1\times10^6$/mL) and the bispecific antibodies at gradient concentrations were added, followed by clicking the Start button and performing the analysis after some time.

Figure 3A:
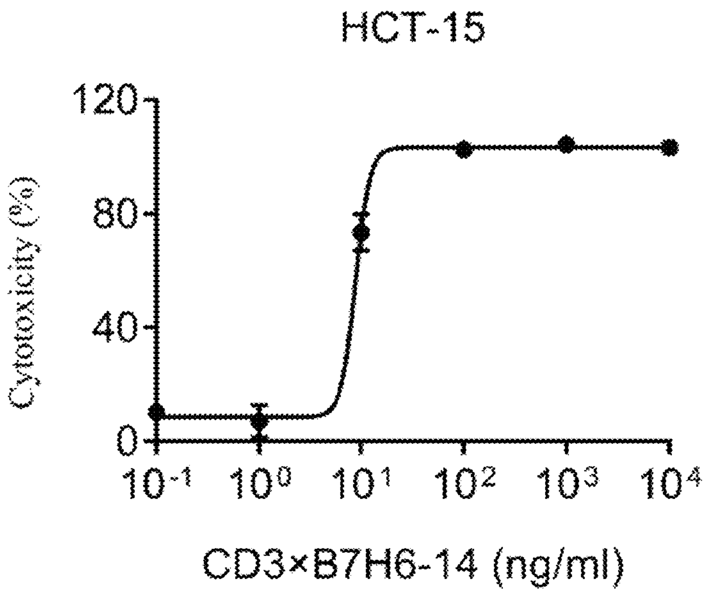
FIG. 3A is a graph showing the results of an in vitro cytotoxicity test analysis of a CD3xB7H6 recombinant bispecific antibody and T cells on HCT-15 cells according to an embodiment of the present disclosure.
Figure 3B:
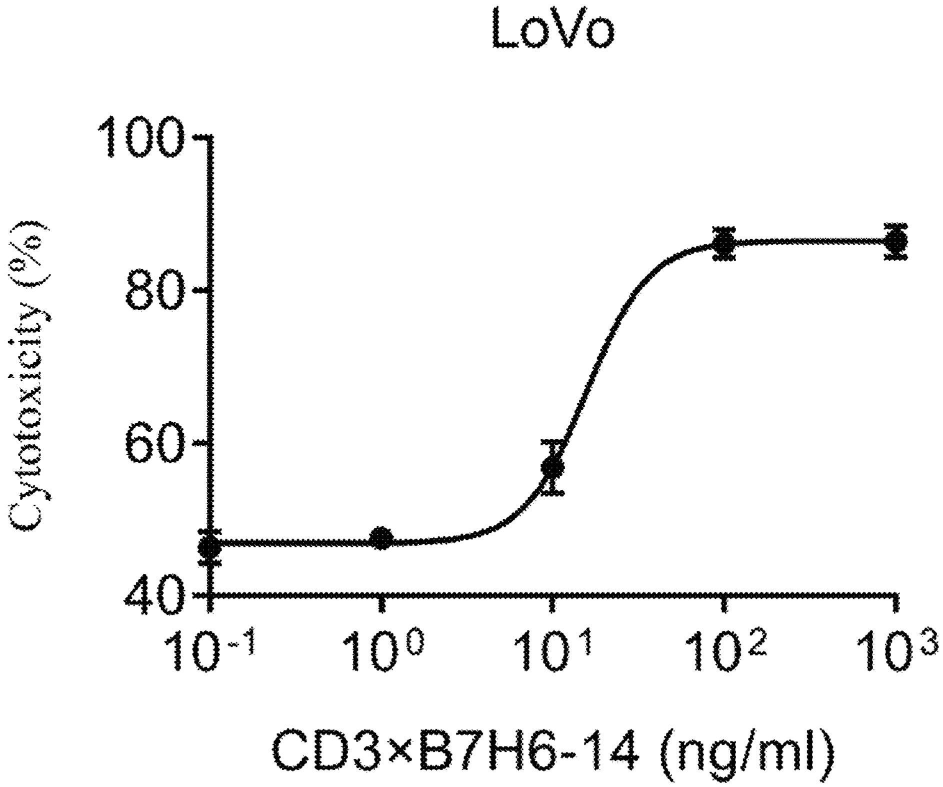
FIG. 3B is a graph showing the results of an in vitro cytotoxicity test analysis of a CD3xB7H6 recombinant bispecific antibody and T cells on LoVo cells according to an embodiment of the present disclosure.
Figure 3C:
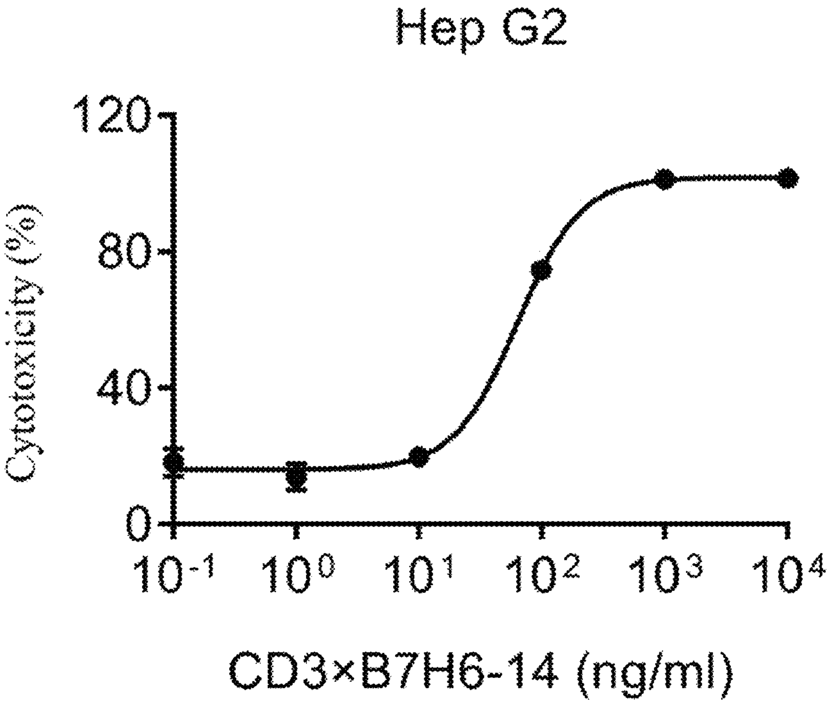
FIG. 3C is a graph showing the results of an in vitro cytotoxicity test of a CD3xB7H6 recombinant bispecific antibody and T cells on Hep G2 cells according to an embodiment of the present disclosure.
Figure 3D:
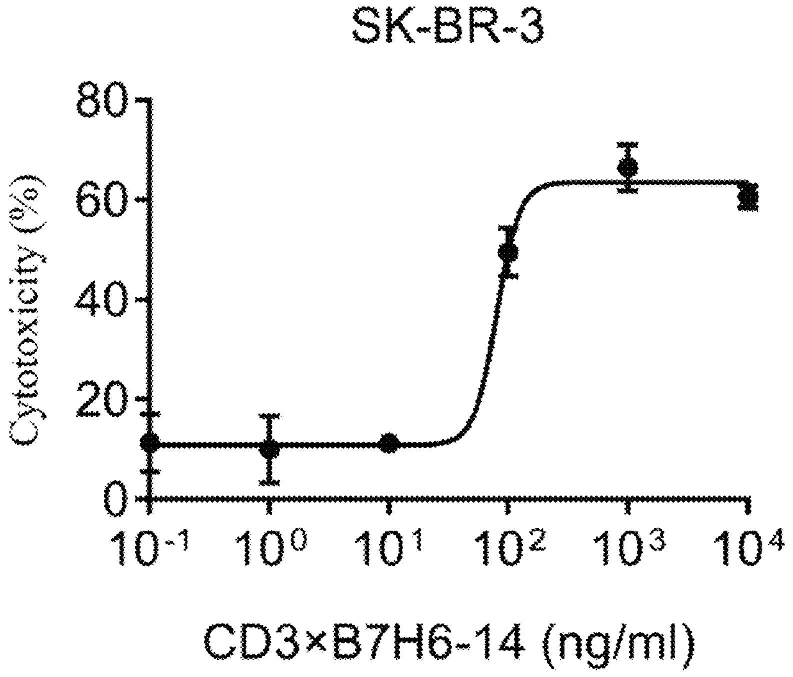
FIG. 3D is a graph showing the results of an in vitro cytotoxicity test of a CD3xB7H6 recombinant bispecific antibody and T cells on SK-BR-3 cells according to an embodiment of the present disclosure.

Specific experimental results are shown in the figures, in which the killing efficiency of T cells on HCT-15 cells (FIG. 3A), LoVo cells (FIG. 3B), Hep G2 cells (FIG. 3C), and SK-BR-3 cells (FIG. 3D) increased an increase in CD3xB7H6H4 bispecific antibody concentration, indicating that CD3kB7H6-14 can promote T cells to kill B7H6+ tumor cells.

Example 5: Detection of In Vitro Killing of Suspension Cells by the Luciferase Reaction After the luciferase-overexpressing tumor cells were collected, the cell density thereof was adjusted to $2\times10^5$/mL. T cells were isolated and purified, collected, purified, and adjusted to $5\times10^5$/mL, as described in Examples 4.1 and 4.2. 50 μL, of the tumor cells and 50 μL of purified T cells were plated in a 96-well flat bottom plate and added with the bispecific antibodies at gradient concentrations and mixed well. After incubation at 37° C., 5% $CO_2$ for 4 h, 100 μL (15 mg/mL) of fluorescein potassium salt solution (Goldbio, cat. No. LUCK-1G) was added to each well, mixed well quickly, and chemiluminescence values were detected with a microplate reader.

Figure 4A:
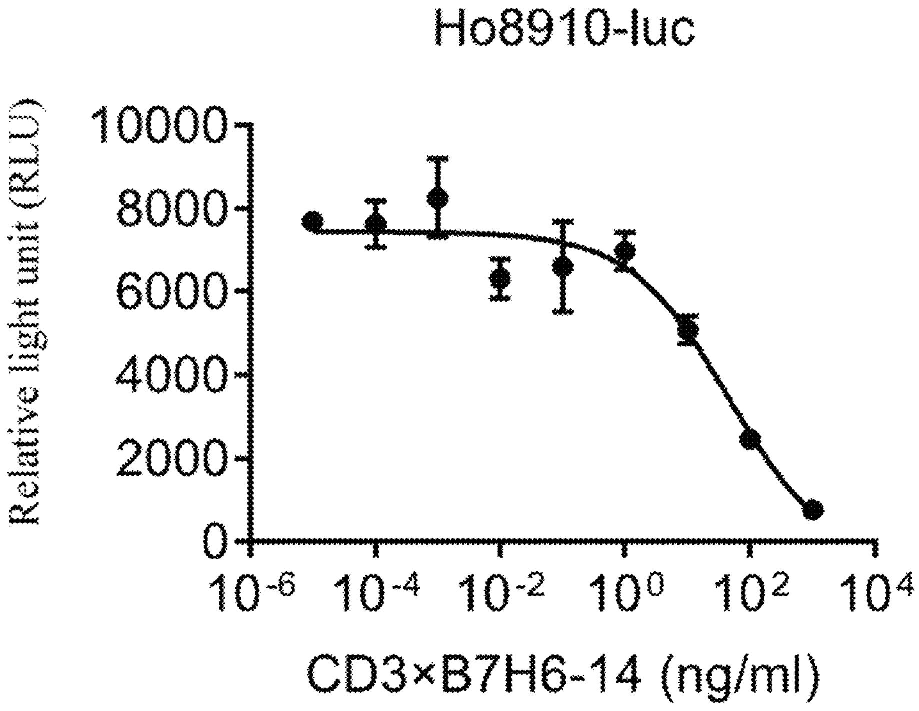
FIG. 4A is a chemiluminescence value analysis graph according to an embodiment of the present disclosure, gradient concentrations of a CD3xB7H6 recombinant bispecific antibody molecule being added into a mixture obtained by mixing T cells with Ho8910 cells overexpressing luciferase, and chemiluminescence values being detected 24 hours after the addition of a substrate for reaction.
Figure 4B:
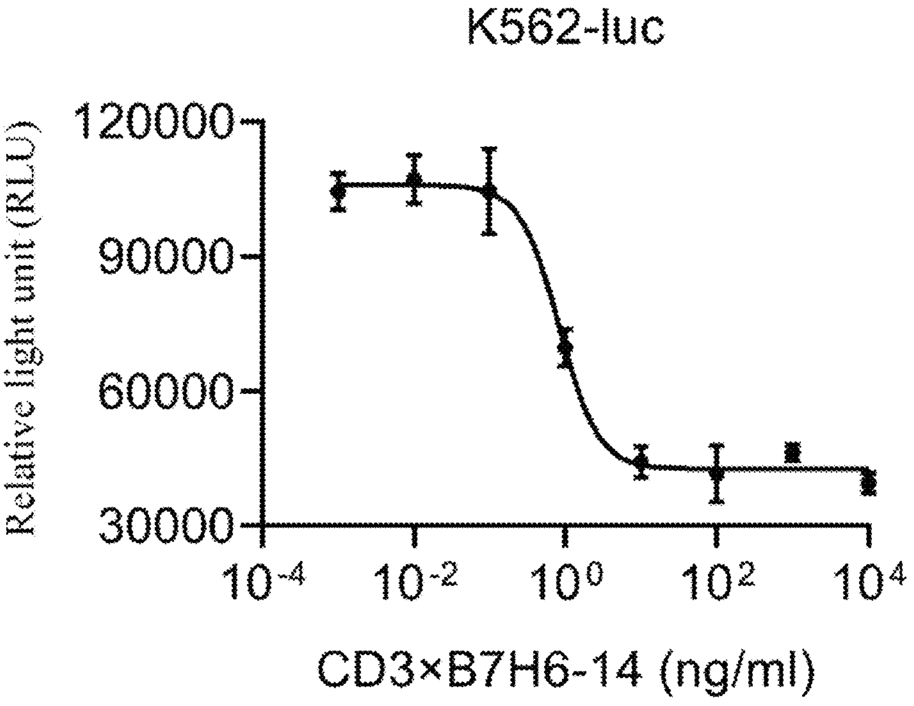
FIG. 4B is a chemiluminescence value analysis graph according to an embodiment of the present disclosure, gradient concentrations of a CD3xB7H6 recombinant bispecific antibody molecule being added into a mixture obtained by mixing T cells with K562 cells overexpressing luciferase, and chemiluminescence values being detected 24 hours after the addition of a substrate for reaction.

Specific experimental results are shown in the figure, the chemiluminescence values of Ho8910 and K562 were gradually decreased as the concentration of CD3xB7H6-14 bispecific antibody increased, indicating that fewer tumor cells survived, i.e., CD3xB7H6-14 can significantly promote T cell killing of Ho8910 cells (FIG. 4A) and K562 cells (FIG. 4B).

Example 6: Detection of T Cell Proliferation in the Presence of B7H6 Positive Tumor Cells To determine T cell proliferation, this example was set up as a 2*2 two-factor experiment, including the following groups: T cells+PBS group, T cells+CD3xB7H6-14 group, HCT-15+T cells+PBS group, HCT-15+T cells+CD3xB7H6-14 group. T cells were purified and isolated as described in Examples 4.1 and 4.2 and labeled with 5 μM cell Trace CFSE (Invitrogen, cat. No. C34554). The labeled T cells were then mixed with human colon cancer cells (HCT-15 cells) at an effect target ratio of 2:1, to which PBS or a bispecific antibody was added. After 3 days, the cells were harvested and T cell proliferation was detected by flow cytometer.

Figure 5A:
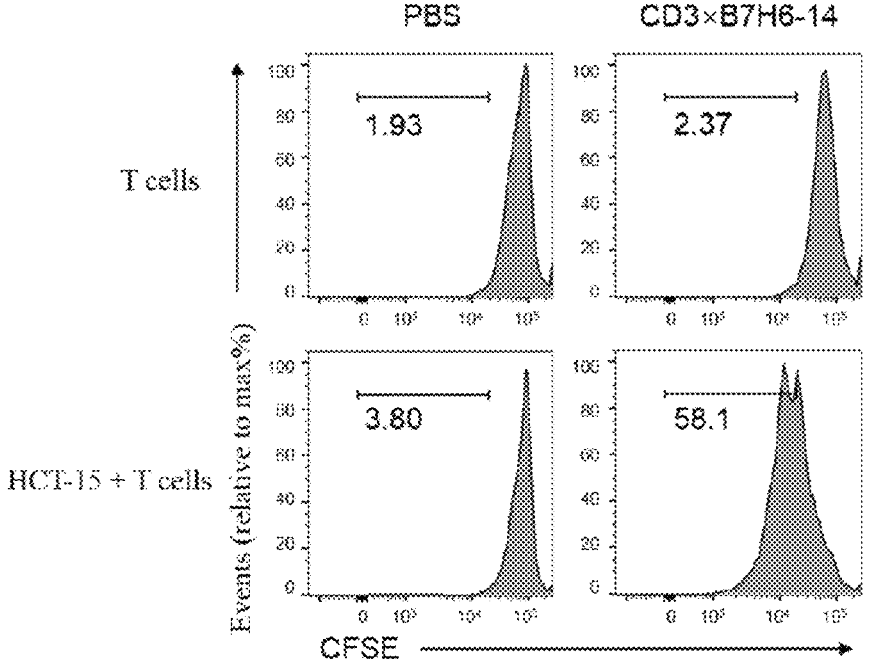
FIG. 5A is a graph showing the effect of CD3xB7H6 recombinant bispecific antibody molecules on T cell proliferation in the presence of HCT-15 cells according to an embodiment of the present disclosure.
Figure 5B:
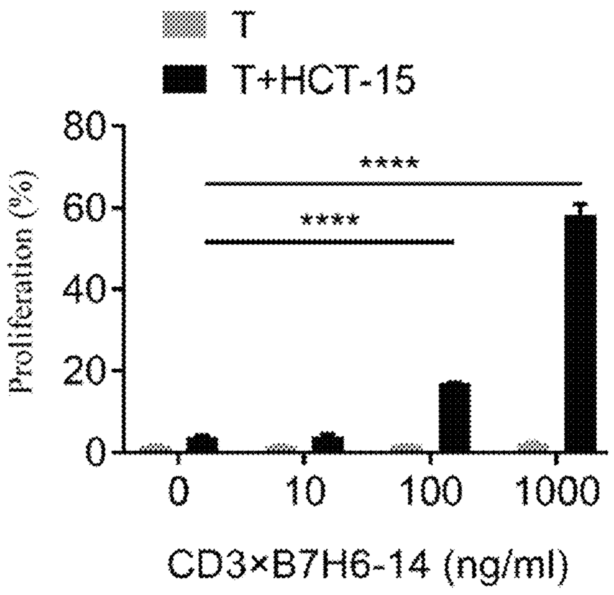
FIG. 5B is a statistical analysis graph of the effect of CD3kB7H6 recombinant bispecific antibody molecules on T cell proliferation in the presence of HCT-15 cells according to an embodiment of the present disclosure.

Specific experimental results are shown in the figures. The CD3x1371-16-14 bispecific antibodies significantly promoted T cell proliferation in the presence of HCT-15 (FIG. 5A), and the effect on T cell proliferation was more significant as the concentration of the bispecific antibody CD3xB7H6-14 was increased (FIG. 5B).

Example 7: Detection of T Cell Activation and Degranulation Levels in the Presence of B7H6 Positive Tumor Cells T cells are isolated and purified as described in Examples 4.1 and 4.2. Two groups are set up in the experiment. The control group was a T cell group, and in the experimental group, T cells and HCT-15 target cells were added into a 96-well plate at an effect target ratio of 1:1, and then CD3xB7H6 bispecific antibodies at gradient concentrations were added, and mixed well. After incubation at 37° C. for 24 h, the cells were collected by centrifugation, resuspended with PBS, blocked with mice serum at room temperature for 15 min, and then added with antibody for flow cytometry for detection of surface molecules. After incubation at 4° C. for 30 min in the dark, the cells were washed with PBS, and then fixed transmembrane solution (Invitrogen, cat. No. 00512343) was added for fixing at room temperature for more than half an hour. After washing with transmembrane buffer (Invitrogen, cat. No. 00833356) and blocking with mice serum at room temperature for 15 min, the corresponding intracellular molecular labeled antibody was added, incubated at room temperature for 30 min in the dark, washed twice with PBS and detected by flow cytometer.

Figure 6A:
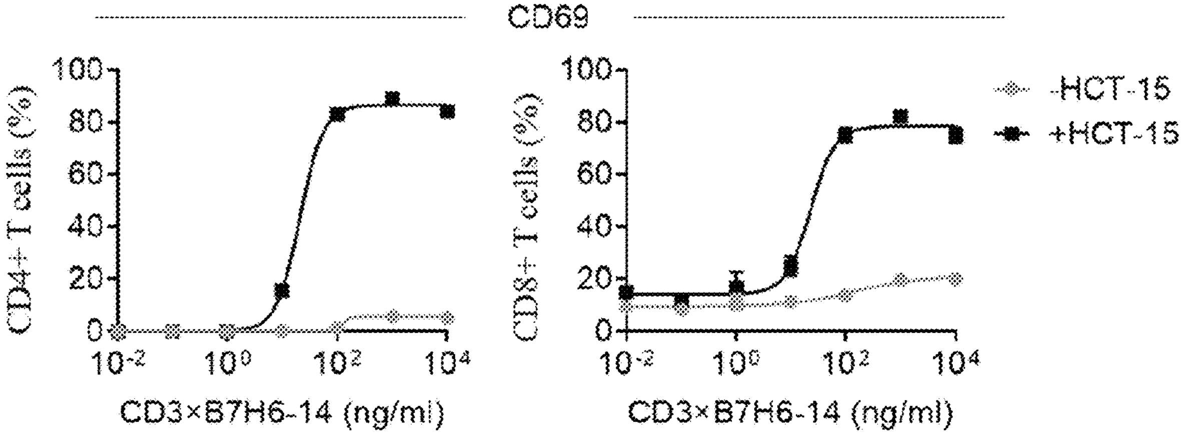
FIG. 6A is a graph showing the effect of CD3xB7H6 recombinant bispecific antibody molecules on $CD4^+$ and $CD8^+$ T cell activation in the presence of HCT-15 cells according to an embodiment of the present disclosure.
Figure 6B:
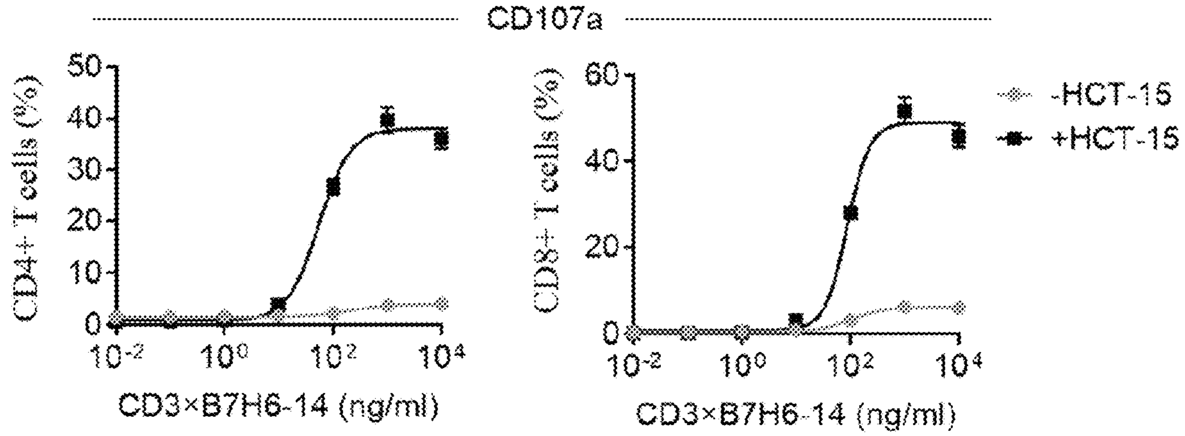
FIG. 6B is a graph showing the effect of CD3xB7H6 recombinant bispecific antibody molecules on $CD4^+$ and $CD8^+$ T cell degranulation level in the presence of HCT-15 cells according to an embodiment of the present disclosure.

Specific experimental results are shown in FIG. 6A and FIG. 6B. In the presence of B7H6+cells (+HCT-15), as the concentration of CD3xB7H6-14 bispecific antibody increased, the proportion of CD69 molecules expressed on the surface of CD4+T cells and CD8+T cells (FIG. 6A) and CD107a expressed in the cells (FIG. 6B) gradually increased, while in the absence of B7H6+ tumor cells (−HCT-15), the activation and degranulation of T cells after bispecific antibody incubation was limited. This indicates that the bispecific antibody can specifically target T cells and B7H6+ tumor cells and promote T cell activation and degranulation.

Example 8: Detection of Cytokines Secreted by T Cells in the Presence of B7H16 Positive Tumor Cells T cells are isolated and purified as described in Examples 4.1 and 4.2. The control group only contained T cells, and the experimental group contained T cells and HCT-15 cells. $5\times10^5$ T cells, $5\times10^5$ T cells and $5\times10^5$ HCT15 cells were respectively added into a 24-well plate in a total volume of 500 μL, and then CD3xB7H6 bispecific antibodies at gradient concentrations (0, $10^0$, $10^1$, $10^2$, $10^3$) were added, and mixed well. After incubation at 37° C. for 24 h, the supernatant was collected by centrifugation, and the concentration of each cytokine in the supernatant was determined using the CBA human Th1/Th2/Th17 cytokine detection kit (BD, cat. No. 560484) and finally determined by flow cytometer.

Figure 7A:
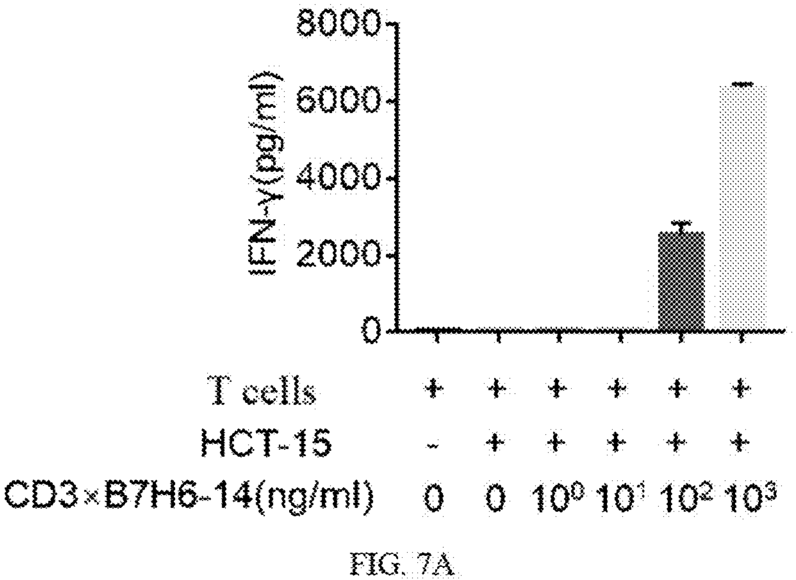
FIG. 7A is a graph showing the effect of a CD3xB7H6 recombinant bispecific antibody molecules on IFN-y secreted by T cells in the presence of HCT-15 cells according to an embodiment of the present disclosure.
Figure 7B:
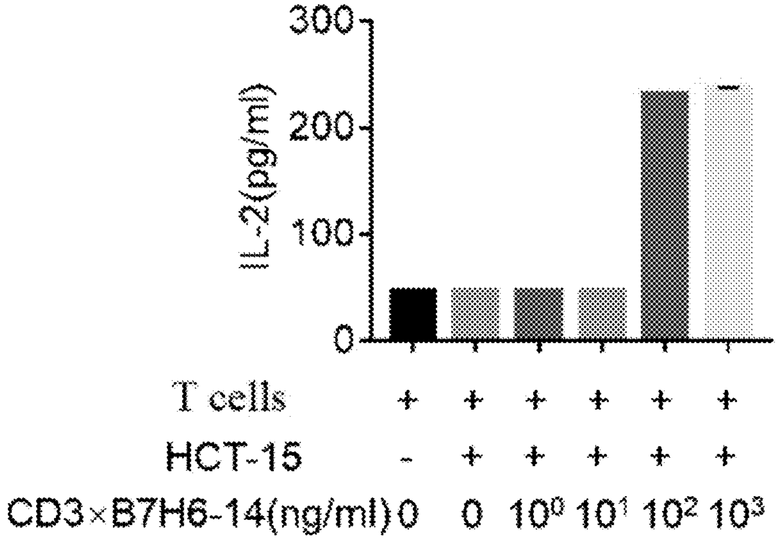
FIG. 7B is a graph showing the effect of CD3xB7H6 recombinant bispecific antibody molecules on secreted by T cells in the presence of HCT-15 cells according to an embodiment of the present disclosure.
Figure 7C:
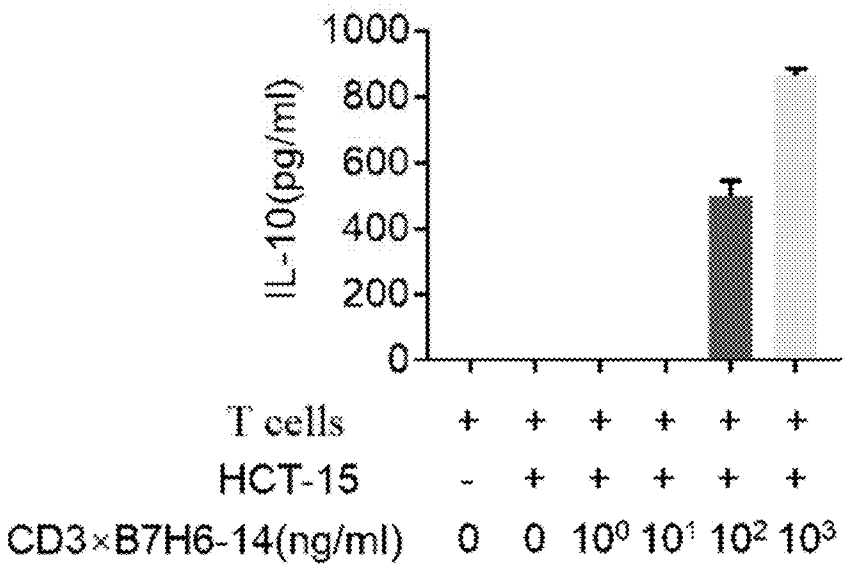
FIG. 7C is a graph showing the effect of CD3xB7H6 recombinant bispecific antibody molecules on IL-10 secreted by T cells in the presence of HCT-15 cells according to an embodiment of the present disclosure.
Figure 7D:
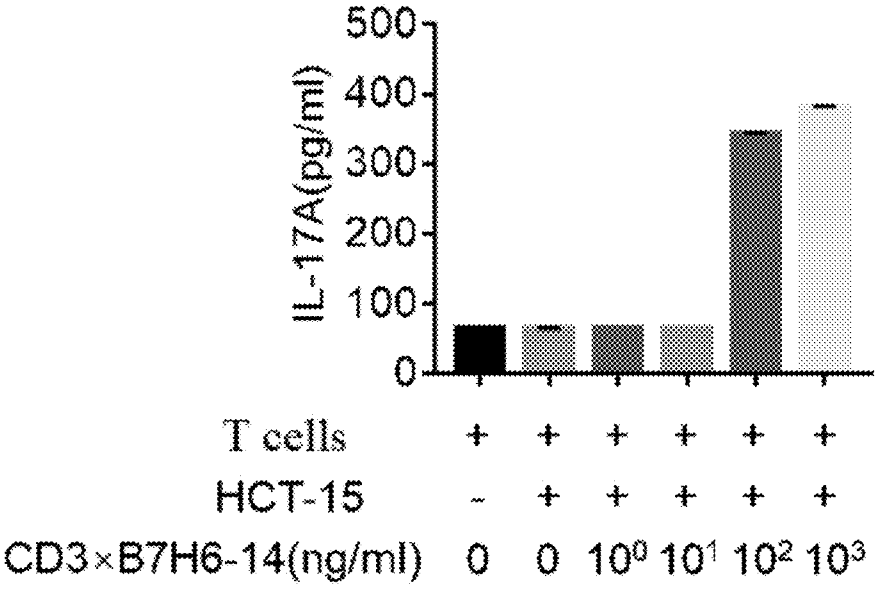
FIG. 7D is a graph showing the effect of CD3xB7H6 recombinant bispecific antibody molecules on IL-17A secreted by T cells in the presence of HCT-15 cells according to an embodiment of the present disclosure.

Specific experimental results are shown in FIG. 7A to FIG. D, in which the concentrations of IFN-y, IL-2, IL-10 and IL-17A cytokines in the cell co-incubation supernatant were shown, respectively. In the presence of HCT-15 tumor cells, the levels of these four cytokines secreted by T cells increased gradually with the increase of CD3xB7H6-14 antibody concentration, indicating that the bispecific antibody can promote T cell activation and cytokine secretion.

Example 9: Study on the Efficacy of Xenotransplantation In Vivo

To detect the in vivo anti-tumor activity of CD3xB7H6 bispecific antibody molecule on HCT-15 tumor cells, this example set up three groups for the experiment, including buffer group, human immunoglobulin (IGg) group and CD3xB7H6-14 bispecific antibody molecule group. T cells were isolated and purified as described in Examples 4.1 and 4.2 and amplified for 7 days using the T cell amplification kit (Gibco, cat. No. 11131D). HCT-15 colorectal cancer cells ($1\times10^6$) were mixed with amplified T cells ($2\times10^6$) and subcutaneously injected (s.c.) into male NOD-Prkdcscid Il2rgem1/Smoc mice, and CD3xB7H6 bispecific antibody (1 mg/kg in PBS), IgG control antibody (sigma, cat. No. I4506) or buffer (control solvent) was intravenously injected into the nice three times every two days after inoculation. Tumor length and width were measured by external calipers and tumor volume was calculated using standard formulas.

Figure 8:
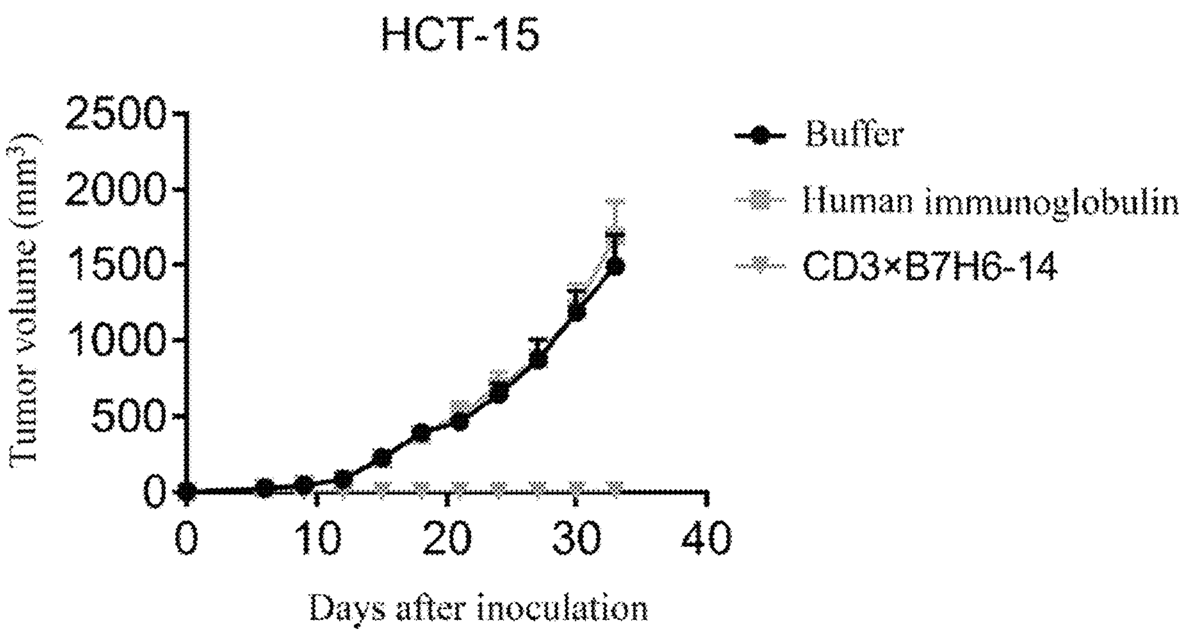
FIG. 8 is a graph showing the in vivo anti-tumor activity of CD3xB7H6 recombinant bispecific antibody molecules on HCT-15 cells according, to an embodiment of the present disclosure.

FIG. 8 shows the in vivo antitumor activity of CD3xB7H6-14 bispecific antibody molecules on HCT-15 cells. Treatment with CD3xB7H6-14 bispecific antibody significantly promoted the regression of HCT-15 tumor, but the therapeutic effect could not be achieved by using control IgG or control solvent, indicating that CD3xB7H6 bispecific antibody had significant anti-tumor activity in vivo.

In the description of the present disclosure, references to descriptions of the terms "one embodiment", "some embodiments". "examples", "specific examples", or "some examples", etc. mean that a particular feature, structure, material, or characteristic described in connection with the embodiment or example is included in at least one embodiment or example of the present disclosure. In this specification, schematic representations of the above terms are not necessarily directed to the same embodiment or example. Furthermore, the particular features, structures, materials, or characteristics described may be combined in any suitable manner in any one or more embodiments or examples. Furthermore, those skilled in the art can combine the various embodiments or examples as well as features in the various embodiments or examples described in this specification, without departing from the scope of the present disclosure.

While the embodiments of the present disclosure have been illustrated and described above, it will be understood that the above-described embodiments are illustrative and not restrictive and that changes, modifications, substitutions, and alterations may be made by those skilled in the art without departing from the scope of the present disclosure.

What is claimed is:

1. A recombinant antibody, comprising CD3 antibody variable region CDR sequences: SEQ ID NO: 1 to SEQ ID NO: 6; and B7H6 antibody variable region CDR sequences: SEQ ID NO: 7 to SEQ ID NO: 12.

2. The recombinant antibody according to claim 1, comprising CD3 antibody variable regions, wherein the CD3 antibody variable regions comprise:

a light chain variable region as set forth in SEQ II) NO: 13 and a heavy chain variable region as set forth in SEQ ID NO: 14; or an amino acid sequence having at least 70%, at least 75%, at least 80%, at least 85%, at least 90%, at least 95%, or at least 99% identity to an amino acid sequence as set forth in SEQ ID NO: 13, and an amino acid sequence having at least 70%, at least 75%, at least 80%, at least 85%, at least 90%, at least 95%, or at least 99% identity to an amino acid sequence as set forth in SEQ ID NO: 14.

3. The recombinant antibody according to claim 1, comprising B7H6 antibody variable regions, wherein:

the B7H6 antibody variable regions comprise: a light chain variable region as set forth in SEQ ID NO: 20 and a heavy chain variable region of the amino acid sequence as set forth in SEQ ID NO: 23; or an amino acid sequence having at least 70%, at least 75%, at least 80%, at least 85%, at least 90%, at least 95%, or at least 99% identity to an amino acid sequence as set forth in SEQ ID NO: 20, and an amino acid sequence having at least 70%, at least 75%, at least 80%, at least 85%, at least 90%, at least 95%, or at least 99% identity to an amino acid sequence as set forth in SEQ ID NO: 23;

the B7H6 antibody variable regions comprise: a light chain variable region as set forth in SEQ ID NO: 16 and a heavy chain variable region of the amino acid sequence as set forth in SEQ ID NO: 22; or an amino acid sequence having at least 70%, at least 75%, at least 80%, at least 85%, at least 90%, at least 95%, or at least 99% identity to an amino acid sequence as set forth in SEQ ID NO: 16, and an amino acid sequence having at least 70%, at least 75%, at least 80%, at least 85%, at least 90%, at least 95%, or at least 99% identity to an amino acid sequence as set forth in SEQ ID NO: 22;

the B7H6 antibody variable regions comprise: a light chain variable region as set forth in SEQ ID NO: 16 and a heavy chain variable region of the amino acid sequence as set forth in SEQ ID NO: 23; or an amino acid sequence having at least 70%, at least 75%, at least 80%, at least 85%, at least 90%, at least 95%, or at least 99% identity to an amino acid sequence as set forth in SEQ ID NO: 16, and an amino acid sequence having at least 70%, at least 75%, at least 80%, at least 85%, at least 90%, at least 95%, or at least 99% identity to an amino acid sequence as set forth in SEQ ID NO: 23;

the B7H6 antibody variable regions comprise: a light chain variable region as set forth in SEQ ID NO: 16 and a heavy chain variable region of the amino acid sequence as set forth in SEQ ID NO: 24; or an amino acid sequence having at least 70%, at least 75%, at least 80%, at least 85%, at least 90%, at least 95%, or at least 99% identity to an amino acid sequence as set forth in SEQ ID NO: 16, and an amino acid sequence having at least 70%, at least 75%, at least 80%, at least 85%, at least 90%, at least 95%, or at least 99% identity to an amino acid sequence as set forth in SEQ ID NO: 24;

the B7H6 antibody variable regions comprise: a light chain variable region as set forth in SEQ ID NO: 16 and a heavy chain variable region of the amino acid sequence as set forth in SEQ ID NO: 25; or an amino acid sequence having at least 70%, at least 75%, at least 80%, at least 85%, at least 90%, at least 95%, or at least 99% identity to an amino acid sequence as set forth in SEQ ID NO: 16, and an amino acid sequence having at least 70%, at least 75%, at least 80%, at least 85%, at least 90%, at least 95%, or at least 99% identity to an amino acid sequence as set forth in SEQ ID NO: 25;

the B7H6 antibody variable regions comprise: a light chain variable region as set forth in SEQ ID NO: 17 and a heavy chain variable region of the amino acid sequence as set forth in SEQ ID NO: 22; or an amino acid sequence having at least 70%, at least 75%, at least 80%, at least 85%, at least 90%, at least 95%, or at least 99% identity to an amino acid sequence as set forth in SEQ ID NO: 17, and an amino acid sequence having at least 70%, at least 75%, at least 80%, at least 85%, at least 90%, at least 95%, or at least 99% identity to an amino acid sequence as set forth in SEQ ID NO: 22;

the B7H6 antibody variable regions comprise: a light chain variable region as set forth in SEQ ID NO: 17 and a heavy chain variable region of the amino acid sequence as set forth in SEQ ID NO: 23; or an amino acid sequence having at least 70%, at least 75%, at least 80%, at least 85%, at least 90%, at least 95%, or at least 99% identity to an amino acid sequence as set forth in SEQ ID NO: 17, and an amino acid sequence having at least 70%, at least 75%, at least 80%, at least 85%, at least 90%, at least 95%, or at least 99% identity to an amino acid sequence as set forth in SEQ ID NO: 23;

the B7H6 antibody variable regions comprise: a light chain variable region as set forth in SEQ ID NO: 17 and a heavy chain variable region of the amino acid sequence as set forth in SEQ ID NO: 24; or an amino acid sequence having at least 70%, at least 75%, at least 80%, at least 85%, at least 90%, at least 95%, or at least 99% identity to an amino acid sequence as set forth in SEQ ID NO: 17, and an amino acid sequence having at least 70%, at least 75%, at least 80%, at least 85%, at least 90%, at least 95%, or at least 99% identity to an amino acid sequence as set forth in SEQ ID NO: 24, the B7H6 antibody variable regions comprise: a light chain variable region as set forth in SEQ ID NO: 17 and a heavy chain variable region of the amino acid sequence as set forth in SEQ ID NO: 25; or an amino acid sequence having at least 70%, at least 75%, at least 80%, at least 85%, at least 90%, at least 95%, or at least 99% identity to an amino acid sequence as set forth in SEQ ID NO: 17, and an amino acid sequence having at least 70%, at least at least 80%, at least 85%, at least 90%, at least 95%, or at least 99% identity to an amino acid sequence as set forth in SEQ ID NO: 25;

the B7H6 antibody variable regions comprise: a light chain variable region as set forth in SEQ ID NO: 19 and a heavy chain variable region of the amino acid sequence as set forth in SEQ ID NO: 22; or an amino acid sequence having at least 70%, at least 75%, at least 80%, at least 85%, at least 90%, at least 95%, or at least 99% identity to an amino acid sequence as set forth in SEQ ID NO: 19, and an amino acid sequence having at least 70%, at least 75%, at least 80%, at least 85%, at least 90%, at least 95%, or at least 99% identity to an amino acid sequence as set forth in SEQ ID NO: 22;

the B7H6 antibody variable regions comprise: a light chain variable region as set forth in SEQ ID NO: 19 and a heavy chain variable region of the amino acid sequence as set forth in SEQ ID NO: 23; or an amino acid sequence having at least 70%, at least 75%, at least 80%, at least 85%, at least 90%, at least 95%, or at least 99% identity to an amino acid sequence as set forth in SEQ ID NO: 19, and an amino acid sequence having at least 70%, at least 75%, at least 80%, at least 85%, at least 90%, at least 95%, or at least 99% identity to an amino acid sequence as set forth in SEQ ID NO: 23;

the B7H6 antibody variable regions comprise: a light chain variable region as set forth in SEQ ID NO: 19 and a heavy, chain variable region of the amino acid sequence as set forth in SEQ ID NO: 24; or an amino acid sequence having at least 70%, at least 75%, at least 80%, at least 85%, at least 90%, at least 95%, or at least 99% identity to an amino acid sequence as set forth in SEQ ID NO: 19, and an amino acid sequence having at least 70%, at least 75%, at least 80%, at least 85%, at least 90%, at least 95%, or at least 99% identity to an amino acid sequence as set forth in SEQ ID NO: 24;

the B7H6 antibody variable regions comprise: a light chain variable region as set forth in SEQ ID NO: 19 and a heavy chain variable region of the amino acid sequence as set forth in SEQ ID NO: 25; or an amino acid sequence having at least 70%, at least 75%, at least 80%, at least 85%, at least 90%, at least 95%, or at least 99% identity to an amino acid sequence as set forth in SEQ ID NO: 19, and an amino acid sequence having at least 70%, at least 75%, at least 80%, at least 85%, at least 90%, at least 95%, or at least 99% identity to an amino acid sequence as set forth in SEQ ID NO: 25;

the B7H6 antibody variable regions comprise: a light chain variable region as set forth in SEQ ID NO: 20 and a heavy chain variable region of the amino acid sequence as set forth in SEQ ID NO: 22; or an amino acid sequence having at least 70%, at least 75%, at least 80%, at least 85%, at least 90%, at least 95%, or at least 99% identity to an amino acid sequence as set forth in SEQ ID NO: 20, and an amino acid sequence having at least 70%, at least 75%, at least 80%, at least 85%, at least 90%, at least 95%, or at least 99% identity to an amino acid sequence as set forth in SEQ ID NO: 22;

the B7H6 antibody variable regions comprise: a light chain variable region as set forth in SEQ ID NO: 20 and a heavy chain variable region of the amino acid sequence as set forth in SEQ ID NO: 24; or an amino acid sequence having at least 70%, at least 75%, at least 80%, at least 85%, at least 90%, at least 95%, or at least 99% identity to an amino acid sequence as set forth in SEQ ID NO: 20, and an amino acid sequence having at least 70%, at least 75%, at least 80%, at least 85%, at least 90%, at least 95%, or at least 99% identity to an amino acid sequence as set forth in SEQ ID NO: 24, the B7H6 antibody variable regions comprise: a light chain variable region as set forth in SEQ ill NO: 20 and a heavy chain variable region of the amino acid sequence as set forth in SEQ ID NO: 25; or an amino acid sequence having at least 70%, at least 75%, at least 80%, at least 85%, at least 90%, at least 95%, or at least 99% identity to an amino acid sequence as set forth in SEQ ID NO: 20, and an amino acid sequence having at least 70%, at least at least 80%, at least 85%, at least 90%, at least 95%, or at least 99% identity to an amino acid sequence as set forth in SEQ ID NO: 25;

the B7H6 antibody variable regions comprise: a light chain variable region as set forth in SEQ ID NO: 15 and a heavy chain variable region of the amino acid sequence as set forth in SEQ ID NO: 26; or an amino acid sequence having at least 70%, at least 75%, at least 80%, at least 85%, at least 90%, at least 95%, or at least 99% identity to an amino acid sequence as set forth in SEQ ID NO: 15, and an amino acid sequence having at least 70%, at least 75%, at least 80%, at least 85%, at least 90%, at least 95%, or at least 99% identity to an amino acid sequence as set forth in SEQ ID NO: 26; or the B7H6 antibody variable regions comprise: a light chain variable region as set forth in SEQ ID NO: 18 and a heavy, chain variable region of the amino acid sequence as set forth in SEQ ID NO: 21; or an amino acid sequence having at least 70%, at least 75%, at least 80%, at least 85%, at least 90%, at least 95%, or at least 99% identity to an amino acid sequence as set forth in SEQ ID NO: 18, and an amino acid sequence having at least 70%, at least 75%, at least 80%, at least 85%, at least 90%, at least 95%, or at least 99% identity to an amino acid sequence as set forth in SEQ ID NO: 21.

4. The recombinant antibody according to claim 2, further comprising a linker peptide, optionally, the linker peptide having an amino acid sequence as set forth in SEQ ID NO: 46, wherein:

an N-end of the linker peptide is linked to a C-end of an CD3 antibody light chain variable region; and a C-end of the linker peptide is linked to an N-end of an CD3 antibody heavy chain variable region.

5. The recombinant antibody according to claim 3, further comprising a linker peptide, optionally, the linker peptide having an amino acid sequence as set forth in SEQ ID NO: 46, wherein:

an N-end of the linker peptide is linked to a C-end of a B7H6 light chain variable region; and a C-end of the linker peptide is linked to an N-end of the B7H6 heavy chain variable region.

6. The recombinant antibody according to claim 1, further comprising a first Fc region and a second Fc region, wherein at least a portion of the first Fc region and the second Fc region is derived from at least one of a murine antibody, a human antibody, a primate antibody, or a mutant thereof.

7. The recombinant antibody according to claim 6, wherein at least a portion of the first Fc region and the second Fc region is derived from human IgG or a mutant thereof, optionally, at least a portion of the first Fc region and the second Fc region is derived from human IgG1 or a mutant thereof.

8. The recombinant antibody according to claim 6, wherein the first Fc region has at least one of S384C mutation and T396W imitation as compared to a Fc region of wild-type IgG1.

9. The recombinant antibody according to claim 8, wherein the second Fc region has at least one of Y380C mutation, T397S mutation, L399A mutation, and Y408V mutation as compared to the Fc region of wild-type IgG1.

10. The recombinant antibody according to claim 7, wherein:

the first Fc region has an amino acid sequence as set forth in SEQ ID NO: 47 and the second Fc region has an amino acid sequence as set forth in SEQ ID NO: 48.

11. A recombinant antibody, comprising amino acid sequences as set forth in SEQ ID NO: 49 and SEQ ID NO: 63.

12. A nucleic acid, encoding the recombinant antibody according to claim 11.

13. The nucleic acid according, to claim 12, having a nucleotide sequence as set forth in SEQ ID NO: 69 and at least one of nucleotide sequences as set forth in SEQ ID NO: 70 to SEQ ID NO: 87.

14. An expression vector, comprising the nucleic acid molecule according to claim 12.

15. A recombinant cell, expressing the recombinant antibody according to claim 11.

16. A composition, comprising the recombinant antibody according to claim 11.

17. A medicament for use in the treatment or prevention of cancer, the medicament comprising the recombinant antibody according to claim 11.

18. The medicament according to claim 17, wherein the cancer comprises at least one of rectal cancer, non-small cell lung cancer, breast cancer, and liver cancer.

19. A kit, comprising, the recombinant antibody according to claim 11.

20. The kit according to claim 19, wherein the kit is used for diagnosing at least one of rectal cancer, non-small cell lung cancer, breast cancer, and liver cancer.

* * * * *